United States Patent
Tajima et al.

(10) Patent No.: US 8,445,265 B2
(45) Date of Patent: *May 21, 2013

(54) REACTION VESSEL AND REACTION CONTROLLER

(75) Inventors: Hideji Tajima, Chiba (JP); Yoshinao Hirahara, Chiba (JP); Osamu Segawa, Chiba (JP)

(73) Assignee: Universal Bio Research Co., Ltd., Matsudo-shi, Chiba (JP)

( * ) Notice: Subject to any disclaimer, the term of this patent is extended or adjusted under 35 U.S.C. 154(b) by 1082 days.

This patent is subject to a terminal disclaimer.

(21) Appl. No.: 11/664,980

(22) PCT Filed: Oct. 5, 2005

(86) PCT No.: PCT/JP2005/018419
§ 371 (c)(1),
(2), (4) Date: Jul. 1, 2009

(87) PCT Pub. No.: WO2009/038643
PCT Pub. Date: Apr. 13, 2006

(65) Prior Publication Data
US 2009/0298160 A1    Dec. 3, 2009

(30) Foreign Application Priority Data
Oct. 6, 2004 (JP) .................. 2004-294316

(51) Int. Cl.
*C12M 1/34* (2006.01)
*G01N 21/00* (2006.01)

(52) U.S. Cl.
USPC .................. 435/287.2; 435/287.3; 435/288.2; 435/288.7; 422/405; 422/501; 422/547; 422/559

(58) Field of Classification Search
USPC ...... 435/288.1, 288.2, 288.5, 288.7; 422/504, 422/511, 547, 559
See application file for complete search history.

(56) References Cited

U.S. PATENT DOCUMENTS

| | | | | |
|---|---|---|---|---|
| 3,691,017 A | * | 9/1972 | Brown et al. | 435/17 |
| 4,902,624 A | * | 2/1990 | Columbus et al. | 435/285.1 |
| 5,783,148 A | * | 7/1998 | Cottingham et al. | 422/417 |
| 5,863,502 A | | 1/1999 | Southgate et al. | |

(Continued)

FOREIGN PATENT DOCUMENTS

| | | |
|---|---|---|
| JP | 03-181853 | 8/1991 |
| JP | 05-281243 | 10/1993 |

(Continued)

OTHER PUBLICATIONS

U.S. Appl. No. 29/277,775, filed Mar. 9, 2007, Hideji Tajima.

(Continued)

*Primary Examiner* — William H Beisner
(74) *Attorney, Agent, or Firm* — Haynes and Boone, LLP

(57) ABSTRACT

The invention relates to a reaction vessel and a reaction controller, wherein temperature control of a liquid stored within the vessel can be performed with a high accuracy and faithful responsiveness. The reaction container and the reaction controller comprise one or a plurality of reaction chambers in which liquid is storable, and a wall that surrounds the reaction chamber, and the entirety or a part of the wall is formed by a temperature raising and lowering body that can raise or lower the temperature thereof according to a signal from an instructing part provided outside.

28 Claims, 20 Drawing Sheets

U.S. PATENT DOCUMENTS

| | | | |
|---|---|---|---|
| 6,197,595 | B1 | 3/2001 | Anderson et al. |
| 6,312,886 | B1 | 11/2001 | Lee et al. |
| 6,436,355 | B1 * | 8/2002 | Lee et al. .................. 422/199 |
| 7,101,509 | B2 * | 9/2006 | Chang et al. ............... 422/68.1 |
| 7,727,480 | B2 * | 6/2010 | Tajima ...................... 422/547 |
| 7,951,335 | B2 * | 5/2011 | Tajima ...................... 422/504 |
| 7,951,336 | B2 * | 5/2011 | Tajima ...................... 422/504 |
| 8,057,760 | B2 * | 11/2011 | Tajima ...................... 422/547 |
| 2001/0019826 | A1 | 9/2001 | Ammann |
| 2002/0090729 | A1 | 7/2002 | Neeper et al. |
| 2002/0168299 | A1 * | 11/2002 | Chang et al. ............... 422/102 |
| 2004/0166504 | A1 | 8/2004 | Rossier et al. |

FOREIGN PATENT DOCUMENTS

| | | |
|---|---|---|
| JP | 05-506930 | 10/1993 |
| JP | 08-062225 A | 3/1996 |
| JP | 09-262084 A | 10/1997 |
| JP | 10-117764 A | 5/1998 |
| JP | 10-323177 | 12/1998 |
| JP | 2000-241436 | 9/2000 |
| JP | 2000-346842 | 12/2000 |
| JP | 2001-002695 | 1/2001 |
| JP | 2001-074756 | 3/2001 |
| JP | 2001-509256 | 7/2001 |
| JP | 2002-102681 A | 4/2002 |
| JP | 2002-513936 | 5/2002 |
| JP | 2002-189033 | 7/2002 |
| JP | 2002-191351 | 7/2002 |
| JP | 2003-107083 | 4/2003 |
| JP | 2003-531381 | 10/2003 |
| JP | 2003-339374 | 12/2003 |
| JP | 2004-033907 A | 2/2004 |
| JP | 2004-061397 | 2/2004 |
| JP | 2004-359201 | 12/2004 |
| JP | 2004-359202 | 12/2004 |
| JP | 2005-003251 | 1/2005 |
| JP | 2005-030906 | 2/2005 |
| JP | 2005-278437 | 10/2005 |
| JP | 2006-24502 | 9/2006 |
| JP | 2006-24503 | 9/2006 |
| JP | 2006-024504 | 9/2006 |
| JP | 2006-24505 | 9/2006 |
| JP | 2006-24527 | 9/2006 |
| WO | WO 99/33559 | 7/1999 |
| WO | WO 00/67893 A1 | 11/2000 |
| WO | WO 00/78455 | 12/2000 |
| WO | WO 01/57253 | 8/2001 |
| WO | WO 03/004160 | 1/2003 |
| WO | WO 03/060115 | 7/2003 |
| WO | WO 2004/047992 | 6/2004 |
| WO | WO 2006/062235 | 6/2006 |
| WO | WO 2006/062236 | 6/2006 |
| WO | WO 2006/073170 | 7/2006 |

OTHER PUBLICATIONS

U.S. Appl. No. 29/277,777, filed Mar. 9, 2007, Hideji Tajima.
U.S. Appl. No. 29/277,778, filed Mar. 9, 2007, Hideji Tajima.
U.S. Appl. No. 29/277,779, filed Mar. 9, 2007, Hideji Tajima.
U.S. Appl. No. 29/277,780, filed Mar. 9, 2007, Hideji Tajima.
U.S. Appl. No. 11/792,783, filed Jun. 8, 2007, Hideji Tajima.
U.S. Appl. No. 11/792,835, filed Jun. 8, 2007, Hideji Tajima.
U.S. Appl. No. 11/794,828, filed Jul. 3, 2007, Hideji Tajima.
International Searching Authority "International Search Report," Feb. 20, 2006, 4 pages, International Serial No. PCT/JP2005/022775, Japanese Patent Office.
International Searching Authority "International Search Report," Feb. 27, 2006, 4 pages, International Serial No. PCT/JP2005/022776, Japanese Patent Office.
International Searching Authority "Written Opinion," Feb. 28, 2006, 5 pages, International Serial No. PCT/JP2005/022775, Japanese Patent Office.
International Searching Authority "Written Opinion," Mar. 7, 2006, 5 pages, International Serial No. PCT/JP2005/022776, Japanese Patent Office.
International Searching Authority "International Search Report," Apr. 4, 2006, 4 pages, International Serial No. PCT/JP2006/300064, Japanese Patent Office.
International Searching Authority "Written Opinion," Apr. 18, 2006, 8 pages, International Serial No. PCT/JP2006/300064, Japanese Patent Office.
International Preliminary Examination Authority, "International Preliminary Examination Report on Patentability," Dec. 12, 2006, 11 pages, International Serial No. PCT/JP2005/022775, Japanese Patent Office.
International Preliminary Examination Authority, "International Preliminary Examination Report on Patentability," Jul. 19, 2006, 8 pages, International Serial No. PCT/JP2005/022776, Japanese Patent Office.
International Preliminary Examination Authority "Written Opinion," Jan. 30, 2007, 6 pages, International Serial No. PCT/JP2006/300064, Japanese Patent Office.
International Preliminary Examination Authority, "International Preliminary Examination Report on Patentability," May 1, 2007, 11 pages, International Serial No. PCT/JP2006/300064, Japanese Patent Office.
Japanese Patent Office, "International Search Report," Jan. 24, 2006, 2 pages, Japan.
Extended European Search Report issued May 12, 2011, by the European Patent Office in connection with EP Application No. 05790543.2 (EP1801196) (2 pages).

* cited by examiner

REACTION VESSEL AND REACTION CONTROLLER

CROSS REFERENCE

This application is a United States national phase application of co-pending international patent application number PCT/JP2005/018419, filed Oct. 5, 2005, which claims priority to Japanese patent application number 2004-294316, filed Oct. 6, 2004, the disclosures of which are incorporated herein by reference.

TECHNICAL FIELD

The present invention relates to a reaction vessel and a reaction controller.

BACKGROUND ART

In recent years, the polymerase chain reaction (PCR) method is used in all biology related fields as a DNA amplification method that quickly and easily amplifies specific DNA fragments. The PCR method is a method that designs two primers that are complementary to the template DNA, and reproduces the area between the primers thereof within a test tube (in vitro). The method obtains the PCR products by exponentially amplifying the DNA by repeating temperature cycles wherein a reaction solution containing complementary DNA, primers, nucleotides, and thermostable DNA polymerase is incubated at various temperatures.

A single cycle comprises, with respect to a vessel charged with complementary DNA, the primer, DNA polymerase, nucleotides, and a reaction buffer solution; denaturation of the double stranded DNA into a single strand, annealing of the primer to the single stranded DNA, and incubation at the respective temperature conditions at which a DNA strand that is complementary to the single strand is synthesized, and a single molecule DNA fragment is made into two molecules. In the next cycle, since the DNA fragments synthesized in the previous cycle also become templates, the DNA fragments synthesized after n cycles becomes $2^n$ molecules.

Conventionally, in regard to temperature control, the next heating or cooling of the temperature is performed by accommodating the vessel, which is formed by glass, or the like, charged with complementary DNA, the primer, DNA polymerase, nucleotides and the reaction buffer solution, within a block-shaped housing section of a constant temperature device formed by a material of aluminum, or the like, and heating or cooling the metallic block-shaped housing section and waiting until the liquid temperature becomes a uniform temperature distribution (Patent Document 1).

Consequently, until the reaction liquid within the vessel is heated or cooled, as well as a long time being taken to reach a uniform temperature distribution in the liquid temperature due to the large capacity of the vessel, complex temperature changes occur as a result of the differences in the heat capacity or the specific heat of the housing section and the vessel, and there is a problem in that complex temperature instructions need to be performed in order to perform DNA amplification at a high accuracy.

Incidentally, in the PCR method, temperature control is important, and by changing the temperature cycles, the quality and quantity of the finally obtained PCR products can be changed.

In particular, in real time PCR, a more accurate quantification is performed by detecting and analyzing the generation process of the amplification product of PCR in real time, and a more accurate and quick temperature control is necessary. Consequently, a variety of devices have been proposed (Patent Document 2 to Patent Document 5). However, these apparatuses are large-scale and complex devices in that they are provided with complex flow passages, or used large-scale centrifugal devices, and the like.

On the other hand, the present inventor has disclosed a reaction vessel having a reaction vessel body which is furnished with a reaction chamber that stores the reaction liquid, and a cap member that seals an opening part of the reaction chamber, and in addition a pressing section wherein the cap member presses the reaction liquid, and this has made it possible to perform quick temperature control on a simple device scale without the need for centrifugal force (Patent Document 6).

However, the present inventor, by combining the thinning or capillaration of a liquid of high thermal efficiency, and a reasonable centrifugal process or suction/discharge process based on the particular shape of the vessel thereof, has reached the idea of performing and obtaining a simultaneous shortening and automation of a consistent process in regard to PCR, and the like, without using a large-scale device.

[Patent Document 1] Publication of Japanese Patent No. 2622327
[Patent Document 2] Japanese Translation of PCT International Application, Publication No. 2000-511435
[Patent Document 3] Japanese Translation of PCT International Application, Publication No. 2003-500674
[Patent Document 4] Japanese Translation of PCT International Application, Publication No. 2003-502656
[Patent Document 5] U.S. Pat. No. 5,958,349
[Patent Document 6] Japanese Unexamined Patent Application, Publication No. 2002-10777

DISCLOSURE OF INVENTION

Problems to be Solved by the Invention

Accordingly, the present invention has been achieved in order to solve the problems mentioned above, and a first object thereof is in providing a reaction vessel and a reaction controller wherein temperature control of a liquid stored within the vessel can be performed with a high accuracy and faithful responsiveness.

A second object is in providing a reaction vessel and a reaction controller in which the process can be quickly performed by shortening the time from when a heating or cooling instruction is given until the liquid temperature is uniformly distributed.

A third object is in providing a reaction vessel and a reaction controller in which a homogeneous reaction and highly accurate optical information is obtained as a result of thinning or capillaration of the liquid in a state where bubbles and gas regions have been removed from within the liquid.

A fourth object is in providing a reaction vessel and a reaction controller in which consistent processing can be efficiently and automatically performed in regard to the liquid, which is the processing subject, with a simple construction.

Means for Solving the Problem

A first aspect of the invention is a reaction vessel having one or a plurality of reaction chambers in which liquid is storable, and a wall that surrounds the reaction chamber, and an entirety or a part of the wall is formed by a temperature raising and lowering body that can raise or lower the temperature thereof according to a signal from the exterior.

Here, the "reaction chamber" is a space portion in which the liquid that becomes the subject of temperature control is to be stored. The "wall" refers to not only a side wall, but a portion that surrounds the reaction chamber, including a bottom wall, and the like. The "temperature raising and lowering body" refers to a member in which raising or lowering of the temperature thereof according to a signal from the exterior is possible.

The "signal" is, in a case where the temperature raising and lowering body is a conductive member, an electromagnetic signal, that is to say, a signal resulting from electricity or magnetism. It is also possible to detect the temperature resulting from the temperature raising and lowering body, and to generate a signal based on the temperature.

The "reaction vessel" has a portion (here, it is the reaction chamber) in which the liquid is storable, and has at least one opening part for introducing the liquid therein. If it has such a portion, it may not only be a case of a normal vessel shape provided with one opening part on the upper side, but it may also be a dispensing tip shape such that it has, in addition to one opening part, one liquid suction and discharging part on the lower side thereof. Furthermore, examples of the material of the reaction vessel include resins such as polyethylene, polypropylene, polystyrene, and acrylic, glass, metals, and metal compounds. The size is, for example, a size in which several μ liters to several hundreds of μ liters of the liquid is storable, as well as a size in which the end of a pipette tip is insertable. For example, in the case of a cylindrical shape, the diameter of the size of one reaction chamber is several millimeters to several tens of millimeters, and the depth is several millimeters to several tens of millimeters.

A second aspect of the invention is a reaction vessel wherein the wall is formed such that an inner wall face thereof faces into the reaction chamber, an outer wall face thereof is on the outside of the reaction chamber, and an interval between the inner and outer wall faces is integrally formed. That is to say, the portion of the wall sandwiched by the inner wall face and the outer wall face of the reaction chamber is, for example, formed as a wall such that it is not freely separable as a result of a metal, a resin, or the like, or a solid state in which these are bonded. Accordingly, in regard to a temperature raising and lowering body formed as the entire wall or a part of the wall, cases where it has a temperature raising and lowering body that is freely separable from the wall, for example, a temperature raising and lowering body that is merely in contact with the wall, a temperature raising and lowering body that is freely detachably installed to the wall by means of a screw and the like, a temperature raising and lowering body that is freely detachably installed with respect to a separate member that is installed to the wall by means of welding, and a temperature raising and lowering body that is completely separated from the wall, are separable and are therefore excluded. Consequently, if the reaction vessel is made to provide the temperature raising and lowering body as the wall of the reaction chamber such that it becomes a required thickness level, the size of the reaction vessel and the scale of the entire device can be restricted, and it can be handled without an awareness of the presence of a heating device.

A third aspect of the invention is a reaction vessel wherein the temperature raising and lowering body comprises a conductive member that has a predetermined electrical resistance, and the signal is an electromagnetic signal.

Here, the "predetermined electrical resistance" is a value at which the heat generation necessary for the conductive member to achieve a temperature that corresponds to the object by flowing a fixed electrical current into the conductive member, can be performed. For example, in surface resistance values, per unit area, it is approximately from several hundred $\Omega$ to several $\Omega$, and furthermore, a resistance value that makes inductive heating possible is, for example, several $\Omega$ cm or more. In regard to the conductive member, for example, there is a case where it comprises one type of material that has a predetermined electrical resistance, or there is a case in which two or more types of materials that have different resistance values are joined, welded, deposited, fused, bonded, attached, or pasted. In the former case, the temperature depends on the size of the electrical current value, which is the electromagnetic signal, and in the latter case, the temperature depends not only the electrical current value, but also on the orientation of the electrical current as a result of the Peltier effect, and cooling is possible as well as heating.

The "conductive member" may be, for example, a conductive material such as a metal, a metal compound such as a metal oxide, an alloy, a semiconductor, a metalloid, or a conductive resin, a material in which these conductive materials have been combined with a non-conductive material such as a ceramic, glass, or a synthetic resin, or a material in which the conducting materials have been combined with each other. For example, there are cases of aluminum, aluminum oxide, tin oxide, iron, an iron alloy, a nichrome alloy, or members that have been formed by two different conductive materials which have been bonded by adhesion, welding, or joining. By passing an electrical current through these members, or by applying a temporally oscillating magnetic field in the case of iron or an iron alloy, these members can be inductively heated. In a case where two types of metals have been joined, heating and cooling can be performed depending on the direction of the electrical current.

The shape of the conductive member is, for example, a wire form, a thin film form, a foil form, a film form, a thin plate form, a plate form, a long and narrow shape, or a layered form. In order to reinforce the conductive member, the conductive member may be bonded, welded, or deposited on a non-conductive member. The "electromagnetic signal" is an electrical signal resulting from the electrical current, or a magnetic signal resulting from the magnetic field, and excludes thermodynamic signals resulting from the application of heat or cold air of a predetermined temperature.

A fourth aspect of the invention is a reaction vessel wherein the reaction vessel is provided with a plurality of the aforementioned reaction chambers arranged in a plane at a predetermined interval.

Here, the "predetermined interval" includes, for example, a case where it is arranged in a matrix form at a fixed interval. The reaction vessel comprises reaction chamber portions, and a portion that connects the intervals between the walls that surround the reaction chamber, or a substrate, a base, a supporting plate or a supporting platform, which is a portion that supports the walls that surround the reaction chamber, or a supporting section.

A fifth aspect of the invention is a reaction vessel wherein the reaction vessel is provided with a contact section that receives an electrical signal by making contact with a terminal of an electromagnetic supply section provided to the exterior.

Here, the contact section may be the conductive member itself, or an electrode that is electrically connected to the conductive member. Furthermore, in regard to the contact section, in the case of a reaction vessel in which the walls of the reaction vessel or another part of the reaction vessel, for example, the opening part are multiply arranged with a brim, which is provided such that it is oriented towards the outside, a flange, and a reaction chamber, it is the substrate, the base, the supporting plate, the supporting platform, or the supporting section. By providing a contact section, since both the electrical connection with the exterior terminal and the supporting of the vessel can be combined, structurally, it becomes compact and easy to handle.

If the conductive member is a metallic member, it is also possible to raise or lower the temperature thereof by irradiating or not irradiating lines of magnetic force, which is a temporally oscillating magnetic signal, from the electromagnetic supply section provided on the exterior. In this case, examples of the metallic member include iron, and iron alloys such as stainless steel. The temperature of the temperature raising and lowering body can be changed depending on the temporal oscillation of the lines of magnetic force, which is a magnetic signal, or the strength of the lines of magnetic force.

A sixth aspect of the invention is a reaction device wherein the conductive member forms a wall of the reaction chamber, or covers the wall, is built into the wall, or is attached to the wall.

Here, "forms the wall of the reaction chamber" refers to the formation of the wall itself by the conductive member, "covers the wall" refers to the provision such that it covers the entirety of the wall face, and "attached to the wall face" refers to the provision on a part of the wall face.

A seventh aspect of the invention is a reaction vessel wherein the wall and/or a part or the entirety of the temperature raising and lowering body has translucency or semi-translucency.

Here, the reason for making "a reaction chamber in which a portion is translucent or semi-translucent" is in order to obtain the optical information within the reaction chamber, and, for example, it is for measuring the quantity or concentration of genetic material, such as DNA, which has been labeled with fluorescence, and the like, by real time PCR.

Here, "real time PCR" refers to a method of performing PCR while measuring the amplification quantity of DNA in real time. In real time PCR, electrophoresis is unnecessary, and this has the advantage in that the amplification is observable during the temperature cycles, and quantitative results are obtained. Methods that use normal fluorescent test reagents include the cycling probe method, the intercalator method, the Taqman probe method, and the Molecular Beacon method.

Here, examples of the translucent or semi-translucent material include glass, acrylic, polyethylene, polypropylene, and polystyrene. In order to form the temperature raising and lowering body such that it is translucent or semi-translucent, for example, it can be formed by thinly forming the conductive member in a foil film form on the translucent or semi-translucent material at a level such that light can be transmitted, and pasting or building it into the walls formed from the aforementioned material.

An eighth aspect of the invention is a reaction vessel wherein a wall that surrounds the reaction chamber has a plurality of wall faces, and amongst the wall faces, at least one is formed by a soft material film form member. Here, a single wall face refers to a surface in which the inclination continuously changes or the inclination becomes constant, and does not have discontinuous inclinations resulting from breaks, bending, and the like, that is to say, it is a single plane or a single curved surface. For example, a cylindrical reaction chamber has three wall faces, and a quadratic prism-shaped reaction chamber has six wall faces.

Here, examples of the "soft material" include rubber, silicone, polyvinyl chloride, vinyl acetal resin, and polyethylene.

A ninth aspect of the invention is a reaction vessel wherein a conductive member with a predetermined electrical resistance is coated, built in, or attached on the film form member, as the temperature raising and lowering body.

If the film form member is translucent or semi-translucent, and the temperature raising and lowering body is translucent or semi-translucent, the measurement of optical information and temperature control can be performed on the same side of the wall face. The conductive member is, for example, a thin film form, a wire form, a long and narrow shape, a foil form, a pattern such as a stripe form or a dendritic form, a thin plate form, a convex shape, or a block shape. By providing the thin film member on a large wall face with the largest area, temperature control can be efficiently performed.

A tenth aspect of the invention is a reaction vessel further comprising a storage chamber in which a liquid is storable, that has an opening part and is communicated with the reaction chamber, and the reaction chamber is formed thinner or narrower than the storage chamber.

Here, the "storage chamber" is a space portion in which a liquid is storable, and is provided to simplify the introduction of the liquid into the reaction chamber, which has been formed thinner or narrower than the storage chamber. The introduction of the liquid into the storage chamber is easily performed from the opening part, or via a flow passage.

The size or the thickness of the storage chamber is a size or a thickness at which the introduction of the liquid from the opening part to the storage chamber can basically be easily performed by gravity alone, or a size or a thickness in which it is possible to install a rotating body on the opening part.

Here the "reaction chamber" is a thinness (narrowness) level at which the introduction of the liquid is not easily performed by gravity alone in a state where the contamination of gas has been eliminated. The thickness or the width of the reaction chamber is, for example, 0.1 millimeters to 3 millimeters. Accompanying this, the handled liquid quantity corresponds to, for example, a few µ liters to 300µ liters. According to this quantity, the processing time of the PCR method corresponds to approximately several minutes to several tens of minutes.

Examples of the shape of the reaction chamber include those that have been formed in an approximate cylindrical shape. In that case, the side faces of the reaction chamber may be formed such that the area is smaller than both bottom faces, and the height between both bottom faces is thinner than the thickness of the storage chamber.

"Communication" for example between the storage chamber or the outside, and the reaction chamber, may be performed by an exclusive flow passage for passing a liquid. The "flow passage" is, for example, a portion that is formed narrower or thinner compared to the storage chamber, or, for example, at the interval between a thinned reaction chamber, the width thereof is narrowly formed, or, at the interval between a capillarated reaction chamber, for example, it is a portion having a different thickness to the reaction chamber. As a result of communication using a flow passage, the introduction of the liquid can be performed with certainty, the vessel is compactly formed, or the sealing of the reaction chamber is simplified, and it is easy to position the reaction chamber farther away from the rotation axis of a later described rotation body than the storage chamber. In order to introduce the liquid into the reaction chamber in a state where the contamination of gas has been eliminated, for example, this is performed by utilizing a centrifugal force or a suction force.

The reason for providing the "reaction chamber" that is thinner or narrower than the storage chamber is for improving the efficiency of the heating process such that by introducing the liquid into the reaction chamber, in regard to the liquid, at the very least, the heat transmission time in the thickness direction thereof is shortened, heat or temperature is transferred to the liquid in a short time, and a temperature distribution such that the liquid temperature promptly becomes uniform can be achieved.

Here the heating process is performed by raising or lowering the temperature of the temperature raising and lowering body that forms the entirety or a part of the wall that surrounds the reaction chamber. Instead of the temperature raising and lowering body, in order to cool the reaction chamber, this can be performed by a fan that blows air towards the reaction chamber, or by bringing a solid or a liquid cooling medium into contact with, or close to, the reaction chamber, or by ventilating cold air by means of a dryer.

If the wall with the largest area amongst the walls that enclose the reaction chamber, or the wall with the largest area, is heated or cooled, then temperature control can be performed efficiently. In a case where a target material, and the like, has been labeled with a fluorescent material, in order to obtain the optical information resulting from the fluorescence thereof, for example, this large wall is irradiated with an excitation light, and light is received from the same large wall, or from a small wall.

An eleventh aspect of the invention is a reaction vessel wherein the wall of the reaction chamber has a planar frame that has grooves or holes, and a film form member or a thin plate is provided such that it covers one face side or both face sides of the frame.

Here, in regard to the "film form member" or the "thin plate", there is the case of a soft material with flexibility, and there is the case of a non-flexible hard material. It is also possible to form the frame with a metallic member, and perform the raising or lowering of the temperature by irradiating or not irradiating the lines of magnetic force towards the frame from the exterior.

A twelfth aspect of the invention is a reaction vessel wherein an opening part of the reaction vessel has a connectable cap that is freely detachable. Here, the cap is one in which sealing of the opening part is possible, and the opening part and the cap are connected by, for example, attachment and contact methods, such as installation, engagement, threading, engaging fitting, engaging insertion, linking, close contact, and adhesion. Furthermore, the cap, for example, may be attachably provided between the lower end section of the rotating body of the liquid introducing device by means of installation, and the like.

A thirteenth aspect of the invention is a reaction vessel wherein the reaction vessel has a connection section that is detachably connectable to a liquid introducing mechanism provided on the exterior, and liquid is introducible into the reaction chamber by connecting the connection section to the liquid introducing mechanism.

Here, the "liquid introducing mechanism" is, for example, a rotating body that is installable to the reaction vessel and a rotational driving section that drives the rotating body, or a nozzle that connects to the reaction vessel and a suction and discharge section that suctions or discharges gas with respect to the nozzle. Furthermore, the rotating body may, at the same time, be a nozzle The liquid introducing mechanism has, for example, a function that introduces the liquid from the storage chamber to the reaction chamber or from the exterior to the reaction chamber, or a function that introduces the liquid to the exterior or from the exterior through the reaction chamber to the storage chamber, and is provided such that it is connectable to the vessel. For the introduction of the liquid, for example, a rotation mechanism of the vessel that introduces the liquid into the reaction chamber by applying a centrifugal force to the liquid, or a nozzle provided with a suction or discharging mechanism that is performed by suction and discharge of the liquid into the reaction chamber, are used.

The "connection" includes installation, engagement, engaging insertion, engaging attachment, engaging fitting, linking, threading, close contact, or adhesion of the reaction vessel to the liquid introducing section, or accommodation or installation of the entire reaction vessel in the liquid introducing mechanism, or other installation, contact, and accommodation methods of the same level as these that take into consideration the gist of the invention. In regard to the rotating body, there is a case where it is connected at the upper side of the reaction vessel, and a case where it is connected at the lower side of the reaction vessel.

In order to make it "connectable such that it is freely detachable", for example, a reaction vessel is arranged beforehand, the installation portion of the liquid introducing mechanism is moved and connected as a result of engagement, threading, and the like, and detachment is, for example, performed by moving a plate for stripping the reaction vessel from the connection portion, or rotating in the reverse direction to the direction of threading.

A fourteenth aspect of the invention is a reaction vessel wherein the liquid introducing mechanism has a rotatable rotating body, the reaction vessel is installable to the rotating body at the connection section, and the reaction vessel is installed to the rotating body and is rotatable together with the rotating body.

Here, since the reaction vessel has an opening part on the storage chamber or the reaction chamber, in order to achieve the function as a vessel, there is a need for it to be installed such that the liquid does not come out from the opening part to the outside in a case where the liquid introducing mechanism is a rotating body and the vessel is installed to the rotating body. That is to say, the opening part is not installed facing downwards or facing sideways without being blocked by a rotating body or another lid member thereof. Accordingly, in a case where the opening part is not blocked by a cap or the like, there is a need for the opening part to be open facing upwards when it is used as a vessel or when it is connected to a rotating body such that the liquid is storable, and in regard to when it is installed on the rotating body of the vessel, the direction in which the opening part thereof is open and the rotation axis of the rotating body thereof become parallel in the vertical direction. A cap that blocks the opening part may be provided on the opening part.

Furthermore, at the time the reaction vessel is installed on the rotating body, it is preferable for the rotation axis of the rotating body to pass through the vessel and for the reaction chamber to be formed such that it is positioned farther away from the rotation axis than the storage chamber. Hence, the vessel is rotatable about its own axis by means of the rotating body. The "rotation axis" is different to a specific rotation axle, and denotes an abstract central line of rotation. At the time the reaction vessel is installed to the rotating body, in a case where the rotation axis of the rotating body passes through the vessel, the rotation supporting axle, which protrudes out on the lower side of the vessel along the rotation axis, is installed to a bearing provided on the exterior, and the reaction vessel can be rotated with respect to the rotation axis in a stable state by rotating the rotating body.

The "object rotates about its own axis" refers to the object rotating about a rotation axis that passes through the object, and it is a concept that contrasts revolution, in which an object rotates about a rotation axis provided to the exterior of the object thereof. The liquid stored in the storage chamber, as a result of the high-speed rotation of the rotating body, moves to the reaction chamber that is connected at a position farther away than the storage chamber with respect to the rotation axis as a result of a centrifugal force, and since gas has a smaller specific gravity than liquid, it moves in a direction closer to the axis than the liquid, and the liquid can be introduced into the reaction chamber in a state where it is not contaminated by gas. Furthermore, if the reaction chamber is placed on the underside of the storage chamber, gravity can also be used. Therefore, the introduction of the liquid into the reaction chamber can be made even easier. Here, "high-speed rotation" represents, for example, several hundred rpm to several thousand rpm.

Furthermore, the reaction chamber is positioned farther away from the rotation axis than the storage chamber, and for example, as shown in FIG. 8, there is a case in which it comprises a storage chamber having an opening part, and a reaction chamber that is communicated with the storage chamber and is formed thinner or narrower than the storage chamber, or, there is a case in which it comprises a narrow tubular or thin layer form reaction chamber that extends diagonally downwards from the lower side of the fat tubular storage chamber, which has an opening part on the upper side. In regard to "positioned farther", for example, the one with the longer distance between the rotation axis and the center of gravity or the center of the portions that are the subject, is determined as the farther object.

Since the "vessel is installable to a rotatable body", the vessel has an installing section that can be installed on the rotating body, serving as a connection section. The installing section is, for example, the opening part or another portion of the vessel, or there are cases where it is the entire vessel. Since such an installing section itself is a portion of the vessel or the entire vessel, the rotation axis passes through the vessel. "Installing" includes, in regard to a portion of the vessel or the entire vessel, engagement, threading, engaging fitting, engaging attachment, engaging insertion, or accommodation of the entire vessel, or other installation methods. There are cases where the rotating body is installed on the upper side of the reaction vessel, and cases where it is installed on the lower side of the reaction vessel. The installation of the reaction vessel to the liquid introducing mechanism may be performed through the cap. That is to say, there are cases where this can be installed so as to be freely detachable, by means of a cap that is detachable to the bottom end portion of the rotation body.

Here, in a case where the opening part and the rotating body are installed by engagement or threading, there is a need for the installation portion of the opening part and the rotating body thereof to match. For example, for a cylinder, there is a need to have a cylindrical inner surface. Furthermore, in a case where the opening part and the rotating body are installed by threading, the rotation direction resulting from the rotating body is the direction in which the rotating body moves forward with respect to the opening part as a result of threading. In this case, the axis of the opening part and the rotation axis coincide.

Furthermore, for example, if a rotation supporting axle that protrudes out on the lower side of the vessel is provided along the rotation axis, and the rotation supporting axle is rotated with the axle supported, a stable rotation, in which the rotation axis does not deviate, can be applied. Here "rotation supporting axle" is an axle that is provided to enable smooth rotation of the reaction vessel accompanying rotation of the rotation body. The rotation supporting axle, for example in the case where the reaction vessel is installed on a rotation body at the opening portion of the storage chamber, is provided so as to protrude downward of the reaction vessel. Moreover, the downward protruding rotation supporting axle may also protrude upward, and be provided so as to connect the upper end of the rotation supporting axle to the rotation body.

In the case where the reaction vessel is rotatable about its own axis, there is no need to apply a centrifugal force by means of a large centrifugal device, and the device scale can be reduced. Furthermore, by utilizing a rotatable nozzle mentioned below, processing using the vessel can be consistently automated.

In a case where flow passages are provided to the reaction vessel, for example, it is acceptable if a liquid introduction flow passage for introducing the liquid from the storage chamber to the reaction chamber, and a discharge flow passage for discharging gas from the reaction chamber are provided, the liquid introducing mechanism has a rotatable rotating body, the reaction vessel is installable to the rotating body, and at the time of installation, the reaction chamber is formed such that it is positioned farther away from the rotation axis than the storage chamber and is rotatable together with the rotating body.

In this case, since the reaction chamber is provided with two flow passages, the reaction chamber consequently has two opening parts through which the liquid or gas is introduced or discharged. Here, the reason for providing the two flow passages of the liquid introduction flow passage and the discharge flow passage is to introduce the liquid into the reaction chamber in a state where it is not contaminated by gas, and to certainly and efficiently remove the gas. In regard to the gas to be discharged by the discharge flow passage, there is a case where it is returned to the storage chamber, and a case where it is discharged to the exterior. Consequently, it is possible to quickly, efficiently and smoothly perform the introduction of the liquid, and the discharging of the gas.

Furthermore, in regard to the rotation axis of this rotating body, a case where it passes through the vessel, and a case where it does not pass through the vessel, is possible. In the case where it passes through the vessel, the reaction vessel rotates about its own axis, but in the case where it does not pass through, the reaction vessel revolves about the rotation axis.

As a result of the liquid introduction flow passage being formed such that it is positioned farther away from the rotation axis for the case where the rotating body has been installed, than the discharge flow passage, discharging can be smoothly performed since the effect of the centrifugal force on the discharge flow passage is smaller than on the liquid introduction flow passage. In this case, if at least a portion of the discharge flow passage is provided along the rotation axis for the case where the rotating body is installed, the effect of the centrifugal force on the discharge flow passage can be made even smaller. "Installation" has been already explained, and therefore, explanation is omitted.

The reaction chamber is, for example, formed in an approximate cylindrical shape, and the side face of the reaction chamber has a smaller area than both bottom faces, and it is formed thinner than the storage chamber.

A fifteenth aspect of the invention is a reaction vessel wherein a deformable soft member is provided for at least a portion of the reaction vessel, and the reaction chamber is sealable by deforming the soft member.

Here, the "soft member" is a member formed from a soft material that is deformable by applying a pressing force. The "soft material" is for example as mentioned before, an elastic body such as rubber, or polyethylene or silicone. The soft material includes, for example, the film member that encloses the flow passages or the reaction chamber, or the block shaped member mentioned below that is provided for the flow passage or the reaction chamber.

The deformation of the soft member is, for example, performed by pressing the wall section of the reaction chamber or the flow passages that have been formed by the soft material. In a case where the soft member is formed by an elastic body such as rubber, there is a need to maintain the pressing force from the exterior to the elastic body in order to maintain the deformation.

For the soft member, there can be provided one which is an elastic block member that is deformable by means of a pressing force, and for which the interior has a void through which the passage of liquid and gas is possible. Here, the "void" includes pierced holes. As a member that is an "elastic block member" and that has a void in its interior, for example, the elastic valve mentioned below can be given. In order to seal the reaction chamber, there is a need to continuously apply a pressing force to the elastic block member.

As a result the liquid can be certainly and easily sealed in the reaction chamber. Furthermore, as a result of this, discharging of the introduced liquid from within the reaction chamber is prevented, and hence an efficient and quick introduction of the liquid and temperature control of the liquid can be achieved.

A sixteenth aspect of the invention is a reaction vessel wherein the rotating body is a nozzle in which suction and discharging of gas is possible, and the nozzle has a rotation axis in an axial direction thereof, or parallel to the same, and the connection section is an opening part of the storage chamber or the reaction chamber.

It is preferable for the "nozzle" to be formed such that it is installable with not only the vessel, but also with a dispensing tip. Since through a dispensing tip, the dispensing and transport of the liquid, and the like, can also be performed, processing with further diversity can be performed. Furthermore, it is preferable for the nozzle to be provided on the dispensing device, and vertical movement and horizontal movement to be made possible by means of technology that is apparent to those skilled in the art.

In this case, as the flow passages, a liquid introduction flow passage for introducing the liquid into the reaction chamber from the exterior, and a discharge flow passage for discharging gas from the reaction chamber, are provided, and the liquid introduction flow passage is a flow passage that extends from the reaction chamber in the downward direction, and by forming the flow passage with a small diameter, it is insertable into a variety of vessels provided on the exterior. Furthermore, the discharge flow passage communicates the interval between the reaction chamber and the storage chamber provided on the upper side thereof, and the nozzle is, for example, installed to the opening part of the upper side of the storage chamber. Hence, it is communicated on the upper side via the discharge flow passage.

According to the present aspect of the invention, in the case of the latter combination, the liquid is introduced into the reaction chamber via the liquid introduction flow passage by means of the suction of fluid by the nozzle, and the gas present in the reaction chamber is suctioned into the nozzle through the storage chamber via the discharge flow passage. At that time, a portion of the liquid may be suctioned into the storage chamber.

A seventeenth aspect of the invention is a reaction vessel having a flow passage that communicates the reaction chamber and the exterior, and the liquid introducing mechanism has a nozzle and a suction and discharge section that performs suction and discharging of gas via the nozzle, the connection section is an opening part of the reaction chamber or of a storage chamber which is communicated with the reaction chamber, and the opening part is connectable to the nozzle via the lower end section of the nozzle or a cap that is installable to the lower end section of the nozzle.

Here, "connection" includes contact and attachment methods such as installation, engagement, threading, engaging fitting, engaging attachment, engaging insertion, contact, or close contact.

Furthermore, the reaction chamber is, for example, communicated with the storage chamber via the upper section, and in regard to the suction and discharging port, for example, it is provided on the lower end of the flow passage that communicates at the lower section of the reaction chamber. Here, by forming the flow passage with a small diameter, it is possible to handle various vessels provided on the exterior. The size of the storage chamber is a size that can introduce the fluid into the reaction chamber by suction of the fluid, or a size that makes the suction and discharging by the nozzle possible. As a result of the consequent suction of the fluid by the nozzle, the fluid is introduced from the suction and discharging port into the reaction chamber.

In regard to the nozzle, it is preferable for it to be provided on a dispensing device in which horizontal movement and vertical movement is possible. Consequently, by moving the nozzle to vessels provided at various positions, it becomes possible to perform a further variety of processes. In regard to the nozzle, rotational movement including revolution is not necessarily made possible, although in a case where rotational movement is made possible, it benefits the homogenization of the liquid.

In regard to the interval between the storage chamber and the reaction chamber, there is a case where they are communicated via a flow passage, or there is a case where they are directly communicated at the interval between the storage chamber and the reaction chamber.

An eighteenth aspect of the invention is a reaction vessel wherein the reaction chamber is, within a pipette tip comprising a thick diameter section and a thin diameter section that is thinner than the thick diameter section, a gap formed between an outer face of a core which is stored inside an inner face of the pipette tip in which a spacer is intermediately present, and an inner face of the pipette tip, a flow passage that communicates the reaction chamber and the exterior is the thin diameter section, an opening part of the thick diameter section is connectable to the nozzle, and the temperature raising and lowering body is provided on a wall of the pipette tip, and/or on the entirety or a part of the core.

The spacer is, for example, a plurality of protrusion sections that protrude out in the outward direction from the outer face of the core, or a protrusion section that protrudes out in the inward direction from the inner face of the pipette tip. There is a need for this gap to be communicated with the thin diameter section and the upper side of the thick diameter section.

In this case, the nozzle serving as the liquid introducing mechanism, may be rotatable, and the nozzle may have a rotation axis along the axial direction thereof. In this case, as well as simplifying the introduction of the liquid into the reaction chamber by means of the rotation of the nozzle, the homogenization of the liquid can also be performed.

A nineteenth aspect of the invention is a reaction vessel wherein a predetermined variety of biological materials are arranged in predetermined positions on an outer face of the core, assigned to the positions by a predetermined relationship.

Consequently, for example, a predetermined variety of biological materials capable of bonding with a biological material labeled with a luminescent material such as a fluorescent material, are arranged in the predetermined positions, and by introducing the liquid in which the labeled biological material is suspended into the reaction chamber, and controlling the temperature raising and lowering body and reacting the same, and measuring the luminescent position thereof, it is possible to analyze the presence, the structure, and the character of the biological material.

In order to arrange the predetermined biological materials in the predetermined positions on the outer face of the core, in addition to a case where the predetermined biological materials are directly fixed in the predetermined positions on the outer face of the core, there is a case where they are arranged by winding a long and narrow shaped medium of a fibrous form or a filamentous form on which the predetermined biological materials are fixed in the predetermined positions, around the outer face of the core. In this case, by arranging the biological materials on the medium and winding the arranged medium around the core, the biological materials can be easily collected and arranged. Alternatively, by following along the medium, the luminescent position can be easily detected. The "positions" are determined by two dimensional position coordinates on the core, or by one dimensional position coordinates on the medium.

A twentieth aspect of the invention is a reaction vessel wherein the reaction chamber is sealable by sealing an interval between the nozzle or the storage chamber and the reaction chamber, and an interval between the reaction chamber and the exterior.

Here, as the "sealing device", for example, in regard to the interval between the nozzle and the reaction chamber, a first cap is freely detachably and engagingly insertably provided on the upper section of the storage chamber of the thick diameter section, and in regard to the cap itself, it is freely detachably provided such that it is connectable to the nozzle. By further moving the cap that is connected to the upper section of the thick diameter section in the downward direction at the upper section of the pipette tip, and by making it come into contact with the upper edge of the core stored within the pipette tip, the reaction chamber is sealed from the upper side. Furthermore, the lower side of the reaction chamber is sealed by engagingly inserting and installing the end of the thin diameter section into a second cap. That is to say, in a case where the first cap is moved by means of the lower end section of the nozzle, it is a raising and lowering movement device of the nozzle and a horizontal movement device that moves the nozzle to the position at which the second cap is disposed.

In order to seal the interval between the nozzle and the reaction chamber, for example, a first cap is engagingly insertably provided on the upper section of the storage chamber of the thick diameter section such that it is freely detachable, and in regard to the cap itself, it is freely detachably provided such that it is connectable to the nozzle. The cap that is installed to the upper section of the thick diameter section is further made movable in the downward direction of the upper section of the pipette tip, and by moving the cap in the downward direction and making it come into contact with the upper edge of the core stored within the pipette tip, the reaction chamber is sealed from the upper side. Furthermore, in regard to the lower side of the reaction chamber, by engagingly inserting and installing the end of the thin diameter section into a second cap, the reaction chamber is sealed from the top and the bottom.

On the other hand, in order to seal the interval between the storage chamber and the reaction chamber, and the interval between the reaction chamber and the exterior, a portion of the flow passage or the reaction chamber is formed by a deformable soft material, and in regard to the reaction chamber, it is performed by deforming the soft material. These caps, the movement device, or a pressing device for performing the deformation correspond to a sealing device.

A twenty-first aspect of the invention is a reaction controlling device having one or two or more reaction vessels, and an instruction section that generates a signal that instructs the raising or the lowering of the temperature with respect to the reaction vessel from the exterior, and the reaction vessel has one or a plurality of reaction chambers in which a liquid is storable, and a wall that surrounds the reaction chamber, and the entirety or a part of the wall is formed by a temperature raising and lowering body in which raising or lowering of the temperature is possible by means of a signal from the instruction section.

A twenty-second aspect of the invention is a reaction controlling device wherein the wall of the reaction vessel has an inner wall face thereof that faces into the reaction chamber, an outer wall face that is outside the reaction chamber, and an interval between the inner and outer wall faces is non-integrally formed.

A twenty-third aspect of the invention is a reaction controlling device wherein the temperature raising and lowering body has a conductive member that has a predetermined electrical resistance, and the instruction section has an electromagnetic supply section that applies an electromagnetic signal to the temperature raising and lowering body.

A twenty-fourth aspect of the invention is a reaction controlling device wherein the reaction vessel is provided with a plurality of the aforementioned reaction chambers arranged in a plane at a predetermined interval.

A twenty-fifth aspect of the invention is a reaction controlling device wherein the electromagnetic supply section makes contact with or is adjacent to a wall of the reaction chamber, or has one or a plurality of terminals that are provided such that they can approach and separate with respect to a wall of the reaction chamber.

Here, in regard to the "terminal", there is the case where electricity or an electrical current is supplied and there is the case where magnetism or a magnetic field is supplied. The "electromagnetic supply section" is, for example, formed such that it comprises a supporting section that freely detachably supports the reaction vessel, and a plurality of terminals that are provided such that they are able to make contact with or be adjacent to the wall of the reaction chamber in a state where they are supported by the supporting section. At that time, in the case of a reaction vessel in which a plurality of reaction chambers are multiply arranged such that they are joined via the wall thereof or a plate form substrate, it is acceptable for a plurality of hole sections to be provided at predetermined intervals on the supporting section such that each of the reaction chambers are storable, and for contact, and the like, between the terminals provided in the hole sections and the wall of the reaction chambers to be performed by storing the reaction chambers in the hole sections.

The conductive member is a metallic member, and in regard to the electromagnetic supply section, it is acceptable for the raising or the lowering of the temperature thereof to be made possible by irradiating or not irradiating temporally oscillating lines of magnetic force.

A twenty-sixth aspect of the invention is a reaction controlling device wherein there is further provided, in order to cool the reaction chamber, a fan that blows air towards the reaction chamber according to a signal from the instruction section, or a refrigerant circuit that follows along a route that makes contact with or is adjacent to the reaction chamber, and circulates a refrigerant according to a signal.

By sending in air by means of the fan, heat dissipation of the reaction chamber is promoted, and the heat control can be performed with good efficiency.

A twenty-seventh aspect of the invention is a reaction controlling device wherein the conductive member forms a wall of the reaction chamber, or covers a wall face of the wall, is built into the wall, or is attached to the wall.

A twenty-eighth aspect of the invention is a reaction controlling device wherein the wall and the entirety or a part of a temperature raising and lowering body has translucency or semi-translucency.

A twenty-ninth aspect of the invention is a reaction controlling device wherein a wall that surrounds the reaction chamber has a plurality of wall faces, and amongst the wall faces, at least one is formed by a soft material film form member.

A thirtieth aspect of the invention is a reaction controlling device wherein a conductive thin film with electrical resistance is coated, or built in, on the film form member, as the temperature raising and lowering body.

A thirty-first aspect of the invention is a reaction controlling device wherein the reaction vessel further has a storage chamber in which a liquid is storable, that has an opening part and is communicated with the reaction chamber, and the reaction chamber is formed thinner or narrower than the storage chamber.

A thirty-second aspect of the invention is a reaction controlling device wherein an opening part of the reaction vessel has a connectable cap that is freely detachable.

A thirty-third aspect of the invention is a reaction controlling device further having a liquid introducing mechanism whereby liquid is introducible into the reaction chamber by connecting to the reaction vessel, and the reaction vessel has a connection section that connects to the liquid introducing mechanism.

A thirty-fourth aspect of the invention is a reaction controlling device wherein the liquid introducing mechanism has a rotatable rotating body and a rotational driving section that rotationally drives the rotating body, and the reaction vessel is installed to the rotating body at the connection section of the reaction vessel and is rotatable together with the rotating body.

Here, in a case where the reaction vessel has a storage chamber, the reaction chamber is formed such that it is positioned farther away from the rotation axis of the rotating body than the storage chamber, and the reaction vessel introduces the liquid stored in the storage chamber into the reaction chamber by rotating as a result of the rotation of the rotating body.

According to the present device, centrifugal force is applied to the liquid present in the storage chamber of the reaction vessel, and the liquid can be introduced with certainty into the reaction chamber, which is positioned farther away from a rotation axis than the storage chamber, in a state where it is not contaminated by gas. The reaction vessel can use the reaction vessels according to the first aspect of the invention to the fifteenth aspect of the invention.

Here, in regard to the rotation axis, there is a case where it passes through the vessel and it rotates about its own axis, and there is a case where it passes through the outside of the vessel and it revolves. In the case of rotation about its own axis, as well as being able to reduce the device scale, a variety of processes can be performed in a compact device by using the nozzle itself as the rotating body. Moreover in the case of revolving, a large centrifugal force can be applied at low revolutions.

In regard to the "installation", this is as explained for the fifth aspect of the invention.

Here, in order to perform rotation about its own axis, there is a need to form the rotation axis of the rotating body installed to the vessel such that it passes through the vessel. In regard to the rotation axis of the rotating body, it is preferable for it to pass through the opening part of the storage chamber and make it installable to the opening part.

Consequently, the opening part is covered by the rotating body, and hence leaking of the liquid from the opening part can be prevented without covering the opening part with a cap, and the like. Moreover since the opening part used for introducing the original liquid can also be used for the installation of the rotating body, there is no need to provide a new rotating body attachment section on the vessel, and the structure is simplified.

Furthermore, it is possible to more certainly and easily install between the rotating body and the reaction vessel by threading or engagement, and particularly in a case where the rotating body is attached by threading, since the rotation of the rotating body can be utilized, it is efficient.

A thirty-fifth aspect of the invention is a reaction controlling device wherein a deformable soft member is provided for at least a portion of a wall of the reaction chamber, and a pressing section that seals the reaction chamber by pressing a predetermined portion of the soft member is provided on the exterior of the reaction vessel. (The terminal and the pressing section are provided on a plate that is provided such that it can approach and separate with respect to the reaction chamber).

Here as the place where the flexible member is provided, instead of the reaction chamber, this may be the flow passage. The flow passage has for example a liquid introduction flow passage for introducing liquid from the storage chamber or the exterior to the reaction chamber, and a discharge flow passage for discharging liquid from the reaction chamber. Here, in the case of the former combination, the liquid introducing mechanism is a rotating body, and in the case of the latter combination, it is a nozzle and a suction and discharging section. In the latter case, the reaction chamber is, for example, communicated at the upper section to the storage chamber, and the liquid introduction flow passage is a flow passage that extends from the reaction chamber in the downward direction, and by forming the flow passage with a small diameter, it is insertable into a variety of vessels provided on the exterior. Furthermore, the discharge flow passage communicates the interval between the reaction chamber and the storage chamber provided on the upper side thereof, and the nozzle is, for example, installed to the opening part of the upper side of the storage chamber. Hence, it is communicated on the upper side via the discharge flow passage.

According to the present aspect of the invention, in the case of the latter combination, the liquid is introduced into the reaction chamber through the liquid introduction flow passage by means of the suction of fluid by the nozzle, and the gas present in the reaction chamber is suctioned into the nozzle through the storage chamber via the discharge flow passage. At that time, a portion of the liquid may be suctioned into the storage chamber.

A thirty-sixth aspect of the invention is a reaction controlling device wherein the rotating body is a nozzle in which suction and discharging of gas is possible, and the nozzle has a rotation axis in the axial direction thereof, or parallel to the same, and the connection section is an opening part of the storage chamber or of the reaction chamber.

By using the nozzle also as the rotating body, a variety of diverse processes can be consistently performed by installing a dispensing tip, such as the suction and discharging of the liquid, and a homogenization process of the suspension. Furthermore, although it is necessary for the rotating body to have a movement section that is movable in the vertical direction, if it is also movable in the horizontal direction, by moving the rotating body to vessels provided in various positions, it becomes possible to perform a wider variety of processes.

A thirty-seventh aspect of the invention is a reaction controlling device wherein the reaction chamber is, within a pipette tip comprising a thick diameter section and a thin diameter section that is thinner than the thick diameter section, a gap formed between an outer face of a core which is stored inside an inner face of the pipette tip in which a spacer is intermediately present, and the inner face of the pipette tip, a flow passage that communicates the reaction chamber and the exterior is the thin diameter section, and an opening part of the thick diameter section is connectable to the nozzle.

A thirty-eighth aspect of the invention is a reaction controlling device wherein a predetermined variety of biological materials are arranged in predetermined positions on an outer face of the core, assigned to the positions by a predetermined relationship.

A thirty-ninth aspect of the invention is a reaction controlling device vessel liquid introducing device having a sealing device that fluidically seals an interval between the nozzle or the storage chamber and the reaction chamber, and an interval between the reaction chamber and the exterior.

Here, the "sealing device" is, for example, in a case where a part or all of the flow passage of the reaction vessel, or the reaction chamber, is formed by a deformable soft member, a pressing section that seals the reaction chamber by deforming the soft member. For example, in regard to the interval between the nozzle and the reaction chamber, a first cap is engagingly insertably provided on the upper section of the thick diameter storage chamber such that it is freely detachable, and in regard to the cap itself, it is freely detachably provided such that it is installable to the nozzle. By further moving the cap that is installed to the upper section of the thick diameter section in the downward direction of the upper section of the pipette tip, and by making contact with the upper end of the core, which is stored within the pipette tip, the reaction chamber is blocked from the upper side. Furthermore, the lower side of the reaction chamber is blocked by installing the end of the thin diameter section by engaging insertion to a second cap. That is to say, in a case where the first cap is moved by means of the lower end section of the nozzle, it is a horizontal movement device that moves the nozzle to a position at which the raising and lowering device of the nozzle and the second cap are positioned. Furthermore, the pressing section may be a protrusion section provided on the heating and cooling end section mentioned below, or a protrusion section provided on the end face of the irradiation end section of the optical information measurement device.

A fortieth aspect of the invention is a reaction controlling device having an optical information measurement section that obtains optical information within the one or two or more reaction chambers.

Here, in regard to the face of the reaction chamber that performs heating or cooling with respect to the reaction chamber, the face that receives the light from the reaction chamber, and the face that irradiates light to the reaction chamber, a case where they are the same face, and a case where they are different faces, is possible.

In regard to the optical information measuring section, at the very least, one or two or more light reception end sections for receiving light from the reaction chamber are provided in contact with, or in the vicinity of, the reaction chamber. In a case where the luminescent material is a fluorescent material, or the like, it has one or two or more irradiation end sections which irradiate excitation light for generating fluorescence.

The reaction chamber of the reaction vessel may be formed in a cylindrical shape, and enclosed by two cylindrically shaped large walls and small walls, which are side faces, and there may be provided with one or two or more light reception end sections that receive the light advancing in the radial direction of the cylinder. As a result, by irradiating or receiving light with respect to the side face, uniform optical information can be obtained.

In a case where an irradiation end face is provided for the reaction chamber, it is provided such that the light is irradiated in the radial direction.

A forty-first aspect of the invention is a reaction controlling device wherein the optical information measurement section has one or two or more irradiation end sections that irradiate light into the reaction chamber, and one or two or more light reception end sections that receive light from the reaction chamber, the irradiation end section is provided such that it makes contact with or is adjacent to a large wall face that has at least one largest area amongst a plurality of wall faces that surround the reaction chamber, and the light reception end section is provided such that it makes contact with, is adjacent to, or is able to approach and separate from, at least one wall face excluding a largest wall face.

The optical information measuring section may have: two or more irradiation end sections provided at each irradiation position of the reaction chamber of the two or more reaction vessels; a plurality of types of light sources that respectively generate light having a plurality of types of wavelengths; a light source selection section that temporally switches and selects one type of light from amongst the lights from the light sources, and simultaneously introduces it to the irradiation end sections; two or more light reception end sections provided at the light reception positions of the two or more reaction chambers of the reaction vessel; a light reception position selection section that temporally switches and selects the light from the light reception end sections; an optical filter selection section that temporally switches and selects among the plurality of types of optical filters that the light from the selected light reception position is to pass through; and a photoelectric element that sequentially inputs the light, which is the light from the selected light reception position, that has passed through the selected optical filter. As a result, even in the case where two or more labeled material are used with respect to two or more reaction vessels, the reaction chamber and the type of labeled material which becomes the target labeled material can be temporally switched, and processing can be performed using a small number of photoelectric elements. Therefore overall, the device scale can be reduced or simplified.

Here, providing a plurality of types of optical filter is, for example, for a case such as where a labeling material for labeling the DNA fragment, and the like, for which the quantity or the concentration is to be measured, that outputs light of a plurality of wavelengths is used in realtime PCR and the like within the reaction chamber. Consequently, by transmitting light having various wavelengths through an optical filter, the presence of the corresponding labeling material, or the quantity thereof, can be measured.

The "photoelectric element" is an electron element utilizing the photoelectric effect, and includes photoelectric cells, photomultipliers, photoconductive cells, phototransistors, photodiodes, and the like.

The irradiation of the light becomes necessary in order emit light by irradiating excitation light to a fluorescent material, and the like, that may be present in the reaction chamber.

Moreover, the optical information measuring section may comprise: two or more irradiation end sections provided at each irradiation position of the reaction chamber of the two or more reaction vessels; a plurality of types of light sources that respectively generate light having a plurality of types of wavelengths; a light source irradiation position selection section that temporally switches and selects one type of light from amongst the lights from the light sources, and temporally switches the selected light and introduces it to the irradiation end sections; two or more light reception end sections provided at the light reception positions of the two or more reaction chambers of the reaction vessel; an optical filter selection section that temporally switches and selects among the plurality of types of optical filters that the light from the light reception position is to pass through; and a photoelectric element that sequentially inputs the light that has passed through the selected optical filter. As a result, even in the case where two or more labeled material are used with respect to two or more reaction vessels, the reaction chamber and the type of labeled material which becomes the target labeled material can be temporally switched, and processing can be performed using a small number of photoelectric elements. Therefore overall, the device scale can be reduced or simplified.

The irradiation end section may be formed for example from a rod lens. The rod lens may be connectably provided with respect to the reaction chamber, and the focal distance point may be adjustable, so that efficient light irradiation can be performed.

A forty-second aspect of the invention is a reaction controlling device wherein the optical information measurement section has one or two or more irradiation end sections that irradiate light into the reaction chamber, and one or two or more light reception end sections that receive light from the reaction chamber, and the irradiation end section and the light reception end section are provided such that they make contact with, are adjacent to, or are able to approach and separate from one wall face of a plurality of wall faces that surround the reaction chamber.

A forty-third aspect of the invention is a reaction controlling device wherein the optical information measurement section has one or two or more irradiation end sections that irradiate light into the reaction chamber, and one or two or more light reception end sections that receive light from the reaction chamber, and the irradiation end section of the optical information measurement section is one wall face amongst a plurality of wall faces that surround the reaction chamber, and is provided such that it makes contact with, is adjacent to, or is able to approach and separate from a portion that is coated or is built in with a conductive film serving as the temperature raising and lowering body.

Effects of the Invention

According to the reaction vessel of the first aspect of the invention or the reaction controlling device of the twenty-first aspect of the invention, the entirety or a part of the wall that forms the reaction chamber of the reaction vessel is formed by a temperature raising and lowering body in which raising or lowering of the temperature thereof is possible according to a signal from the exterior.

Accordingly, compared to a case where the temperature raising and lowering body, such as a heater, is provided on the outside of the wall of the reaction vessel, since it is directly making contact with the interior of the reaction chamber, the reflection of heat by the wall is prevented, the heat can be even more efficiently transmitted with respect to the interior of the reaction chamber, the thermal efficiency is high, and accurate temperature control can be performed.

Since the wall of the reaction chamber is formed by the temperature raising and lowering body, the thermal efficiency is high, and there is no need to provide a temperature raising and lowering body, such as a metallic block, on the outside of the reaction vessel that is larger than necessary, and it is sufficient to simply provide a driving device thereof on the exterior. Accordingly, the structure of the exterior is simplified, and the device scale as a whole can be reduced.

Since it is possible to provide an optimal temperature raising and lowering body to the reaction vessels in advance, there is no need to provide a temperature raising and lowering body on the exterior that satisfies a variety of conditions, and it has generality and diversity.

Since the temperature raising and lowering body is making direct contact with the interior of the reaction chamber, temperature control of the liquid can be performed with a high precision and faithful responsiveness.

As a result of the reaction vessel or the reaction controlling device, the time from applying the signal for heating or cooling with respect to the liquid until the liquid temperature becomes a uniform temperature distribution is shortened, and the process can be quickly and efficiently performed.

According to the second aspect of the invention or the twenty-second aspect of the invention, the wall is integrally formed, and accordingly, since the temperature raising and lowering body that forms the entirety or a part of the wall is also integrally provided with the wall, in addition to demonstrating the aforementioned effects, the thermal efficiency is even higher, and temperature control can be performed with a high precision. Furthermore, the reaction vessel or the device can be made compact and the structure can be simplified, and it can be easily and cheaply produced. Furthermore, since it can be handled without an awareness of the heating device, it is easy to handle.

According to the third aspect of the invention, the fifth aspect of the invention, the twenty-third aspect of the invention, or the twenty-fifth aspect of the invention, the temperature raising and lowering body comprises a conductive member that has a predetermined electrical resistance. Accordingly, by means of the electrical or magnetic signal from the electromagnetic supply section, heating or cooling can be easily and certainly performed. Furthermore, the device scale can be simplified, the device scale as a whole can be reduced, and it can be inexpensively produced.

According to the present aspects of the invention, since the temperature raising and lowering body is provided to the reaction vessel itself, it can be used in a variety of reaction vessels without adhering to the shape of the reaction vessel as long the position of the contact section, and the like, are common. Therefore the standardization of the electromagnetic supply section and the reaction vessel is made possible. Furthermore, in regard to the conductive member, since heat generation with a small amount of material is possible by suitably setting the resistance value and the electrical current value, the size or the weight of the temperature raising and lowering body, and consequently the reaction vessel, can be made small and lighter.

Accidents such as only the heating device being driven without the presence of a reaction vessel are prevented beforehand, and furthermore, temperature control depending on the respective reaction vessels is performed, and reaction control with a high reliability can be performed.

According to the fifth aspect of the invention, since the electrical signal can be supplied as a result of making contact with the contact section, then by combining the contact section with the supporting section of the reaction vessel, the structure can be simplified and it is easy to handle. Furthermore, since the reaction vessel which has a predetermined structure, is installed at a predetermined position, and temperature control is performed for the first time by making contact with the contact section, it is even easier to prevent heat generation resulting from misoperation and malfunction.

According to the fourth aspect of the invention or the twenty-fourth aspect of the invention, a plurality of reaction chambers are provided such that they are arranged in a plane with a predetermined spacing. Consequently, since a plurality of reaction processes can be simultaneously performed, the operating efficiency is high.

By simultaneously applying the signal from the exterior to the temperature raising and lowering body, processing can be performed approximately under the same conditions. Therefore it is possible to perform parallel processing with respect to the plurality of specimens with a high reliability.

According to the twenty-sixth aspect of the invention, in addition to providing a temperature raising and lowering body to the reaction chamber, by providing a cooling device, such as a fan, to the exterior, not only heating, but cooling can be performed with certainty. Consequently, in a case where the reaction chamber is cooled, heat dissipation of the reaction chamber is promoted by sending in air by means of the fan, and the heat control can be performed with good efficiency.

According to the sixth aspect of the invention or the twenty-seventh aspect of the invention, since the wall is formed by a conductive member as a temperature raising and lowering body that is coated on, or built into the wall, temperature control can be easily performed by means of an electrical signal. Furthermore, since heat generation and the like, is performed by providing the conductive member on the wall itself, the efficiency is high. The device as a whole can be compactly formed. Not only in regard to the reaction vessel, but also in regard to the outside of the reaction vessel, since it can be handled without an awareness of the heating device, it is easy to handle.

According to the seventh aspect of the invention or the twenty-eighth aspect of the invention, the entirety or a part of the wall or the temperature raising and lowering body is formed such that it has translucency or semi-translucency. Consequently, since the optical information of the interior can be obtained not through the opening part of the reaction vessel, but through the wall, the results of reaction processing can be certainly and clearly obtained from the side face of the reaction vessel without obstructing connection processes, such as dispensing processes and installation, that require processes from the opening part.

Furthermore, in regard to real-time PCR and the like, the optical information within the reaction chamber can be easily obtained. In a case where the reaction chamber is not translucent or semi-translucent, the optical information is obtained by providing an optical waveguide within the reaction chamber.

According to the eighth aspect of the invention or the twenty-ninth aspect of the invention, since at least one of the walls that surrounds the reaction chamber is formed by a soft material film form member, by pressing the film form member, it becomes easier to seal the reaction chamber. As a result of sealing, the liquid is stored in the reaction chamber with certainty, and furthermore, temperature control can be certainly and efficiently performed. Furthermore, by absorbing the expansions and contractions of the liquid and gas that accompany the raising and lowering of the temperature, destruction and damage to the vessel can be prevented.

Furthermore, in a case where the film form member covers the flow passage portion that communicates with the reaction chamber, by pressing the film form member at the flow passage portion, it is easy to seal the reaction chamber.

According to the ninth aspect of the invention or the thirtieth aspect of the invention, as the temperature raising and lowering body, a conductive thin film or a conductive wire form member is used for the film form member. Consequently, since the portion at which the raising or lowering of the temperature is performed is the soft material film form member, it becomes even easier to absorb the expansions and contractions of the liquid and gas. Furthermore, since the temperature raising and lowering body is provided to the film form member, it is more difficult for heat to escape through transmission than when provided on a hard material, and therefore, it can be transmitted to the reaction chamber with good efficiency. Furthermore, since the lamination of the film form member and the attachment of the temperature raising and lowering body can be simultaneously performed, it is easy to process. Here, by providing the soft material film form member on the temperature raising and lowering body, it is possible to collectively perform the sealing of the reaction chamber as a result of pressing, and the contacting or making adjacent by the electromagnetic supply section. Furthermore, if the film form member is translucent or semi-translucent, it can be used for the measurement of the optical information within the reaction chamber. Therefore the device structure can be compactly formed. By providing the film form member on the large wall face with the largest area, the reaction chamber can be efficiently and uniformly heated.

By providing the film form member on the large wall face with the largest area amongst the wall faces that surround the reaction chamber, the raising and lowering control of the temperature of the reaction chamber can be efficiently performed.

According to the tenth aspect of the invention or the thirty-first aspect of the invention, by providing a storage chamber for the reaction vessel, and making the liquid temporarily storable in the storage chamber, the introduction of the liquid into the reaction chamber, which is formed thinner or narrower than the storage chamber, can be simplified. Furthermore, by heating or cooling the thinned or capillarated liquid in a state in which it is not contaminated by gas or bubbles, the process can be advanced quickly by shortening the time from giving the heating or cooling signal until the liquid temperature is uniformly distributed. In particular, if the heating or cooling of the liquid is performed such that the temperature raising and lowering body provided on the wall is sandwiched from both sides along the thickness direction, the liquid can be even more quickly and efficiently heated or cooled. The heating and cooling is made to be performed by the temperature raising and lowering body that forms the reaction chamber of the reaction vessel. Accordingly, an externally provided metallic block or the like is not necessary, and hence in regard to the thinned or capillarated liquid in a state in which it is not contaminated by gas or bubbles, temperature control of the liquid stored within the vessel can be performed with high precision and faithful responsiveness.

According to the eleventh aspect of the invention, by forming the planar frame, which has grooves or holes, by a film of a soft material that covers it from one side or both sides, even if the reaction vessel is a complex structure, a reaction vessel having a sealable reaction chamber can be easily and inexpensively produced.

According to the twelfth aspect of the invention or the thirty-second aspect of the invention, by providing a cap that is connectable to the opening part of the reaction vessel such that it is freely detachable, for example leaking of the liquid that is stored in the storage chamber, from the opening part to the exterior can be prevented. Furthermore, in a case where the nozzle of the liquid introducing mechanism can be installed to the cap such that it is freely detachable, the contact between the liquid and the nozzle or the like can also be prevented.

In particular, in a case where the liquid introducing mechanism is the rotating body, if a cap is provided on the lower end section of the rotating body such that it is freely detachable, and such that it covers the same, and the opening part of the vessel is made to be installed through the cap, in a case where high-speed rotation of the rotating body is performed, cross-contamination from splashing of the liquid and the rotating body directly coming into contact with the liquid within the vessel can be avoided with certainty. Furthermore, by preventing the splashing of the liquid to the upper part, the liquid is pushed back to the lower side, and a more efficient introduction of the liquid into the reaction chamber can be achieved.

According to the thirteenth aspect of the invention or the thirty-third aspect of the invention, by providing the liquid introducing mechanism, then for example by utilizing centrifugal force, and the like, thinning or capillaration can be performed in a state where contamination by bubbles or gas has been removed from within the liquid. Accordingly, at the time of temperature control, a homogeneous temperature distribution is obtained, and furthermore, highly accurate optical information can be measured.

Moreover, according to the reaction vessel, if it is communicated by providing one flow passage between the storage chamber or the exterior and the reaction chamber, the interval between the reaction chamber and the storage chamber can be separated in terms of distance. Accordingly, in the case where liquid introduction is based on centrifugal force, a large centrifugal force can be applied to the liquid that is to be introduced. Furthermore, in the case where liquid introduction is based on suction and discharge forces, by communicating the interval between the exterior and the reaction chamber through a narrow flow passage, it becomes possible to insert the end section of the flow passage into various vessels. Moreover, it becomes easier to suction and easier to handle even a small quantity of liquid. Furthermore, by blocking the flow passage, it becomes easier to make the reaction chamber sealable.

Furthermore, by detachably providing the reaction vessel with respect to the liquid introducing section such as a rotating body provided to the exterior, the reaction vessel can be disposably formed, and hence the process can be inexpensively performed.

According to the fourteenth aspect of the invention or the thirty-fourth aspect of the invention, a rotatable rotating body is provided for the liquid introducing mechanism.

At this time, by forming the reaction chamber so that it is separate from the rotation axis, or so that it is positioned farther from the rotation axis than the storage chamber, and by rotation with the rotation body connected to the reaction chamber, the reaction chamber rotates on about its own axis or revolves, and due to this rotation about its own axis or revolving, a centrifugal force is applied to the liquid giving centrifugal separation. As a result, liquid or solid suspended in the liquid can be introduced with certainty into the reaction chamber in a state where gas and bubbles have been removed.

At this time, if the rotation axis of the rotating body is passes through the vessel, and the reaction chamber is formed such that it is positioned farther away from the rotation axis than the storage chamber, the reaction vessel rotates on its own axis by means of the rotation of the rotation due to the rotating body connected to the reaction vessel, and as a result of this rotation about its own axis, centrifugal force is applied to the liquid, and as a result of centrifugal separation, liquid or solid suspended in the liquid can be introduced with certainty into the reaction chamber in a state where gas and bubbles have been removed. Furthermore, since the liquid is introduced by means of the reaction vessel rotating about its own axis, the liquid can be introduced with certainty without taking up space.

That is to say, since the liquid can be introduced into the reaction chamber by the rotation of the vessel about its own axis, a large space in which the reaction vessel is revolved around a rotation axis that passes only through the exterior thereof, is unnecessary, and the introduction of the liquid can be achieved by utilizing a small-scale rotation device of basically the size of one vessel. On the other hand in the case where the rotation axis does not pass through the vessel, then this revolves. In the case where revolving is performed, a large centrifugal force can be obtained at low revolutions.

In a case where the rotation axis of the rotating body is installed to the opening part such that it passes through the opening part of the storage chamber, since the opening part used originally for the introduction of liquid is also used for the installation of the rotating body, there is no need to provide a new rotating body attachment section on the vessel, and the structure is simplified.

Furthermore, it is possible to more certainly and easily install between the rotating body and the reaction vessel by threading or engagement, and particularly in a case where the rotating body is attached by threading, since the rotation of the rotating body can be utilized, it is efficient.

The fifteenth aspect of the invention or the thirty-fifth aspect of the invention is one that makes the reaction chamber sealable by providing a deformable soft member for at least a portion of the reaction vessel. Consequently, the liquid is certainly and efficiently stored in the reaction chamber by preventing the discharging of the introduced liquid from the reaction chamber, and temperature control can be certainly and efficiently performed. By sealing the reaction chamber, a reaction and measurement thereof with a high reliability can be performed in a state where gas has been removed. Furthermore, a quick and efficient introduction of the liquid can be achieved.

According to the sixteenth aspect of the invention or the thirty-sixth aspect of the invention, a nozzle is used as the rotating body. Consequently, in addition to the thinning or the capillaration of the liquid resulting from the introduction of the liquid into the reaction chamber, it can also be utilized for the dispensing of the liquid into the reaction vessel, and it can be applied to a variety of processes. Therefore a variety of processes can be consistently automated. Furthermore, if the rotation axis matches the axis of the nozzle, it can be rotated about its own axis, and the rotation radius is small, and the device scale can be restricted. Moreover by providing the rotation axis parallel with the axial direction of the nozzle, the opening part of the reaction vessel installed with the nozzle can face upward, and hence leakage of the liquid form the opening part can be prevented.

According to the seventeenth aspect of the invention, the nozzle is used as the liquid introducing mechanism, and the liquid is introduced into the reaction chamber by suction of the liquid to the storage chamber through the reaction chamber by means of the suction and discharging section. Accordingly, the liquid can be introduced with certainty into the reaction chamber without contamination by gas or bubbles. In this case, since there is no need to rotate the nozzle, the mechanism for introducing the liquid into the reaction chamber is simplified.

According to the eighteenth aspect of the invention or the thirty-seventh aspect of the invention, a core is stored in the pipette tip, the gap formed between the outer face of the core and the inner face of the pipette tip is used as the reaction chamber, the space portion within the thick diameter section of the upper side of the reaction chamber thereof is made the storage chamber, and a nozzle is installable to the opening part of the storage chamber, that is to say, the thick diameter section. Accordingly, by suctioning the liquid, which is stored within the vessel provided to the exterior from the thin diameter section by means of the nozzle, from the reaction chamber towards the storage chamber, the liquid can be introduced into the reaction chamber.

Furthermore, in regard to the product material produced by a reaction within the reaction chamber, by discharging gas from the nozzle, the product material can be discharged into the vessel from the reaction chamber through the thin diameter section, and the product material can be easily obtained.

According to the nineteenth aspect of the invention or the thirty-eighth aspect of the invention, by fixing a predetermined variety of biological materials at predetermined positions on the outer face of the core, and by measuring the luminescent position of the labeled target material that has reacted with the biological materials, analysis of the target material can be performed.

According to the twentieth aspect of the invention or the thirty-ninth aspect of the invention, by means of sealing the reaction chamber, and by quickly and easily preventing the discharging of the liquid, which has been introduced to the reaction chamber, from the reaction chamber, an efficient and quick introduction of the liquid can be performed.

According to the fortieth aspect of the invention, by providing an optical information measurement section, it is possible to consistently automate, from the introduction of the liquid into the reaction chamber, to the reaction and to the measurement. Furthermore, since the optical information within the reaction chamber is measured in a state where it is not contaminated by gas or bubbles, optical information of a high precision can be obtained.

According to the forty-first aspect of the invention, since by irradiating light on the wall with the largest area, a sufficient light quantity can be irradiated to the reaction chamber as a whole, optical information can be efficiently obtained.

According to the forty-second aspect of the invention, since the irradiation end sections and the light reception end sections are provided at one of the walls of the reaction chamber, as well as being able to make a compact configuration, the number of components can be reduced.

According to the forty-third aspect of the invention, by providing the temperature raising and lowering body and the irradiation end section on one wall, the device scale is reduced, and it can be efficiently arranged.

In conclusion, according to the first aspect to the forty-third aspect of the invention, by forming the temperature raising and lowering body on the wall of the reaction chamber of the reaction vessel, and by sending a signal from the exterior to the temperature raising and lowering body, it is possible for it to be inexpensively produced in a simple structure, the precision and responsiveness of temperature control of the liquid is increased, and for example, processes such as the measurement of quantities in real time PCR can be made quicker and more efficient.

BEST MODE FOR CARRYING OUT THE INVENTION

Next, embodiments of the present invention are explained based on the drawings. Unless particularly specified, these embodiments should not be interpreted as limiting the present invention. Furthermore, the same parts in the embodiments are denoted by the same reference symbols, and the explanations have been omitted.

Figure 1:
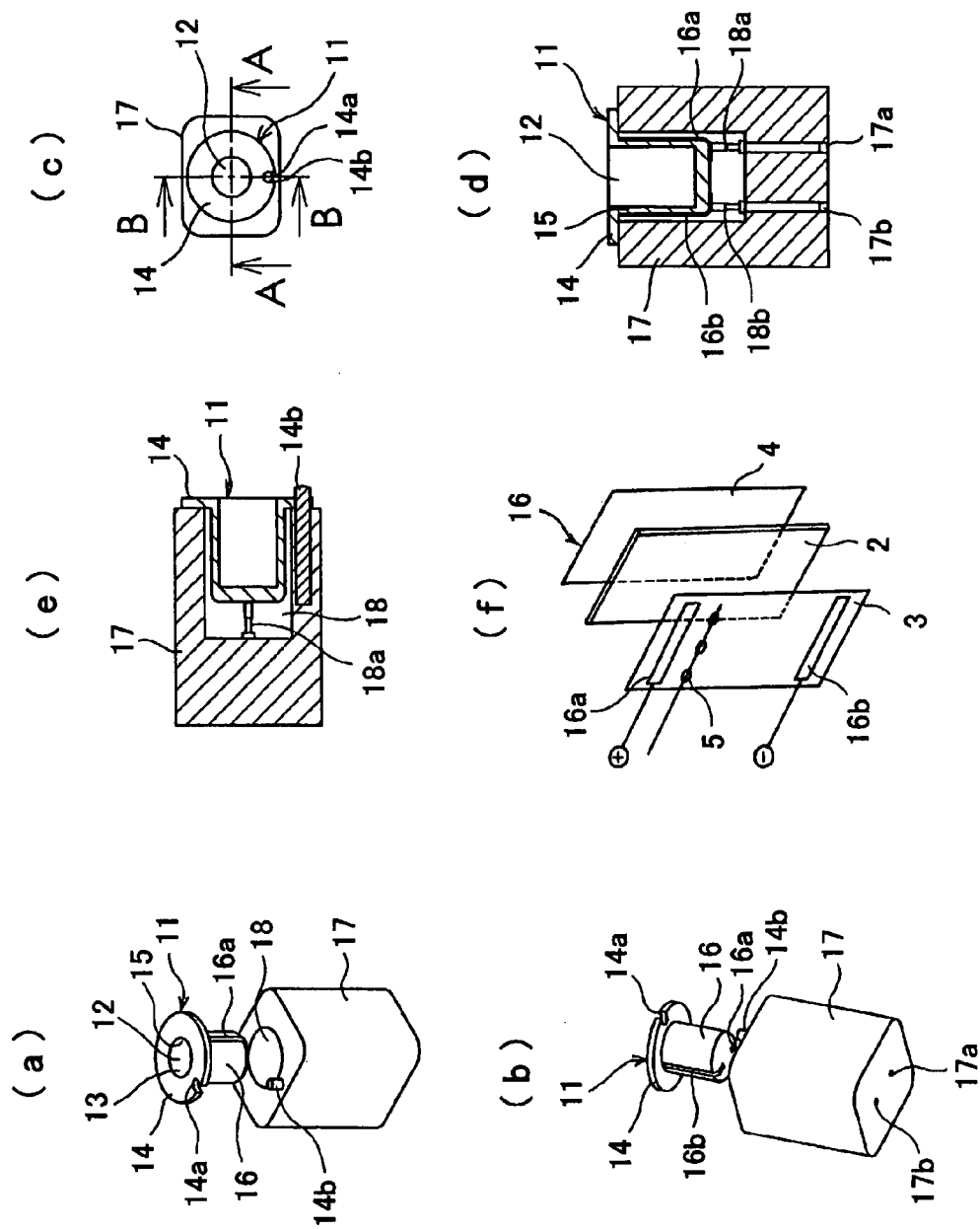
FIG. 1 is a drawing showing a reaction vessel according to a first embodiment of the present invention.

FIG. 1 (a) to (e) are a perspective view from the upper side and the lower side, a plan view, a side cross-sectional view and a front cross-sectional view showing a reaction vessel 11 and a supporting platform 17 that stores and supports the reaction vessel 11, according to a first embodiment of the present invention. In FIGS. 1 (a) and (b), the reaction vessel 11 comprises a reaction chamber 12 in which the liquid is storable, that is surrounded by a cylindrical wall 15. Furthermore, to an opening part 13 on the upper section of the reaction chamber 12, a circular plate form flange 14 is provided such that it protrudes out on the side of the wall 15. Moreover, the outside face of the wall 15 is coated with a conductive thin film 16 as a temperature raising and lowering body, which has a predetermined resistance value, and on the outer face of the wall 15, two narrow film form electrode films 16a and 16b, are provided as contact sections along the axial direction of the reaction vessel 11 such that they reach the bottom face side of the reaction vessel 11 thereof, in a state where they are electrically connected to the conductive thin film 16 in opposing positions such that they sandwich the central axis of the reaction vessel 11.

The supporting platform 17 that supports the reaction vessel 11 is larger than the outer diameter of the reaction chamber 12, and is provided with a vertical hole 18 for storing the reaction chamber 12, that has an inner diameter that is smaller than the outer diameter of the flange 14, and has a length that is deeper than the height of the reaction chamber 12. The bottom section of the vertical hole 18 is provided with pierced holes 17a and 17b.

A plan view of a state where the reaction vessel 11 is stored in the supporting platform 17 is shown in FIG. 1 (c), and in FIG. 1 (d) and FIG. 1 (e), a cross-sectional view on line AA and a cross-sectional view on line BB are respectively shown. As shown in the drawings, terminals 18a and 18b are provided on the upper side of the pierced holes 17a and 17b such that they protrude from the inner bottom section of the vertical hole 18 to the upper side. The terminals 18a and 18b are connected through the lower side of the pierced holes 17a and 17b to the instruction section provided to the exterior that supplies a predetermined electrical current, which is an electrical signal, or to an information processing device or a power circuit that corresponds to the electromagnetic supply section, via leads. In a case where the reaction chamber 12 of the reaction vessel 11 is stored in the vertical hole 18, the terminals 18a and 18b are able to make contact with the electrode films 16a and 16b.

The conductive thin film 16 serving as the temperature raising and lowering body that forms the reaction vessel 11 is schematically represented in FIG. 1 (f). The conductive thin film comprises an aluminum-made thin film 2, an aluminum oxide foil 3 that is coated on the aluminum-made thin film 2, and a polypropylene coating 4 that is coated on the opposite side of the aluminum-made thin film 2, wherein the polypropylene coating 4 is welded on the outside face of the wall 15 of the reaction chamber 12. Furthermore, on the outer surface of the aluminum oxide foil 3, the electrode films 16a and 16b which are formed by a metallic film with a high conductivity, are provided such that they are electrically connected. On the outer surface of the aluminum oxide foil 3, an electrode 5 of a temperature sensor is provided. The data obtained by the temperature sensor is input into an information processing device, which is not shown in the drawings, that corresponds to the instruction section, and is used in determining the size, orientation, and the like, of the electrical current, which is the electrical signal for temperature control. By flowing an electrical current between the electrode films 16a and 16b, heat generation of the conductive thin film 16 can be performed.

Figure 2:
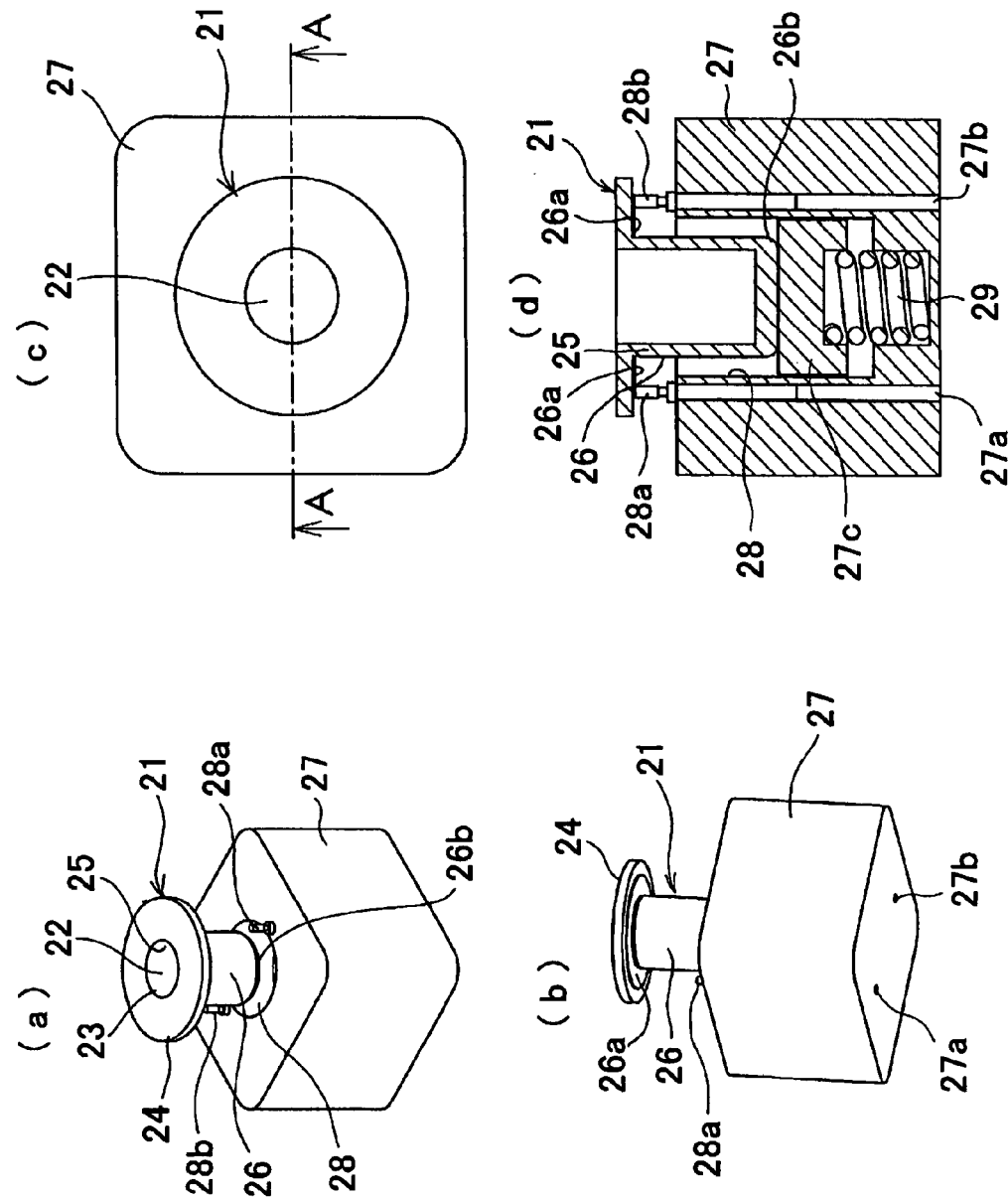
FIG. 2 is a drawing showing a reaction vessel according to a second embodiment of the present invention.

FIGS. 2 (a), (b), (c), and (d) are a perspective view from the upper side and the lower side, a plan view, and a cross-sectional view showing a reaction vessel 21 and a supporting platform 27 that stores and supports the reaction vessel 21 according to a second embodiment of the present invention. In FIGS. 2 (a) and (b), the reaction vessel 21 comprises a reaction chamber 22 in which the liquid is storable, that is surrounded by a cylindrical wall 25. Furthermore, to an opening part 23 on the upper section of the reaction chamber 22, a circular plate form flange 24 is provided such that it protrudes out on the side of the wall 25. Furthermore, the outside face of the wall 25 is coated with a conductive thin film 26 as the temperature raising and lowering body, which has a predetermined resistance value. The conductive thin film 26 is electrically connected on the upper section thereof to a circular plate form electrode film 26a that is provided on the flange 24, and it is electrically connected on the lower section thereof to an electrode film 26b that coats the outer bottom section of the reaction vessel 21. These electrode films 26a and 26b correspond to contact sections. As an example of the conductive thin film 26, for example, the conductive thin film shown in FIG. 1 (f) is used.

The supporting platform 27 that supports the reaction vessel 21 is larger than the outer diameter of the reaction chamber 22, and is provided with a vertical hole 18 that stores a reaction chamber 22 that has an inner diameter that is smaller than the outer diameter of the flange 24. The outer bottom section of the supporting platform 27 is provided with two pierced holes 27a and 27b along the axial direction of the supporting platform 27.

As shown in FIGS. 2 (c) and (d), rod shaped terminals 28a and 28b are provided on the upper side of the pierced holes 27a and 27b such that they protrude upwards from the upper side of the supporting platform 27. The rod shaped terminals 28a and 28b are connected through the lower side of the pierced holes 27a and 27b to the instruction section provided to the exterior, or to an information processing device or a power circuit serving as an electromagnetic supply section, via leads. Furthermore, a terminal block 27c that is energized upwards by a spring 29 is provided on the bottom of the vertical hole 28, and in a case where the reaction vessel 21 is inserted into the vertical hole 28, it makes contact with the electrode film 26b that coats the outside bottom section of the reaction vessel 21, and the electrode film 26a is positioned such that it makes contact with the electrodes 28a and 28b. Consequently, by flowing a predetermined electrical current between the electrode film 26a and the electrode film 26b, the conductive thin film 26 generates heat. Here, the electrode films 26a and 26b correspond to the contact sections.

Figure 3:
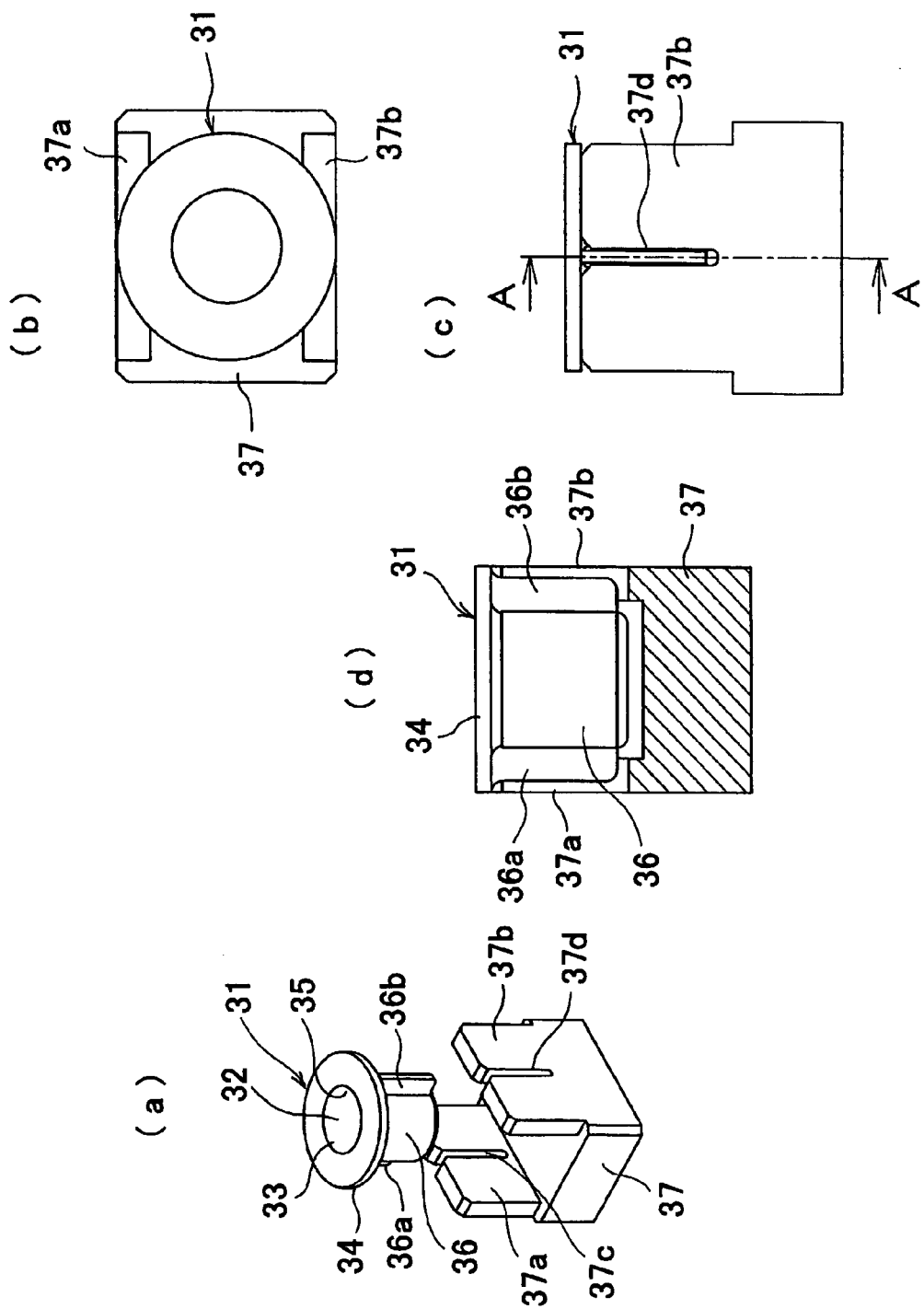
FIG. 3 is a drawing showing a reaction vessel according to a third embodiment of the present invention.

FIG. 3 (a) to (d) are a perspective view, a plan view, a side view and a cross-sectional view showing a reaction vessel 31 and a supporting platform 37 according to a third embodiment of the present invention. In FIG. 3 (a), the reaction vessel 31 comprises a reaction chamber 32 in which the liquid is storable, that is surrounded by an approximately cylindrical wall 35. Furthermore, to an opening part 33 on the upper section of the reaction chamber 32, a circular plate form flange 34 is provided such that it protrudes out on the side of the wall 35. Moreover, the outside face of the wall 35 is coated with a conductive thin film 36 as a temperature raising and lowering body, which has a predetermined resistance value, and on the outer face of the wall 35, protrusions are provided along the axial direction of the reaction vessel 31 in opposing positions that sandwich the central axis of the reaction vessel 31, which are coated by electrode films 36a and 36b, which are electrically connected to the conductive thin film 36. These electrode films 36a and 36b correspond to the contact sections. The conductive thin film 36 is, for example, the conductive thin film shown in FIG. 1 (f). By flowing a predetermined electrical signal, which is an electrical signal, through the electrode films 36a and 36b, the heat generation of the conductive thin film 36 is possible.

Regarding the supporting platform 37 that supports the reaction vessel 31, plate form terminals 37a and 37b in which grooves 37c and 37d are pierced along an axial direction in which the protrusions that coat the electrode films 36a and 36b are insertable, are provided in parallel at positions facing each other, at a spacing that is larger than the outer diameter of the reaction chamber 32 and smaller than the outer diameter of the flange 34. The height of the plate form terminals 37a and 37b is provided such that it is equal to the height of the reaction chamber 32, or slightly higher.

Figure 4:
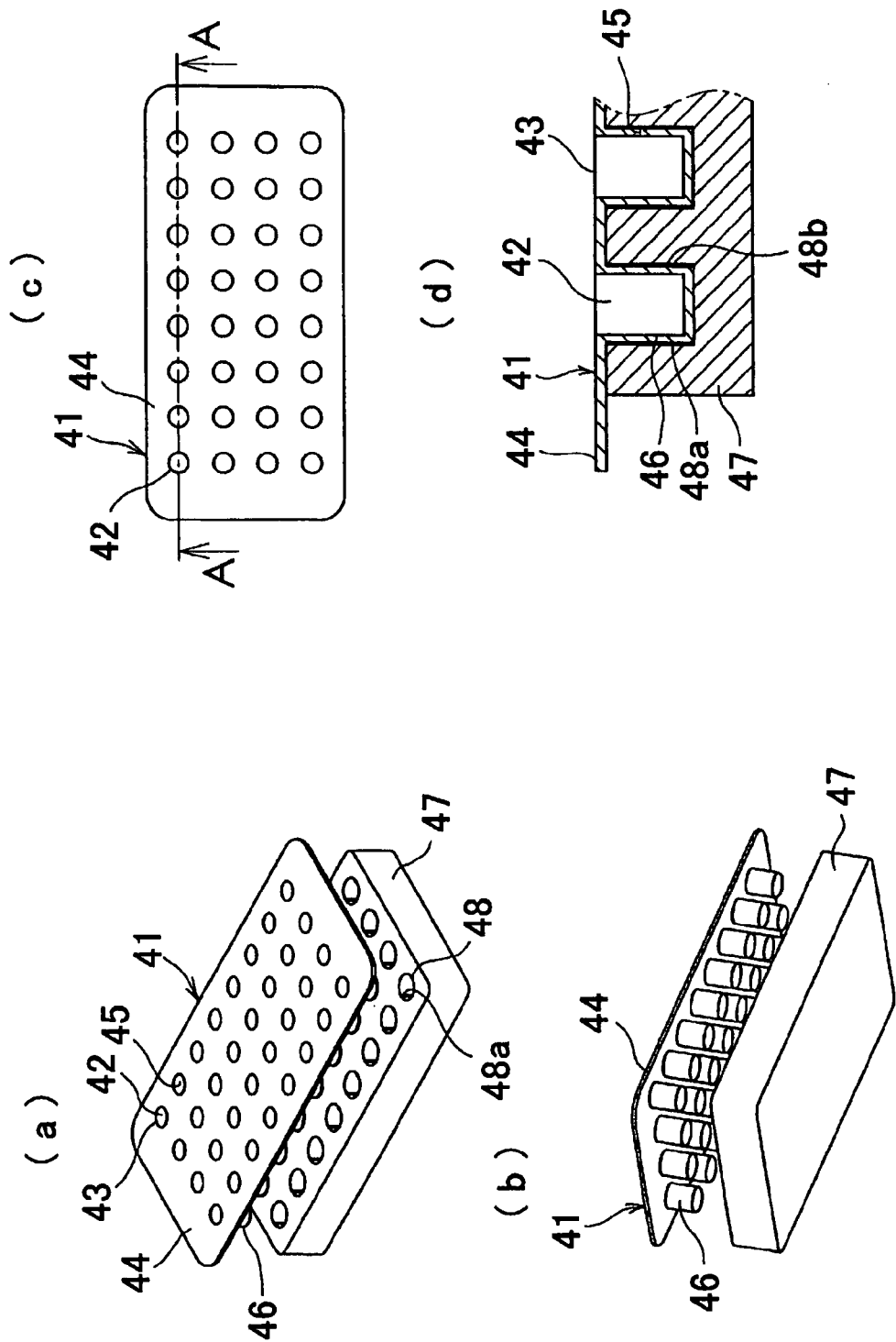
FIG. 4 is a drawing showing a reaction vessel according to a fourth embodiment of the present invention.

FIG. 4 is a perspective view from the upper side and the lower side, a plan view, and a side cross-sectional view showing a reaction vessel 41 and a supporting platform 47 that supports the reaction vessel 41 according to a fourth embodiment of the present invention. In FIGS. 4 (a) and (b), the reaction vessel 41 comprises a plurality of reaction chambers 42 in which the liquid is storable, that are surrounded by a cylindrical wall 45 and are provided such that they are arranged in a matrix form (in this example, four columns× eight rows) on a substrate 44. Opening parts 43 of the upper sections of the reaction chambers 42 are provided on the substrate 44. Furthermore, the outside face of the wall 45 is coated with a conductive thin film 46 as the temperature raising and lowering body, which has a predetermined resistance value. That is to say, the conductive thin film 46 is integrally provided to the wall 45. The conductive thin film 46 is, for example, the conductive thin film shown in FIG. 1 (f).

The supporting platform 47 that supports the reaction vessel 41 has a size in which the reaction chamber 42 is engagable, and a plurality of vertical holes 48 (in this example, four columns×eight rows), which are arranged in positions that correspond to the reaction chambers 42, are arranged in a matrix form. The vertical holes 48 are able to make contact with the conductive thin film 46, which coats the outside face of the wall 45 of the reaction chambers 42 of the reaction vessel 41 that has engaged the vertical hole 48, and a narrow and long film form terminal 48a along the axial direction thereof, and as shown in FIG. 4 (d), an additional film form terminal 48b that is provided in a state that is electrically separated from the film form terminal 48a, are provided on the inner wall face of the vertical hole 48. As a result of the film form terminals 48a and 48b making contact with the conductive thin film 46, and an electrical current with a predetermined electrical current value being flowed between the terminals from an information processing device or a power circuit, which is an instruction section, it is able to generate heat. Here, the contact section is the conductive thin film 46 itself.

Figure 5:
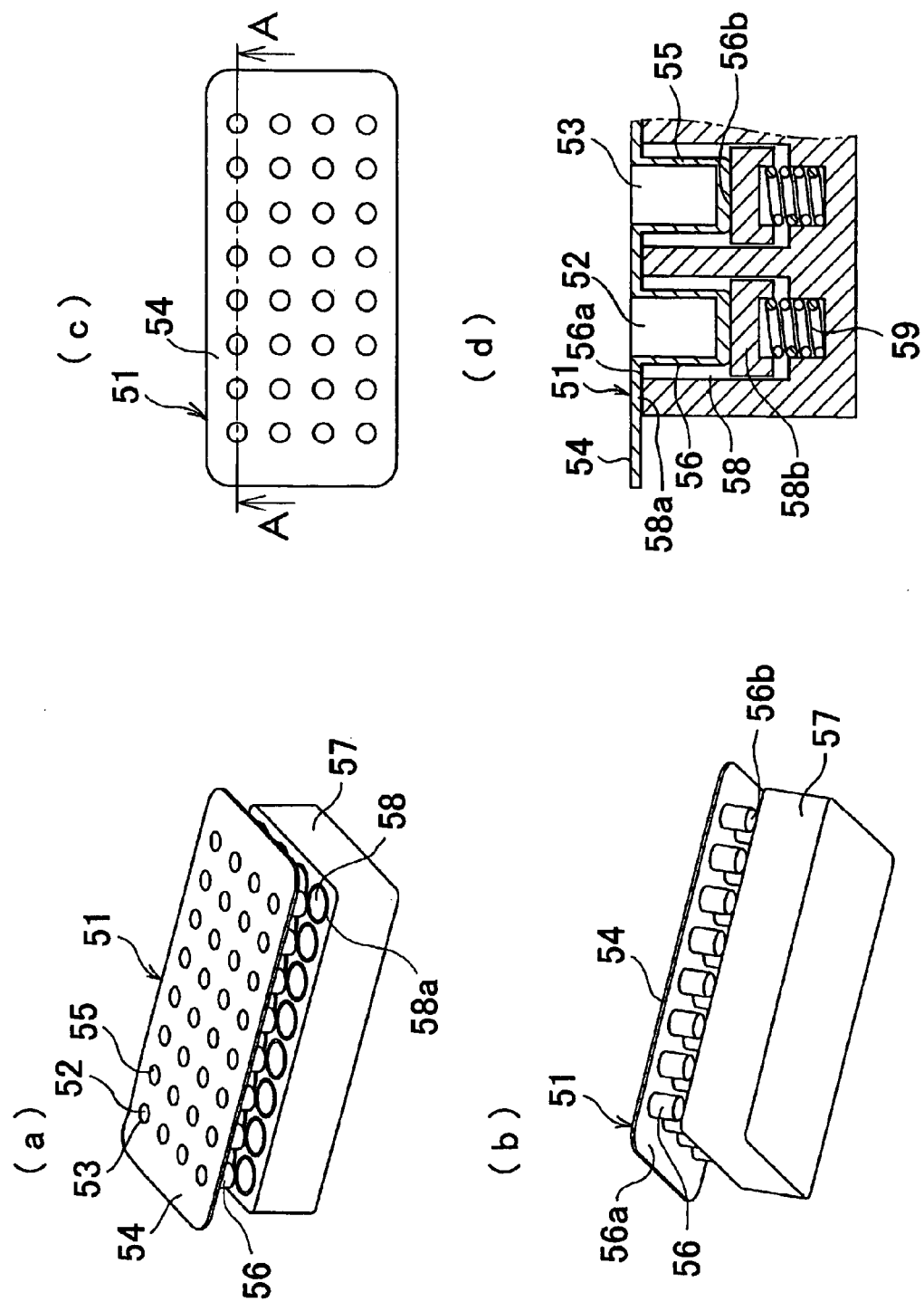
FIG. 5 is a drawing showing a reaction vessel according to a fifth embodiment of the present invention.

FIG. 5 is a perspective view from the upper side and the lower side, a plan view, and a cross-sectional view showing a reaction vessel 51 and a supporting platform 57 that supports the reaction vessel 51 according to a fifth embodiment of the present invention. In FIGS. 5 (a) and (b), the reaction vessel 51 comprises a plurality of reaction chambers 52 in which the liquid is storable, that are surrounded by a cylindrical wall 55 and are provided such that they are arranged in a matrix form (in this example, four columns×eight rows) on a substrate 54. Opening parts 53 of the upper sections of the reaction chambers 52 are provided on the substrate 54. Furthermore, the outside face of the wall 55 is coated with a conductive thin film 56 as the temperature raising and lowering body, which has a predetermined resistance value. That is to say, the conductive thin film 56 is integrally provided to the wall 55. Furthermore, the lower side (back side) of the substrate 54 of the reaction vessel 51 is coated with an electrode film 56a that is electrically connected to the conductive thin film 56, and the outer bottom section of the reaction chamber is coated with an electrode film 56b that is electrically connected to the conductive thin film 56.

The supporting platform 57 that supports the reaction vessel 51 has a size in which the reaction chamber 52 is insertable, and a plurality of vertical holes 58 (in this example, four columns×eight rows), which are arranged in positions that correspond to the reaction chambers 52, are arranged in a matrix form. In regard to the vertical holes 58, the opening part of the vertical hole 58 is provided with a film form electrode 58a that is able to make contact with the electrode film 56a of the reaction vessel 51 that has engaged the vertical hole 58, and furthermore, at the time of insertion of the reaction chamber 52 into the vertical hole 58, a terminal block 58b that is able to make contact with the electrode film 56b that coats the outer bottom section of the reaction chamber 52 is provided on the bottom of the vertical hole 58. Furthermore, the terminal block 58b is energized upwards by a spring 59, and the connection between the electrode film 56b of the reaction chamber 52 of the reaction vessel 51 and the terminal block 58b is made certain. The film form terminal 58a and the terminal block 58b are electrically connected to an information processing device or a power circuit, which is the instruction section or an electromagnetic supply section, and the electrode films 56a and 56b correspond to the contact sections.

Figure 6:
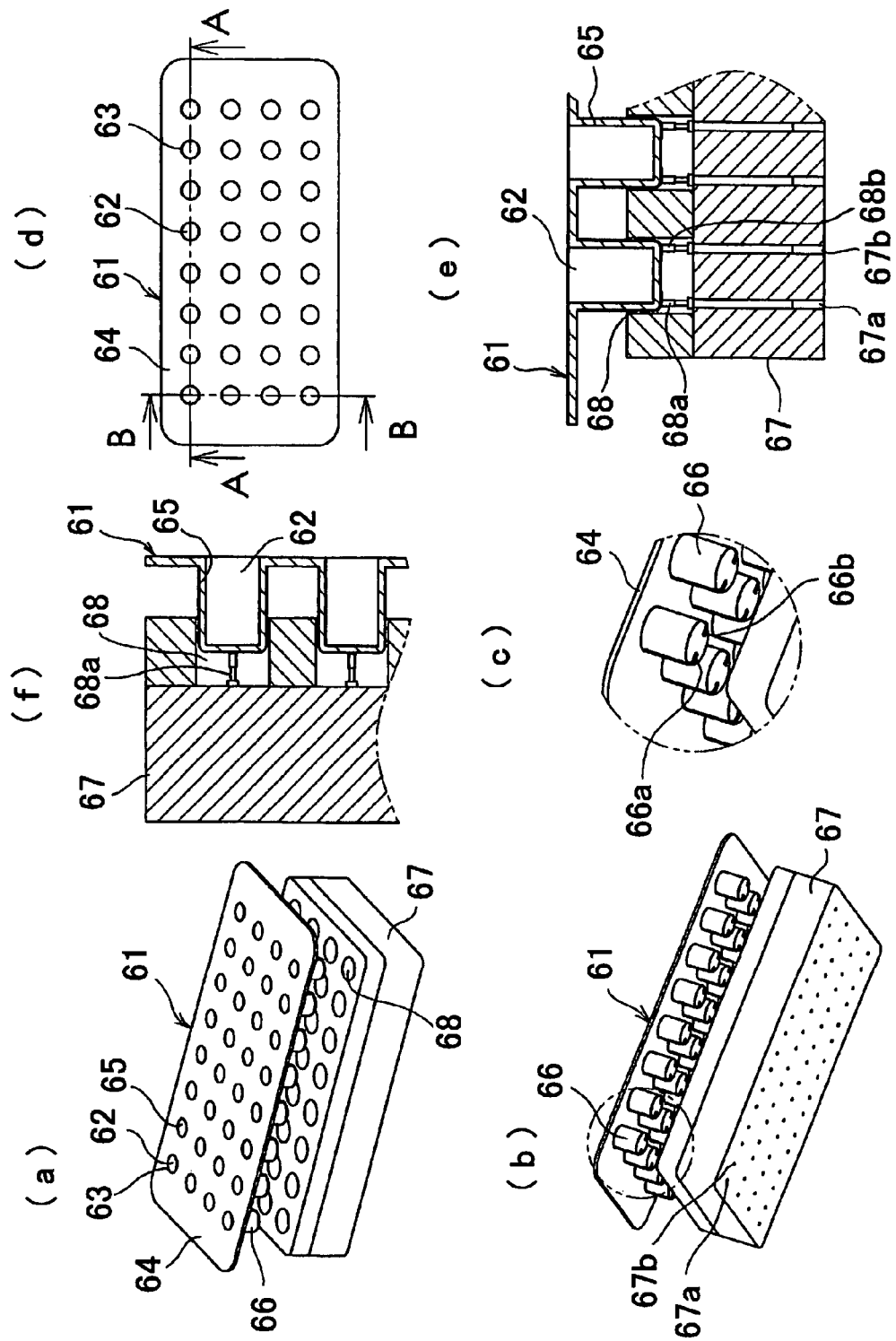
FIG. 6 is a drawing showing a reaction vessel according to a sixth embodiment of the present invention.

FIG. 6 is perspective views from the upper side and the lower side, a plan view, and corresponding cross-sectional views showing a reaction vessel 61 and a supporting platform 67 that supports the reaction vessel 61 according to a sixth embodiment of the present invention.

In FIGS. 6 (a) and (b), the reaction vessel 61 comprises a plurality of reaction chambers 62 in which the liquid is storable, that are surrounded by a cylindrical wall 65 and are provided such that they are arranged in a matrix form (in this example, four columns×eight rows) on a substrate 64. Opening parts 63 of the upper sections of the reaction chambers 62 are provided on the substrate 64. Furthermore, as shown enlarged in FIG. 6 (c), the outside face of the wall 65 is coated with a conductive thin film 66 as the temperature raising and lowering body, which has a predetermined resistance value. Moreover, the outside face of the wall 65 of the reaction chamber 62 is provided with two narrow film form electrode films 66a and 66b' in opposing positions sandwiching the central axis of the reaction chamber 62 along the axial direction of the reaction chamber 62 such that they reach the bottom face side of the reaction chamber 62 thereof, and are electrically connected to the conductive thin film 66. Here, the electrode films 66a and 66b correspond to the contact sections.

The supporting platform 67 that supports the reaction vessel 61 has a size to fit the reaction chamber 62, and a plurality of vertical holes 68 (in this example, four columns×eight rows), which are arranged in positions that correspond to the reaction chambers 62, are arranged in a matrix form. Furthermore, the regions of the bottom face of the supporting platform 67 that correspond to the vertical holes 68 are respectively provided with two pairs of pierced holes 67a and 67b.

Furthermore, as shown in FIGS. 6 (d), (e) and (f), terminals 68a and 68b are provided on the upper side of the pierced holes 67a and 67b such that they protrude upwards from the inner bottom section of the vertical hole 68. The terminals 68a and 68b are connected through the lower side of the pierced holes 67a and 67b to the instruction section provided to the exterior, or to an information processing device or a power circuit serving as an electromagnetic supply section, via leads. In a case where the reaction chambers 62 of the reaction vessel 61 have engaged the vertical holes 68, the terminals 68a and 68b are able to make contact with the electrode films 66a and 66b provided on the reaction chambers 62.

Figure 7:
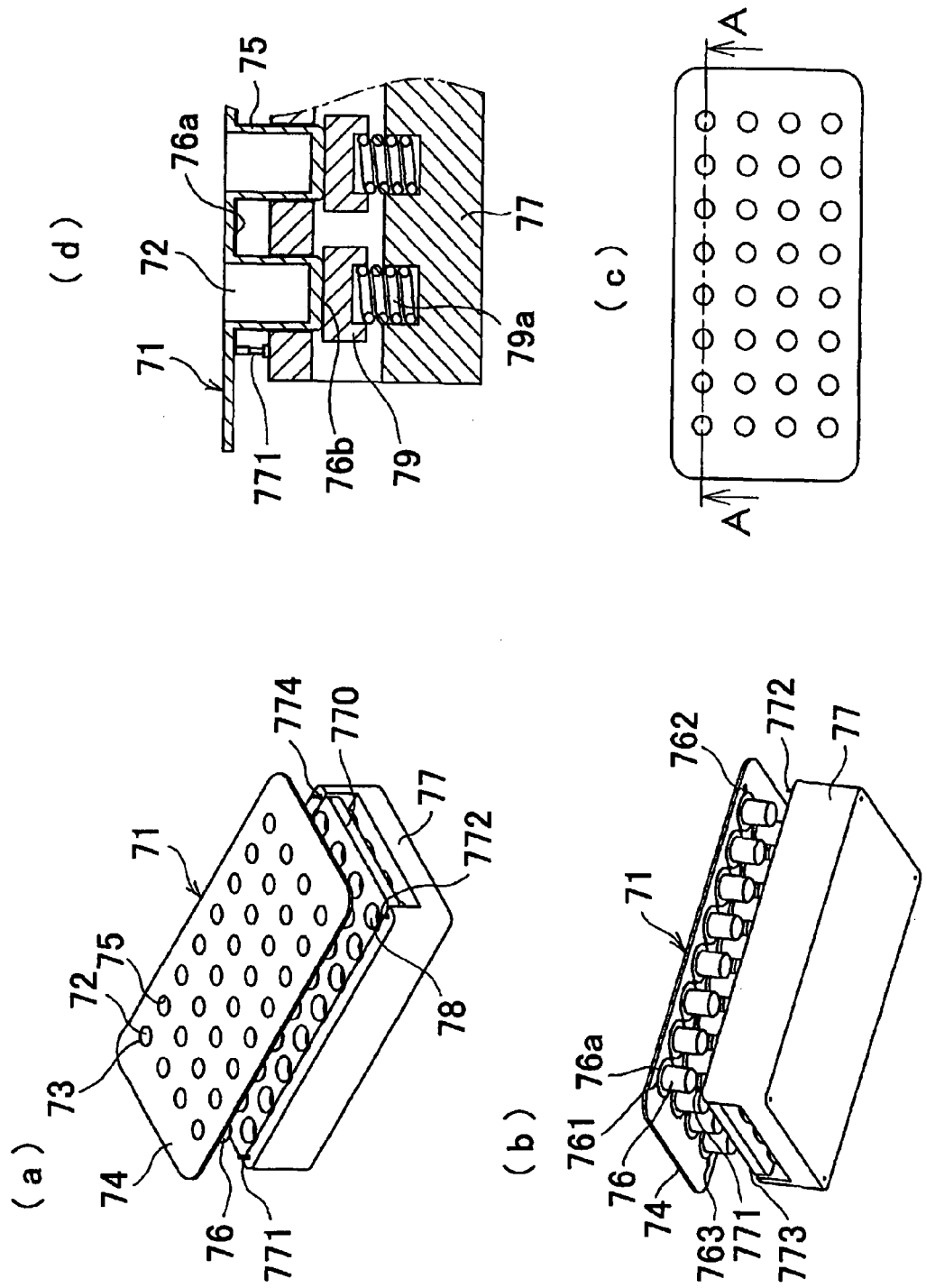
FIG. 7 is a drawing showing a reaction vessel according to a seventh embodiment of the present invention.

Moreover, FIG. 7 is a perspective view from the upper side and the lower side, a plan view, and a cross-sectional view showing a reaction vessel 71 and a supporting platform 77 that supports the reaction vessel 71 according to a seventh embodiment of the present invention.

In FIGS. 7 (a) and (b), the reaction vessel 71 comprises a plurality of reaction chambers 72 in which the liquid is storable, that are surrounded by a cylindrical wall 75 and are provided such that they are arranged in a matrix form (in this example, four columns×eight rows) on a substrate 74. Opening parts 73 of the upper sections of the reaction chambers 72 are provided on the substrate 74. Furthermore, the outside face of the reaction vessel 71 is coated with a conductive thin film 76, which is the temperature raising and lowering body, with a predetermined resistance value. Moreover, the lower side (back side) of the substrate 74 of the reaction vessel 71 is provided with the electrode film 76a, and the outer bottom face of the reaction chamber 72 is provided with the electrode film 76b, and they are respectively electrically connected to the conductive thin film 76.

The supporting platform 77 that supports the reaction vessel 71 has a size to fit the reaction chamber 72, and a positioning plate 770, in which a plurality of vertical holes 78 (in this example, four columns×eight rows) that are arranged in positions that correspond to the reaction chambers 62, are arranged in a matrix form, is supported by both side walls, which are provided such that they extend from both side edges of the supporting platform 77, and is positioned between the upper bottom face of the supporting platform 77 with a fixed spacing.

Four rod-shaped terminals 771 to 774 which are electrically connected to an instruction section, or an information processing device or a power circuit, which is an electromagnetic supply section, are provided for the four corners of the upper side face of both side walls such that they protrude upwards, and they are able to make contact with the four contact sections 761 to 764 that are provided such that they overlap the four corners of the electrode film 76a.

Furthermore, the supporting platform 77 is provided with terminal blocks 79, which are energized by springs 79a and are electrically connected with the power circuit, at positions that correspond to the vertical holes 78 of the positioning plate 770, and they are provided such that they are able to make contact with the electrode film 76b on the outer bottom face of the reaction chambers 72 that are supported by the supporting platform 77.

Figure 8:
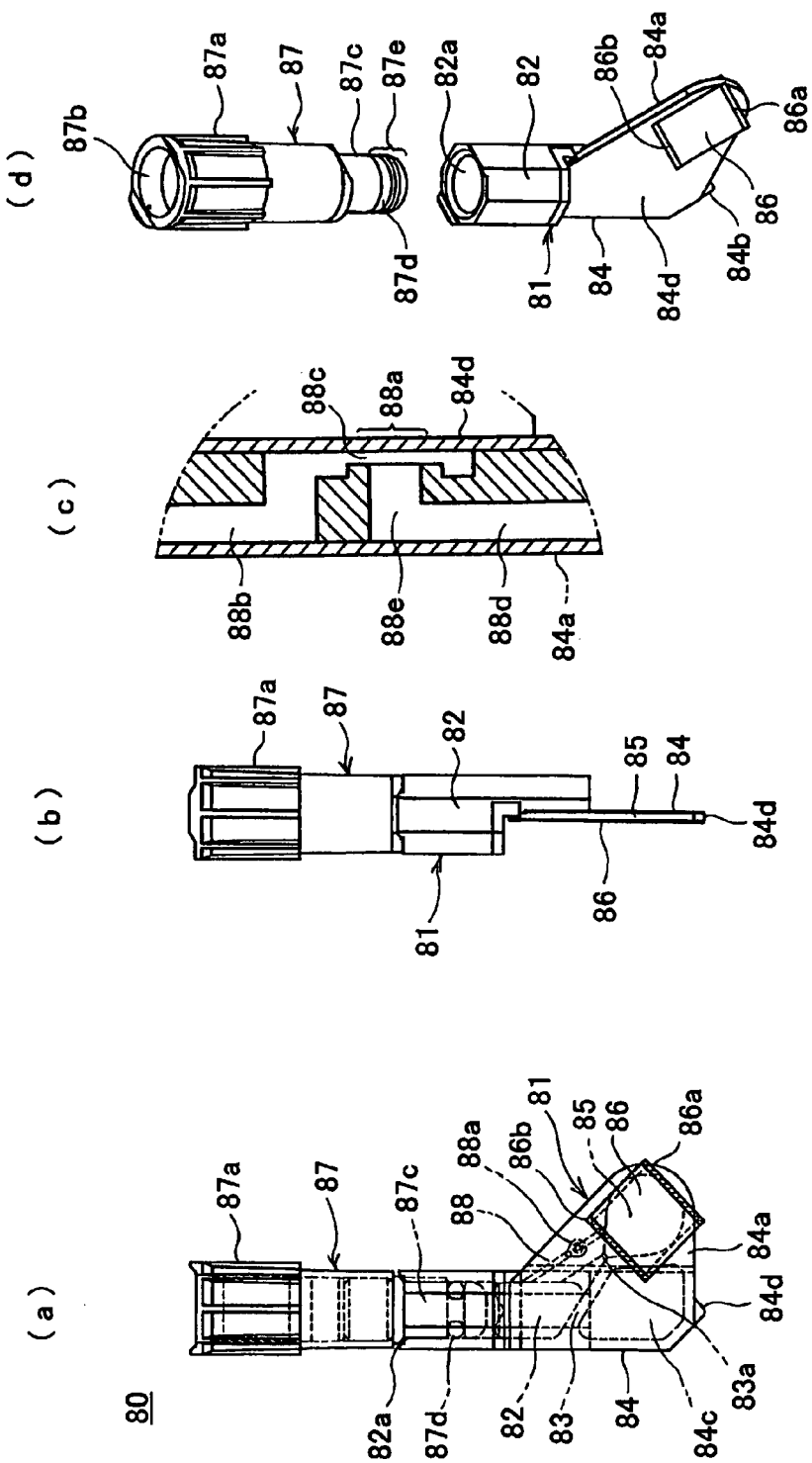
FIG. 8 is a drawing showing a reaction vessel and an installed cap according to an eighth embodiment of the present invention.

Next, a reaction vessel 81 according to an eighth embodiment of the present invention is explained based on FIG. 8. FIG. 8 (a) is a side view of a state where a cap 87 has been installed to the reaction vessel 81, and FIG. 8 (b) is a front view of a state where the cap 87 has been installed to the reaction vessel 81. Furthermore, FIG. 8 (c) is a partially expanded cross-sectional view of FIG. 8 (a), and FIG. 8 (d) is a perspective view showing a state where the cap 87 has been detached from the reaction vessel 81.

As shown in FIG. 8 (a) and FIG. 8 (b), the reaction vessel 81 comprises: an opening part 82a in the upper section; a cylindrical storage chamber 82 in which the liquid is storable; a reaction chamber 85 that is communicated with the storage chamber 82 via a liquid introduction flow passage 83 and a discharge flow passage 88 and is formed thinner than the storage chamber 82; the liquid introduction flow passage 83; and the discharge flow passage 88. The entirety of the liquid introduction flow passage 83, the discharge flow passage 88, and the reaction chamber 85 is formed in a thin plate form, and the entirety thereof is provided on a reaction section 84 that has translucency. The opening part 82a is installable by engaging insertion of the cap 87, and the cap is further installable by threading to a nozzle 222 mentioned below, which is a rotating body. That is to say, the opening part 82a is installable to the nozzle 222 via the cap 87. That is to say, the reaction vessel 81, as a liquid introducing mechanism that introduces the liquid into the reaction chamber 85, uses a rotating body and introduces the liquid by applying a centrifugal force.

The reaction chamber 85 is on the underside of the storage chamber 82, and with respect to the axis of the opening part 82a or the storage chamber 82, it is provided in a position farther away than the storage chamber 82 in terms of the position coordinate of the center of gravity of the chambers. When the reaction vessel 81 is installed on the nozzle 222 mentioned below, serving as a rotating body, the axis of the opening part 82a or the storage chamber 82 matches the rotation axis of the rotating body.

Accordingly, in a case where the rotating body is rotated, a centrifugal force is applied to the liquid within the storage chamber 82, and the liquid is introduced into the reaction chamber 85, which is in a position farther away than the rotation axis, via the flow passage 83, and the air that is stored in the reaction chamber 85, or a portion of the introduced liquid returns to the storage chamber 82 via the discharge flow passage 88. The reaction chamber 85, the liquid introduction flow passage 83, and the discharge flow passage 88 are provided in a planar frame 84a to which bottomed grooves have been formed, and in regard to one facial side of the frame 84a, as well as being sealed by a flexible film form member 84d mentioned below, it is coated with a conductive thin film 86, which serves as a temperature raising and lowering body, with a predetermined resistance value. The liquid introduction flow passage 83 has an entrance at a bottom face not of the storage chamber 82, and has an exit at the upper section of the reaction chamber 85, and the discharge flow passage 88 has an entrance at the upper side of the reaction chamber 85 and has an exit at the inner side face of the storage chamber 82, and communicates between the reaction chamber 85 and the storage chamber 82. Here, examples of the flexible film form member include polyethylene or silicone, which are easily deformed by pressing.

The width of the liquid introduction flow passage 83 becomes shortest at the lower side near the reaction chamber 85, and a blocking section 83a that blocks the flow passage 83 by pressing the film form member 84d is provided at the position thereof. Furthermore, as shown in FIG. 8 (c), a hole section 88e, which is communicated with the flow passage 88d from the reaction chamber 85, and that protrudes in the film form member 84d direction within the space between the frame 84a and the film form member 84d, is provided in the middle of the discharge flow passage 88 between the film form member 84d with a spacing 88c, and is communicated only through the flow passage 88b from the storage chamber 82 and the spacing 88c. This portion corresponds to a blocking section 88a that is able to block the discharge flow passage 88 by pressing the film form member 84d from the exterior thereof.

Furthermore, outer surface of the film form member 84*d* is coated with a conductive thin film 86 with a predetermined resistance value, which serves as the temperature raising and lowering body, by means of adhesion, pasting, welding, deposition and the like, such that it approximately covers the reaction chamber 85. Electrode films 86*a* and 86*b* are provided for the two opposing end sections of the conductive thin film 86, and they are able to make contact with terminals that are connected to an instruction section, or an information processing device or an electronic circuit, which is an electromagnetic supply section, that is not shown in the drawing. The terminals are provided such that they are able to approach and separate with respect to the electrode films 86*a* and 86*b*. The electrode films 86*a* and 86*b* correspond to the contact sections.

As shown in FIG. 8 (*d*), the reaction vessel 81 is installed to the cap 87 at the opening part 82*a* thereof by means of freely detachable engagement. The cap 87 comprises an engaging section 87*c* that is engagable with the opening part 82*a* that is on the lower end thereof, and a locking rim 87*e* and an O ring 87*d* are provided in the vicinity of the end of the engaging section 87*c*. Furthermore, the opening part of the upper end section of the cap 87 is a nozzle engaging section 87*b* that engages the nozzle 222. Moreover, a plurality of protrusions 87*a* are provided on the upper side of the outside face of the cap 87, which are engagable with cap engaging sections 247*a* and 247*b* mentioned below, and as a result, the automatic detachment of the cap 87 becomes possible.

In FIG. 8(*d*) reference symbol 84*d* denotes a rotation supporting axle that is provided in a position along the axis of the opening part 82*a*, and at the time the reaction vessel 81 is rotated, the rotation supporting axle is journaled, and it serves to smoothly perform the rotation by preventing core deviations at the time of rotation. Reference symbol 84*c* denotes a depression formed on the frame 84*a*.

As shown in FIG. 8 (*a*), the reaction chamber 85 is formed in a thin cylindrical shape. The reaction chamber 85 is surrounded by two bottom faces and one side face, and the bottom area is formed larger than the side area. At the time of reaction, there is a need for movable pressing sections that press from the exterior of the film form member 84*d*, to be provided at the blocking section 83*a* and the blocking section 88*a* on the exterior of the large wall face on which this film form member 84*d* is formed. On the wall face of the opposite side thereof, is positioned an irradiation end section which is the end of an optical fiber, a lens, or the like, that irradiates light from a trigger light source which generates excitation light. These pressing sections and the irradiation end section are provided such that they are able to approach and separate with respect to the large wall face of the reaction chamber 85. At the blocking section 83*a* there may be provided an elastic valve (for example, reference symbols 95 and 96 in FIG. 9 (*c*)) which is formed from an elastic body, that is formed by a hole section through which the liquid or gas is passable and a void that is communicated with the hole section, that is blockable by pressing the void and blocking the void.

Figure 9:
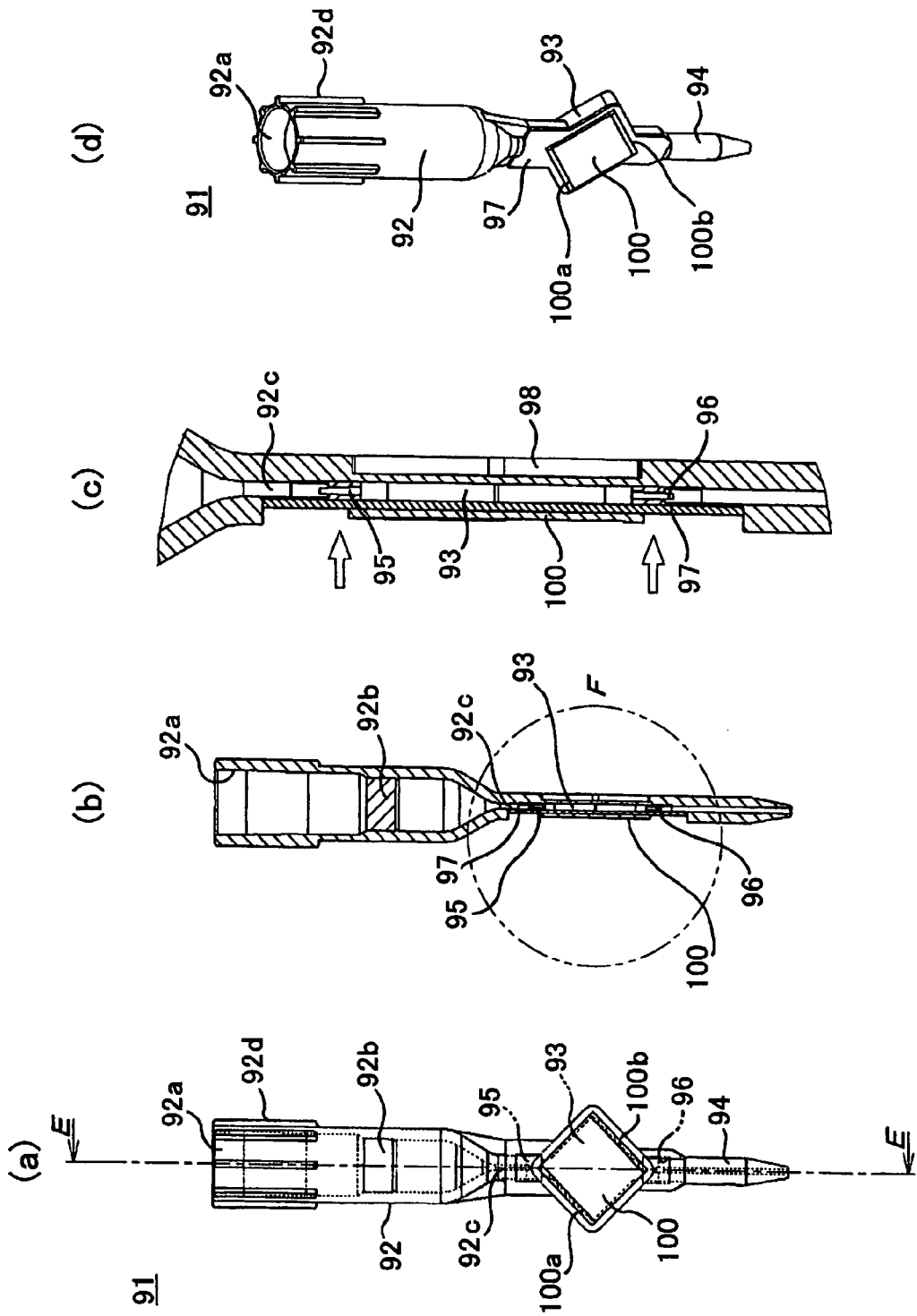
FIG. 9 is a drawing showing a reaction vessel according to a ninth embodiment of the present invention.
Figure 10:
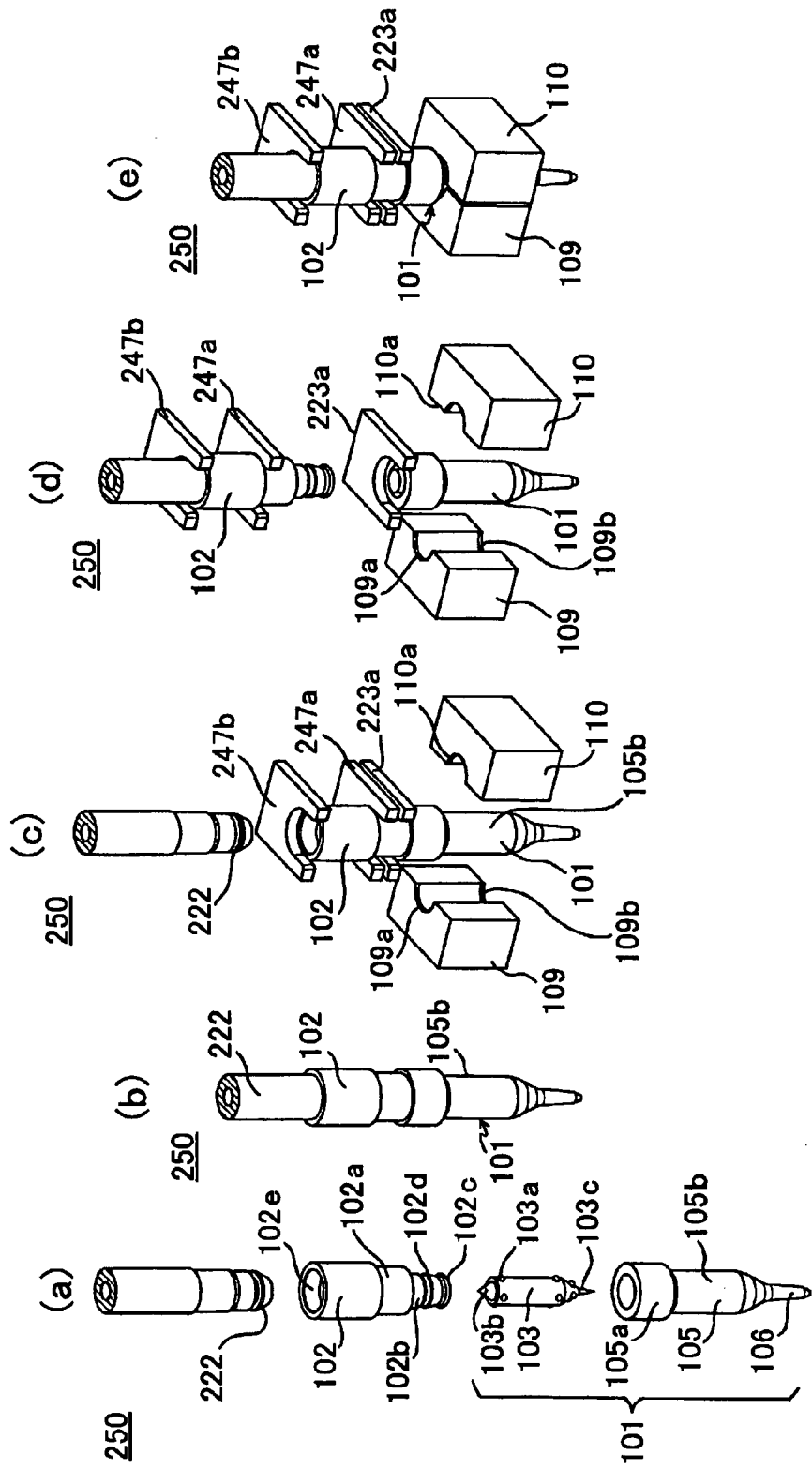
FIG. 10 is a drawing showing a reaction vessel and an installed cap according to a tenth embodiment of the present invention.
Figure 11:
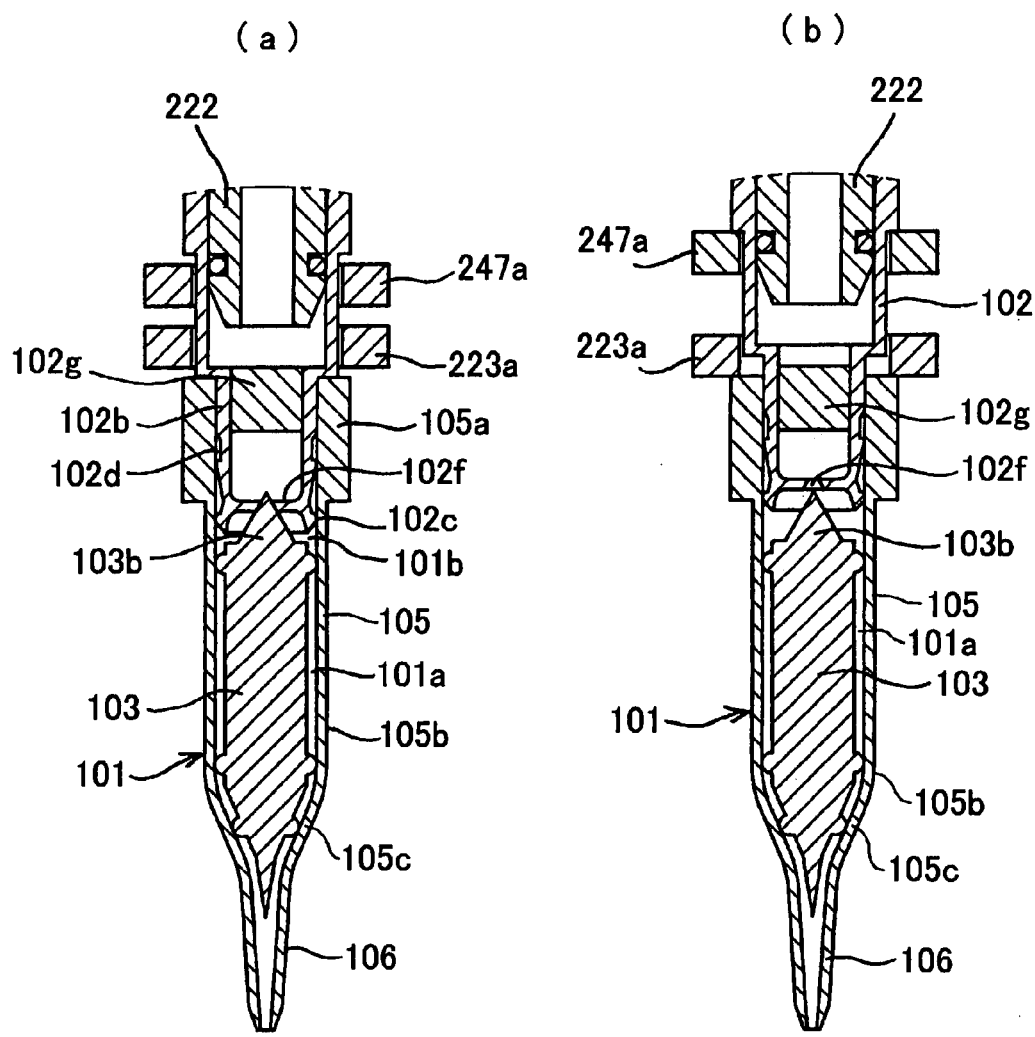
FIG. 11 is a cross-sectional view of the reaction vessel shown in FIG. 10.

Next, a reaction vessel that belongs in a category that introduces the liquid by the suction and discharging of a nozzle, is explained based on FIG. 9 to FIG. 11.

FIG. 9 shows a reaction vessel 91 according to a ninth embodiment. FIG. 9 (*d*) shows a perspective view of the reaction vessel 91, FIG. 9 (*a*) is a front view thereof, FIG. 9 (*b*) is a cross-sectional side view thereof, and FIG. 9 (*c*) is an enlarged cross-sectional view of region F shown in FIG. 9(*b*).

The reaction vessel 91 comprises a cylindrical storage chamber 92 that has a thick diameter, a diamond-shaped prismatic reaction chamber 93 that is formed thinner than the storage chamber 92, and a thin diameter section 94 provided on the lower side of the reaction chamber 93 that is formed thinner than the cylinder.

An interval between the storage chamber 92 and the reaction chamber 93, and an interval between the reaction chamber 93 and the exterior, are connected by flow passages 92*c*, and a thin diameter section 94. Furthermore, the flow passage 92*c* and the thin diameter section 94 are provided with elastic valves serving as blocking sections 95 and 96 that are blockable as a result of pressing.

In regard to the storage chamber 92, a nozzle not shown in the drawing is installable to the opening part 92*a* thereof by engagement, and in the interior of the storage chamber 92 and on the lower side of the installation portion of the nozzle, for example, a heat insulating filter 92*b* is provided so as to partition the storage chamber 92. Consequently, the heating and cooling effects towards the reaction chamber 93 can be increased. Furthermore, the lower side of the storage chamber 92 is formed such that it becomes thinner at the end, and is communicated with the flow passage 92*c*. Furthermore, a plurality of protuberances 92*d* are provided on the outer face of the storage chamber 92, and by means of the protuberances 92*d*, it becomes automatically removable as a result of a tip removal plate 93*a* mentioned below.

One of the large walls of the reaction chamber 93 is lined with a film 97 that is formed from a soft material that is deformable by means of pressing, and in regard to the other large wall, as well as it being formed by the frame of the reaction vessel 91, a depression 98 that covers the reaction chamber 93 is provided on the frame in order to increase the thermal conductivity, and it is thinly formed. Moreover, on the outside of the film 97 is provided by adhesion, pasting, welding, or deposition, a diamond-shaped conductive thin film 100 having a predetermined resistance value as a temperature raising and lowering body, and on opposite edges facing the conductive thin film 100 is provided long and narrow shape electrode films 100*a* and 100*b*. As a result, by flowing a predetermined current between the electrode films 100*a* and 100*b*, and heating, the inside of the reaction chamber 93 can be efficiently heated.

For the blocking sections 95 and 96, there may be provided for example as mentioned before, elastic valves having a hole section, and a void that is blockable by means of pressing.

FIG. 10 is a tip-shaped reaction vessel 101 according to a tenth embodiment, and shows a cap 102 through which passage of fluid is possible, and a reaction vessel installation portion in which the tip-shaped reaction vessel 101 is installed to the nozzle 222 of the liquid introducing device 250, which is also a rotatable and vertically and horizontally movable reaction vessel liquid introducing device.

FIG. 10 (*a*) is a disassembled perspective view of the reaction vessel installation portion of the liquid introducing device 250, and FIG. 10 (*b*) shows the reaction vessel installation portion of the liquid introducing device 250.

As shown in FIG. 10 (*a*), the tip-shaped reaction vessel 101 comprises; a cylindrical thick diameter section 105, a thin diameter section 106 that is provided on the lower side of the thick diameter section 105 and that is formed thinner than the thick diameter section 105, an opening part 105*a* that is provided on the upper side of the thick diameter section 105, has an outer diameter even thicker than the thick diameter section 105, and in which the end section 102*a* of the cap 102 is engagingly insertable, and a cylindrical core 103 that is stored between the thick diameter section 105 and the thin diameter section 106. A plurality of protrusion sections 103*a* are provided on the outer circumferential face of the core 103 such that they protrude in the outer direction as spacers for creating a space between the stored core and the inner circumferential face of the thick diameter section 105 or the thin diameter section 106. The space between the outer circumferential face of this core 103 and the inner circumferential face of the thick diameter section 105 corresponds to the reaction chamber. Furthermore, the space above the core 103 on the upper side of the thick diameter section 105 corresponds to the storage chamber.

Moreover, the lower end of the core 103 is formed matching the shape of the thin diameter section 106 such that it becomes thinner at the end, and the upper end of the core 103 comprises a blocking section 103b that can disable the passage of fluid by blocking the end section 102a of the cap 102. In this example, the blocking section 103b is formed in a conical shape corresponding to a hole section 102f (refer to FIG. 8) provided on the end section 102a of the cap 102, that expands in the outer direction.

Furthermore, the cap 102 is an entirely hollow approximately cylindrical shape, and it comprises a base section 102b, an end section 102b that has an outer diameter that is formed narrower than the outer diameter of the base section 102a, and an engaging section 102e that has a thicker outer diameter than the outer diameter of the base section 102a to which the end of the nozzle 222 is engagable. A rim 102c that adheres to the inner face of the opening part 105a of the reaction vessel 101, and an annular groove 102d, are provided on the end section 102b.

Moreover, the outside face of the thick diameter section 105 is coated by adhesion, pasting, welding, or deposition, a conductive thin film 105b as a temperature raising and lowering body. As a result, the reaction chamber provided inside the thick diameter section 105 can be heated.

FIGS. 10 (c), (d), and (e) show a terminal blocks 109 and 110 that are electrically contacted with the conductive thin film 105b serving as the temperature raising and lowering body, coated on the outside surface of the tip-shaped reaction vessel 101, and that are connected to an information processing device or a power circuit, or the like, for supplying a current for heating the conductive thin film 105b. Here the contact section is the conductive thin film 105b. Regarding the heating and cooling, the tip-shaped reaction vessel 101 is moved using the liquid introducing device 250 in a condition with the nozzle 22 fitted, as far as the region where the terminal blocks 109 and 110 are provided, and detachment from and installation to the liquid introducing device 250 is performed with respect to the tip-shaped reaction vessel 101.

The liquid introducing device 250 comprises a tip removal plate 223a for stripping the tip-shaped reaction vessel 101, that has a pierced semicircular notch that is somewhat smaller than the outer diameter of the opening part 105a, and is larger than the outer diameter of the base section 102a of the cap 102. The tip removal plate 223a is movably provided in the vertical direction, and approachably and separatably provided with respect to the reaction vessel 101, and consequently the axis of the nozzle 222. Furthermore, cap engaging sections 247a and 247b that are engagable to the stepped portion of the engaging section 102e of the cap 102, are provided for the liquid introducing device 250 such that they sandwich the engaging section 102e of the cap 102 from above and below. The cap engaging section 247a of the lower side has a semicircular notch that is larger than the outer diameter of the base section 102a of the cap 102 and is smaller than the engaging section 102e, and the cap engaging section 107b of the upper side has a semicircular notch that is larger than the outer diameter of the nozzle 222 and is smaller than the outer diameter of the engaging section 102e. Furthermore, the distance between the cap engaging section 247a of the upper side and the cap engaging section 247b of the lower side is fixed, and these cap engaging sections 247a and 247b are not only vertically movably provided, but also approachably and separatably provided with respect to the axis of the nozzle 222.

FIG. 10 (c) shows a state in which by simultaneously lowering the cap engaging sections 247a and 247b, and the tip removal plate 223a to the lower side, the tip-shaped reaction vessel 101 to which the cap 102 is installed is removed from the nozzle 222, and the thick diameter section 105 of the reaction vessel 101 is supported in a position sandwiched by the terminal blocks 249a and 249b, and current is supplied to the conductive thin film 105b.

FIG. 10 (d) shows a state in which only the tip removal plate 223a is lowered in a state where the cap 102 is installed to the nozzle 222, and the reaction vessel 101 has been removed from the cap 102.

FIG. 10 (e) shows a state in which the reaction vessel 101 is sandwiched by the terminal blocks 249a and 249b in a state where the reaction vessel 41 has been installed to the nozzle 222 via the cap 102. A predetermined variety of biological materials are arranged in predetermined position coordinates on the outer peripheral surface of the core 103, assigned to the positions by a predetermined relationship. Then the suction mechanism of the nozzle 222 is used to introduce the liquid in which the labeled biological material is suspended into the large diameter section 105, and the reaction is promoted by means of the temperature raising and lowering body, and by measuring the luminescent state of the labeling material from the exterior, this can be used in analysis of the presence, the structure, and the character of the biological material.

As shown in the cross-sectional view of the reaction vessel 101 in FIG. 11 (a), the gap section 101a enclosed by the outer face of the core 103 and the inner face of the wall 105c of the thick diameter section 105 corresponds to the reaction chamber, and the space section 101b formed on the upper portion of the core 103 at the upper side of the thick diameter section 105 corresponds to the storage chamber. The conductive thin film 105b is provided so as to coat the outer face of the wall 105c. Furthermore, the hole section 102f, that has a shape that is blockable by means of the blocking section 103b of the core 103, is pierced through the end section 102b of the cap 102. The hole section 102f is blocked by the blocking section 103b in a state where the end section 102b is most deeply inserted into the opening part 105a of the reaction vessel 101. A heat insulating filter 102g is provided on the upper side of the interior of the end section 102b, and the transmission of heat from the reaction chamber to the nozzle 222 is prevented.

In FIG. 11 (b), by moving the end section 102b of the cap 102 and the cap engaging sections 247a and 247b in the upper direction, they are hooked onto the engaging section 102e of the cap 102, and the cap 102 is somewhat moved in the upper direction. Then, the blocking section 103b of the core 103 is removed from the hole section 102f, and the nozzle 222 is communicated with the reaction vessel 101 via the heat insulating filter 102g of the cap 102. Consequently, the thin diameter section 106 of the reaction vessel 101 is inserted into the vessel in which liquid has been stored, and by performing suction of gas by means of the nozzle 222 in a state where the position of the cap 102 is such that the hole section 102f is opened, the liquid is introduced to the space section 101b through the thin diameter section 106 of the reaction vessel 101 and the gap section 101a. Thereafter, it is made a state where the end section 102b of the cap 102 is most deeply inserted into the opening part 105a of the reaction vessel, and as well as the hole section 102f being blocked by the blocking section 103b, as a result of the end of the thin diameter section 106 being inserted into and engaging another cap that is not shown in the drawing, it is possible for liquid to be sealed within the gap section 101a.

Figure 12:
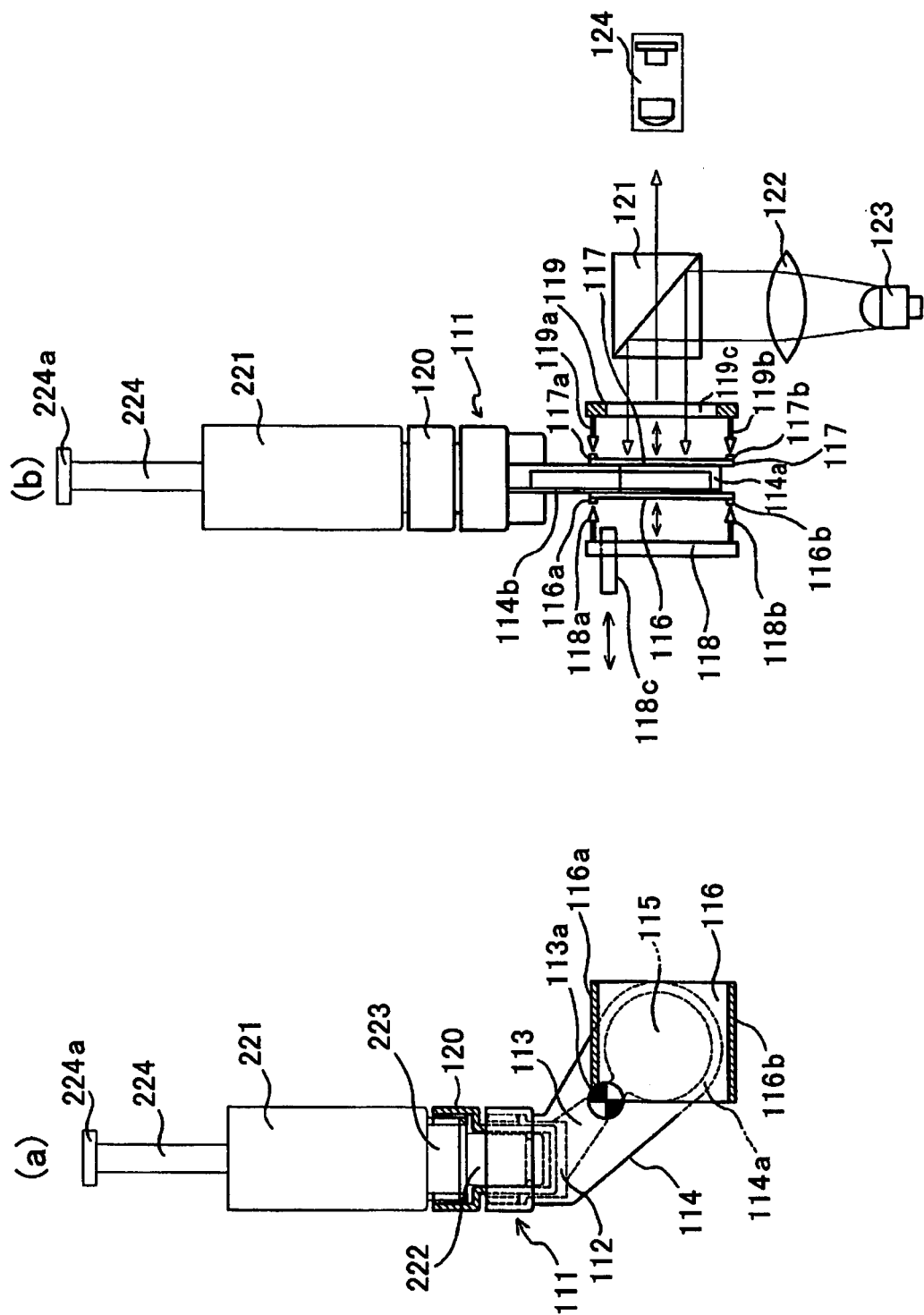
FIG. 12 is a drawing showing a reaction vessel according to an eleventh embodiment of the present invention, and where reaction measurement is to be performed.

Next, based on FIG. 12, a reaction vessel 111 according to an eleventh aspect of the invention is installed to the lower end section of the nozzle 222, which serves as the rotating body of the liquid introducing device 250, via a cap 120, and in a case where it has been transported to the reaction measurement position by the liquid introducing device 250, it has: a lens 122 and an excitation trigger light source 123 serving as the irradiation end section of the optical information measurement section; a light receiving optical system 124 that includes a light receiving end section that has an optical system such as a lens, a light distribution device, or a filter; and a half mirror 121 that, with respect to the reaction vessel 111, irradiates the light from the irradiation end section, and serves to guide the light from the reaction vessel 111 to the light receiving end section.

FIG. 12 (a) is a side view showing the reaction vessel 111. The reaction vessel 111 comprises: a storage chamber in which a liquid is storable, that has an opening part, an approximately thin cylindrical shaped reaction chamber that is communicated with the storage chamber 112 and is formed thinner than the storage chamber 112, and an introduction flow passage 113 that communicates between the storage chamber 112 and the reaction chamber 115. The reaction chamber 115 is consequently surrounded by two circular large bottom faces of a large area and one side wall face of a small area. The introduction flow passage 113 and the reaction chamber 115 is formed in a layer form such that they sandwich the same, and the entirety thereof is provided in a translucent reaction section 114. In this example, the introduction flow passage 113 and the reaction section 114 are formed in a bottomed planar frame 114a, and the opening side of the frame 114a is covered by a flexible thin film 114b. Furthermore, on the two large bottom face sides of the reaction chamber 115, two rectangular shaped conductive thin films 116 and 117, which have a predetermined resistance value and serve as temperature raising and lowering bodies, and have a size that covers the reaction chamber 115 and a predetermined resistance value, are provided by adhesion, pasting, welding, or deposition, and the two opposing edges of the conductive thin films 116 and 117 are provided with electrode films 116a, 116b, 117a and 117b as the contact sections. In the drawing, reference symbol 113a is a blocking section that can block the introduction flow passage 113 by means of pressing.

As shown in FIG. 12 (b), as well as the exterior of the conductive thin films 116 and 117 being provided with terminals 118a, 118b, 119a and 119b such that they protrude out and are respectively able to make contact with the electrode films 116a, 116b, 117a and 117b, these terminals are electrically connected to an information processing device or a power circuit that serves as the instruction section or the electromagnetic supply section. They are provided to movement plates 118 and 119 that are provided such that they can approach and separate with respect to the reaction vessel 111. Furthermore, the movement plate 118 comprises a pressing section 118c that is further movable with respect to the movement plate 118 in order to block the blocking section 113a. Moreover, in regard to the movement plate 119, the central portion 119c is transparent, or is provided with a hole, in order to make irradiation and reception of light possible with respect to the reaction chamber 115.

In regard to the reaction vessel 111, as the rotating body of the liquid introducing device 250, suction and discharge of the fluid is possible, and the inner surface of the upper side of the cap 120 is threaded with the outer surface of the threaded section 223 of a nozzle 222, which is rotatable about the axis thereof, such that it covers the lower end section of the nozzle 222. As a result, contact between the nozzle 222 and the reaction vessel 111 that is to be installed, or with the stored liquid thereof, can be prevented. The outer surface of the cap 120 is threaded, and by threading with the inner surface of the opening part of the reaction vessel 111, the reaction vessel 111 is installed to the nozzle 222. A cylinder (not shown in the drawing) which is communicated with the nozzle 222 and is rotatably provided together with the nozzle 222, is provided on the inner section of the cylindrical element 221, and is rotatably supported on the cylindrical element 221 via a bearing (not shown in the drawing). In order to perform fluid suction and discharging of the nozzle 222, a rod 224 which vertically moves a plunger (not shown in the drawing) that adjusts the pressure within the nozzle 222, is provided within the cylinder. On the upper end of the rod 224, an end section 224a which has a larger diameter than the diameter of the rod 224, is provided. The rod 224 that has been inserted into the rotatable cylinder, is non-rotatably provided in the nozzle 222 or the cylinder.

In this manner, in the present embodiment, the interval between the threaded section 223 and the cap 120, and the interval between the cap 120 and the opening part of the reaction vessel 111 is connected as a result of threading. Accordingly, it is necessary to thread the threaded portion in the tightening direction by rotation of the nozzle 222 serving as the rotating body.

According to the reaction vessel 111 of the present embodiment, the reaction chamber 115 is provided on the lower side of the storage chamber 112 in a position farther away from the rotation axis than the storage chamber 112, that is to say, the axis of the opening part. Consequently, the liquid that is dispensed into the storage chamber 112 by the dispensing tip by means of the suction and discharging of the nozzle 222, can be introduced into the reaction chamber 115 by the nozzle 222 rotating about the axis thereof, as a result of centrifugal force. When the liquid is introduced into the reaction chamber 115, the air that is present within the reaction chamber 115 is discharged to within the storage chamber 112 through the discharge flow passage 113, and in a case where the reaction chamber 115 is filled with the liquid, the reaction chamber 115 is sealed by pressing the blocking section 113a with the pressing section 118c.

As shown in FIG. 12, the light receiving optical system 124 that includes the conductive thin films 116 and 117 which serve as temperature raising and lowering bodies, and the lens 122 and the like which serves as the irradiation end section, are provided for two circular large wall faces of the reaction chamber 115 that have a large area. Accordingly, as well as being able to efficiently and quickly perform heating and cooling, a sufficient amount of excitation light is irradiated, and furthermore, a sufficient quantity of light can be obtained. Moreover, since the irradiation and reception of light is performed by the same wall face, the device scale can be compactly formed.

Figure 13:
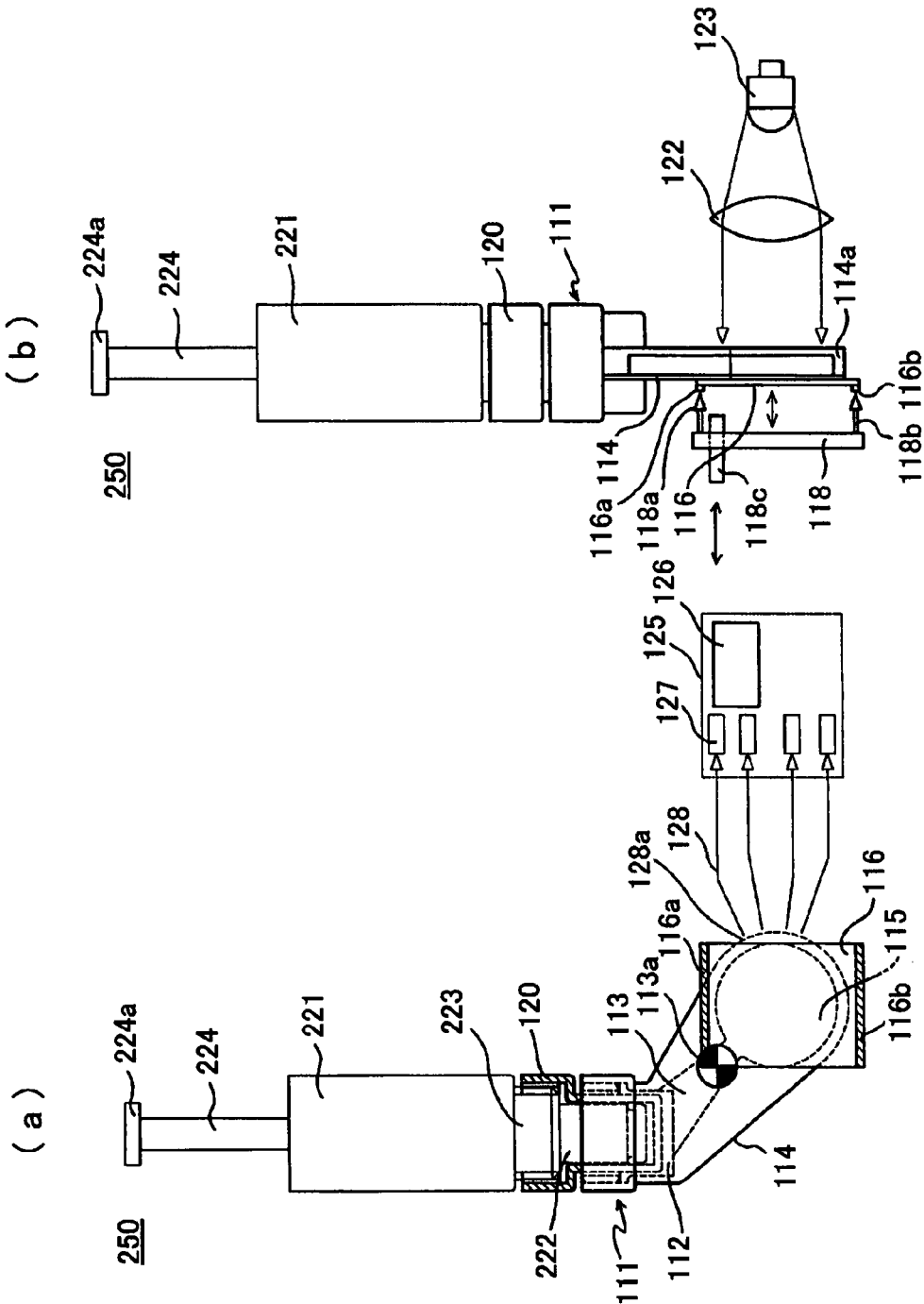
FIG. 13 is a drawing showing where the reaction vessel shown n FIG. 12 uses another optical information measuring device to perform reaction measurement.

In FIG. 13, the reaction vessel 111 has been applied to an optical information measurement section according to another example.

In regard to the optical information measurement section, as shown in FIG. 13 (a), the end sections 128a of optical fibers 128 which serve as the light reception end sections thereof, are positioned at a predetermined spacing along the outside face of the cylindrical reaction chamber 115, and the optical axes of the end sections 128a are set such that the lights going towards the radial direction from the axis of the cylinder of the reaction chamber 115 are received. The light introduced by the optical fibers 128 is input to the light receiving section 125, passed through a predetermined filter 127 that is set for each of the optical fibers 128, and then amplified, converted into an electrical signal, and analyzed by a PMT 126.

Furthermore, as shown in FIG. 13 (*b*), a pressing section 118*c* that presses the blocking section 113*a* is provided for the movement plate 118. The lens 122, which corresponds to the irradiation end section that irradiates light for excitation, which excites the fluorescent material, and the excitation trigger light source 123 are provided such that they sandwich the two wall faces of the reaction chamber 115 that have a large area. This movement plate 118 and the lens 122 are provided such that they can approach and separate with respect to the reaction chamber 115 as a result of an opening and closing mechanism that is not shown in the drawing.

Figure 14:
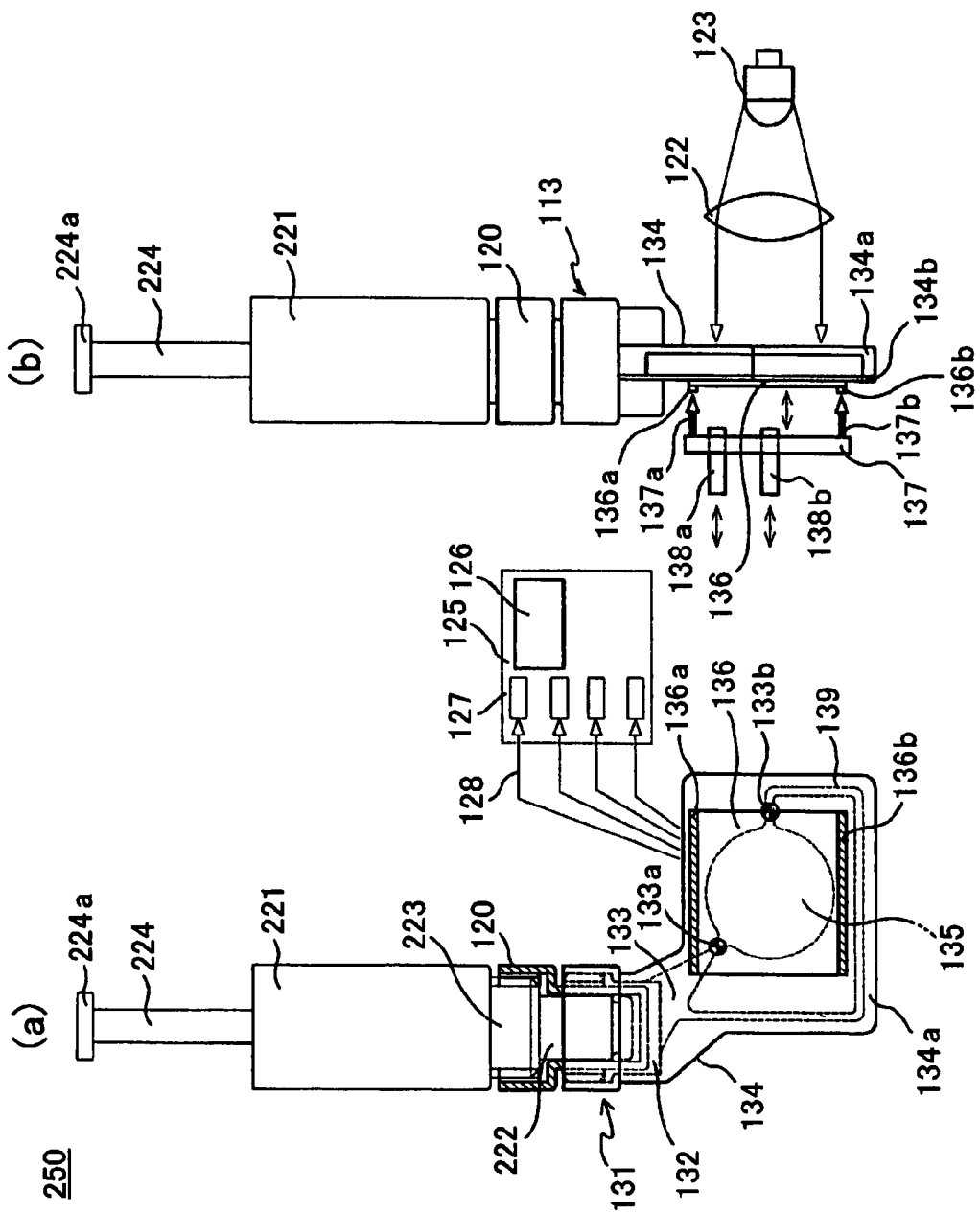
FIG. 14 is a drawing showing a reaction vessel according to a twelfth embodiment of the present invention, and where reaction measurement is to be performed.

FIG. 14 is a drawing showing the reaction vessel 131 according to a twelfth aspect of the present invention.

FIG. 14 (*a*) is a front view showing the reaction vessel 131. The reaction vessel 131 comprises; a storage chamber 132 in which a liquid is storable, that has an opening part, a cylindrical reaction chamber 135 that is communicated with the storage chamber 132 and is formed thinner than the storage chamber 132, and an introduction flow passage 133 and a discharge flow passage 139 that communicate between the storage chamber 132 and the reaction chamber 135. The introduction flow passage 133 communicates between the bottom face of the storage chamber 132 and a somewhat upper portion of the reaction chamber 135, and the discharge flow passage 139 connects between a somewhat lower portion of the reaction chamber 135 and the introduction flow passage 133. Reference symbol 133*a* and, 133*b* represent portions that are blockable by pressing, and here, for example, the aforementioned elastic valves are provided.

The reaction chamber 135 is consequently surrounded by two circular large bottom faces of a large area and one side wall face of a small area. The introduction flow passage 133, the discharge flow passage 139, and the reaction chamber 135 are formed in a layer form such that they sandwich the same, and the entirety thereof is provided in a translucent reaction section 134.

In regard to the optical information measurement section, as shown in FIG. 14 (*a*), the end sections 128*a* of the optical fibers 128 which serve as the light reception end sections thereof, are positioned at a predetermined spacing along the outside face of the cylindrical reaction chamber 135, and the optical axes of the end sections 128*a* are set such that the lights going towards the radial direction from the axis of the cylinder of the reaction chamber 135 are received. The light introduced by the optical fibers 128 is input to the light receiving section 125, passed through a predetermined filter 127 that is set for each of the optical fibers 128, and then amplified, converted into an electrical signal, and analyzed by a PMT 126.

As shown in FIG. 14 (*b*), in this example, the introduction flow passage 133, the discharge flow passage 139, and the reaction chamber 135 are formed in a bottomed planar frame 134*a*, and the opening side of the frame 134*a* is covered by a flexible thin film 134*b*. Furthermore, on one of the large bottom face sides of the reaction chamber 135, that is to say, on the film 134*b*, two rectangular shaped conductive thin films 136, which have a predetermined resistance value and serve as temperature raising and lowering bodies, and have a size that covers the reaction chamber 135 and a predetermined resistance value, are provided by adhesion, pasting, welding, or deposition, and the two opposing edges of the conductive thin films 136 are provided with electrode films 136*a* and 136*b* as the contact sections. In the drawing, reference symbol 133*a* is a blocking section that can block the introduction flow passage 133 by means of pressing.

As shown in FIG. 14 (*b*), as well as the exterior of the conductive thin films 136 being provided with terminals 137*a* and 137*b* such that they protrude out and are respectively able to make contact with the electrode films 136*a* and 136*b*, these terminals are provided on a movement plate 137 that is provided such that it can approach and separate with respect to the reaction vessel 131. These terminals are electrically connected to an information processing device or a power circuit that serves as the instruction section. Furthermore, the movement plate 137 comprises pressing sections 138*a* and 138*b* that are further movable with respect to the movement plate 137 in order to block the blocking sections 133*a* and 133*b*. The bottom face side of the reaction chamber 135 of the opposite side to the side in which the conductive thin films 136 are provided, is provided with a lens 122, which serves as the irradiation end section of the optical information measurement section, and an excitation trigger light source 123, and the irradiation of excitation light to the reaction chamber 135 is performed.

In regard to the nozzle 222 serving as the rotating body of the aforementioned liquid introducing device 250, this is as explained in FIG. 12, and the explanation is omitted.

According to the reaction vessel 131 of the present embodiment, the reaction chamber 135 is provided on the lower side of the storage chamber 132 in a position farther away from the rotation axis of the nozzle 222 which is the rotation body, than the storage chamber 132, that is to say, the axis of the opening part of the storage chamber 132. Consequently, the liquid that is dispensed into the storage chamber 132 by the dispensing tip by means of the suction and discharging of the nozzle 222, can be introduced into the reaction chamber 135 through the introduction flow passage 133 by the nozzle 222 rotating about the axis thereof, as a result of centrifugal force. When the liquid is introduced into the reaction chamber 135, the air that is present within the reaction chamber 135 is discharged to within the storage chamber 132 through the discharge flow passage 139, and in a case where the reaction chamber 135 is filled with the liquid, the blocking section 133*a* and 133*b* are pressed by the pressing sections 138*a* and 138*b* so that the reaction chamber 135 is sealed.

Next, by moving the movement plate 137 in the direction of the reaction chamber 135, the terminals 137*a* and 137*b* that are electrically connected to a power circuit and the like, are contacted with the electrode films 136*a* and 136*b* of the conductive thin film 136, and the conductive thin film 136 serving as the temperature raising and lowering body generates heat, so that the raising and lowering control of the temperature within the reaction chamber 135 can be performed.

Next, when the reaction completes, the entire reaction chamber 135 is irradiated with light from the excitation trigger light source 123 of the optical information measurement section that has a predetermined wavelength by using the lens 122, the light is received from the end sections 128*a* of the optical fibers which serve as the light reception end sections, that are positioned at predetermined intervals on the outside face of the reaction chamber 135, the light emission of a target wavelength is received via a filter 127 that is set to the optical fiber 128, and is then amplified, converted into an electrical signal, and analyzed by the PMT 126.

Figure 15:
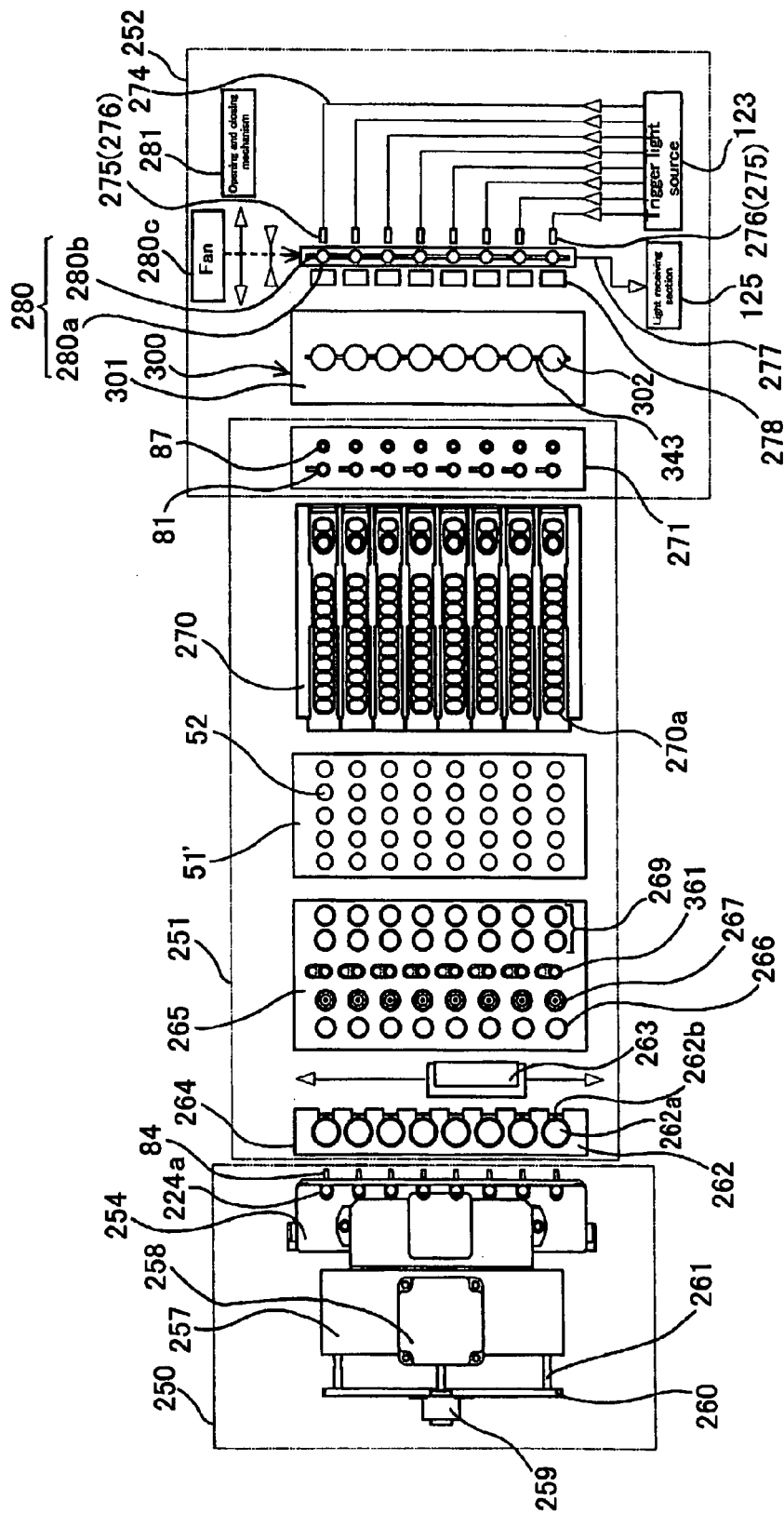
FIG. 15 is drawing showing an overall apparatus according to an embodiment of the present invention.

FIG. 15 is a concept diagram showing an entire reaction measurement processing system 10 according to an embodiment of the present invention.

The reaction measurement processing system 10 comprises; the liquid introducing device 250, a liquid treatment area 251 in which measurement preparations such as homogenization, extraction, reaction, transportation, and thinning of suspension liquids containing specimens based on various specimens, test reagents, and the like, are performed, and a reaction measuring area 252 that obtains optical information for executing real time PCR with respect to a solution that is sealed in the reaction chamber of the reaction vessel.

Figure 16:
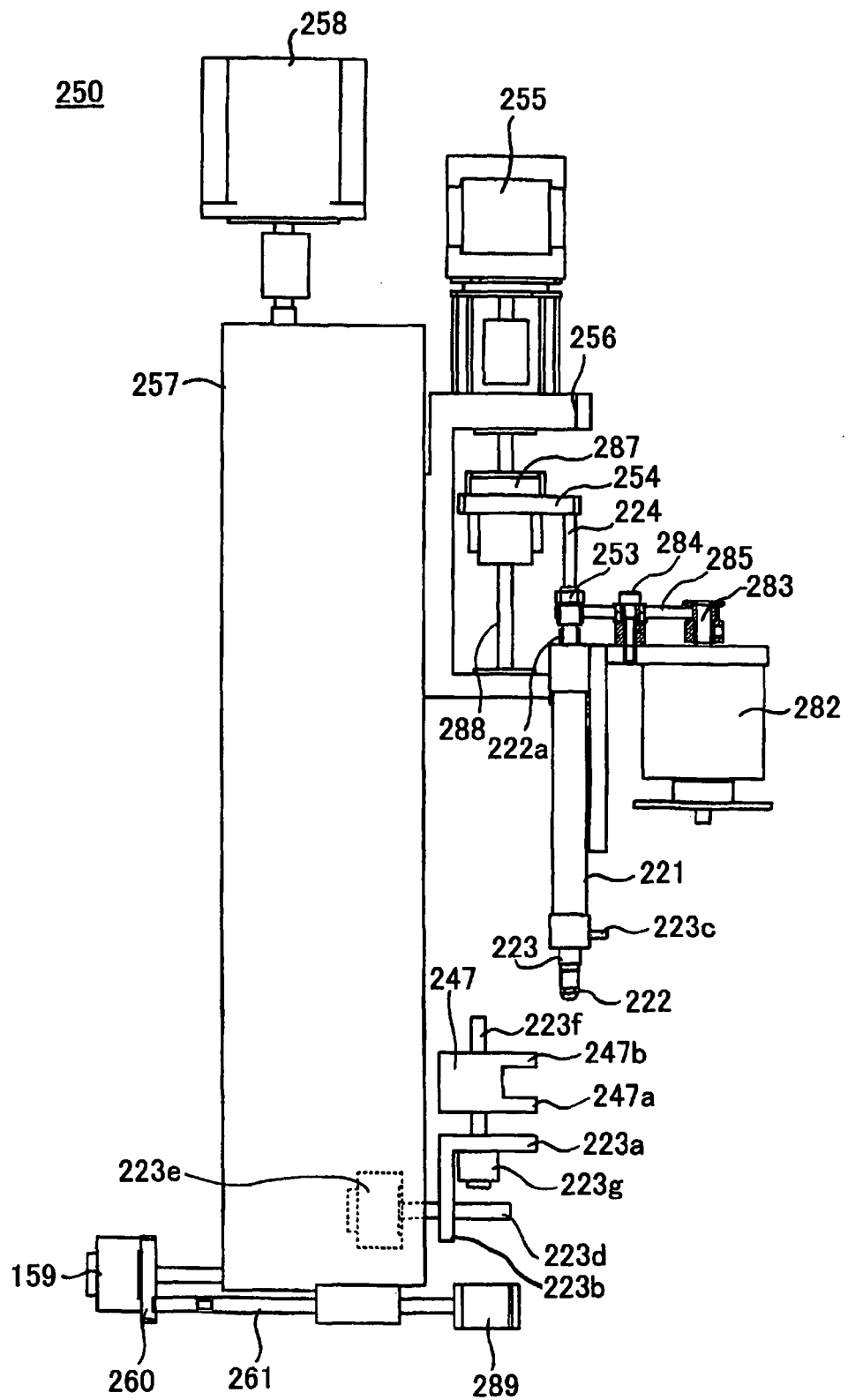
FIG. 16 is drawing showing a liquid introducing device according to an embodiment of the present invention.

As shown in FIG. 15 and FIG. 16, the liquid introducing device 250 has a plurality of (in this example, eight consecutive) rotatable nozzles 222 which are rotating bodies, and it is a device in which by installing various members on the threaded sections 223 which have been provided in a slightly more upper section than the ends of the nozzles 222, various processes, for example, thinning or capillaration of the liquid, homogenization of the suspension liquid, dispensing of the liquid, transportation, removal of impurities, extraction of the target material, stirring, washing, and the like, are possible. Here, installation includes threading, engagement, engaging insertion, accommodation, and the like.

The liquid introducing device 250 comprises, as shown in FIG. 15 and FIG. 16, a plurality of (in this example, eight consecutive) nozzles 222 which are rotating bodies, nozzles 222 that are covered by caps 120 and are provided with a suction and discharging part, threaded sections 223 that are provided in a slightly more upper section than the lower ends of the nozzles 222, that are installed to the caps 120 by threading, and rods 224 for sliding the plungers (not shown in the drawing) within the cylinders 222a that are communicated with the nozzles 222. Furthermore, the liquid introducing device 250 comprises, in order to rotate the eight consecutive nozzles 222 and the cylinders 222a about the axis center thereof, toothed pulleys 253 provided on the same center, a motor 282 for rotating the eight consecutive nozzles 222 and the cylinders 222a, a motor shaft 283 of the motor 282, and a belt 284 that spans the eight toothed pulleys 253 and the motor shaft 283. Reference symbol 285 denotes a roller for adjusting the tension of the belt 284. Here, in FIG. 15, the motor 282, the motor shaft 283, the belt 284, and the tension adjustment rotor 285 have been omitted to improve viewability. Furthermore, in FIG. 16, the installation of the reaction vessel 81 and the like, has been omitted.

The eight rods 224 are installed by hooking end sections 224a that protrude in the radial direction with a larger diameter than the diameter of the rods 224, to eight notched sections provided on the edge of a drive plate 254, and the drive plate 254 is connected to nut sections 287 that are threaded to ball screws 288. The rods 224 are always biased in the downward direction by a spring that is provided on the cylinders 222a. As a result, in a case where the rods 224 move in the upward direction, they are raised by the nut sections 287, but when they descend in the downward direction, they descend by the spring force, rather than by the nut sections 287. The ball screws 288 are rotationally driven by a motor 255 provided on a supporting member 256, which has a letter-U shaped cross-section, and as a result, the drive plate 254 and the eight rods 224 simultaneously move vertically.

In FIG. 16, reference symbol 223a denotes a tip removal plate for removing the installed dispensing tips. The tip removal plate 223a comprises a supporting section 223b that extends in the downward direction, and is threaded with a ball screw 223d, and the ball screw 223d is rotationally driven by means of a motor 223e. Consequently, by means of the rotation of the motor 223e, the tip removal plate 223a is advancable and retractable with respect to the nozzle 222. The motor 223e, the ball screw 223d, and accordingly, the tip removal plate 223a, are vertically movable by means of a vertical movement mechanism configured by a ball screw mechanism provided within a chassis 257.

An engaging block 247 provided with the cap engaging sections 247a and 247b is threaded to a ball screw 223f. By means of the rotation of the motor 223g, it is possible for the cap engagement sections 247a and 247b to approach or separate with respect to the tip removal plate 223a.

Reference symbol 223c denotes a flow passage for connection to a pressure sensor.

The supporting member 256 is vertically movable independent of the tip removal plate 223a by a vertical movement mechanism that is configured by a ball screw mechanism provided within the chassis 257. A motor 258 rotationally drives the ball screw. A magnetic force device comprising; a motor 259 for moving a magnet 289 which is for applying or removing a magnetic field from the outside of the dispensing tip installed to the nozzles 222 to within the tip, a horizontal rod 260, a rod 261, and the magnet 289, is provided on the underside of the chassis 57, and moves the magnet 289 left and right in the figure.

The liquid introducing device 250 is provided such that it is suspended from the upper side, and is movably provided as a result of an X axis Y axis movement mechanism that utilizes a linear movement mechanism (not shown in the drawing), such that it covers all regions of the reaction measurement processing system 10 and other necessary regions.

The liquid treatment area 251 of FIG. 15 comprises; a cartridge vessel 262 having eight consecutive specimen storage wells 262a that store the suspensions in which the specimens are suspended, a matrix form vessel 265 having wells in five columns by eight rows, eight cartridge vessels 270 for storing the various test reagents and materials necessary for executing real time PCR, or treatment products, a supporting platform that stores and supports the reaction chambers 52 of the reaction vessels 51' reaction vessels 51' arranged with the reaction chambers 52 in five columns by eight rows, and a holding rack 271 for retaining the eight reaction vessels 81 and the caps 87.

Furthermore, on the specimen storage wells 262a, barcodes 262b are respectively applied showing the information relating to the specimens thereof. The barcodes 262b are read by moving a barcode reading section 263 which reads the barcode, so as to scan the barcode. Reference symbol 264 denotes a movement mechanism of the barcode reading section 263.

The matrix form vessel 265 retains; a filter built-in tip column 266 for removing impurities by suction and discharging of the liquid following the homogenization process of the suspension containing the specimen, a dispensing tip column 267, a vessel column in which filter built-in vessels 361 (or column connection vessels) for homogenizing and removing the impurities from the suspension containing the specimen as a result of rotation are arranged, and wells 269 that store the test reagents necessary for PCR.

The filter built-in tip column 266 is utilized by engaging with the dispensing tip column 267. It has a filter chamber in which filters are built-in, and a filter is built-in to the interior thereof, and the suction and discharging of the liquid is possible such that it passes through the filter.

In regard to the present filter built-in vessel 361, the axis of the opening part, to which the bottom end section of the nozzle 222 is installable, becomes the rotation axis. Furthermore, the filter chamber, in which filters are built-in, is positioned farther away with respect to the axis than the storage chamber in which the liquid is storable, and moreover, the housing chamber, which eventually stores the liquid and is freely detachably provided, is positioned farther away from the axis than the filter chamber. Consequently, as a result of the rotation of the nozzle 222, the filter built-in vessel 361 installed to the same rotates, and as a result, the liquid stored in the storage chamber reaches the housing chamber through the filter chamber as a result of the rotation. In regard to the filter built-in vessel 361, a line that connects the storage chamber, the filter chamber, and the housing chamber creates an approximate acute angle with the axis.

Furthermore, returning to FIG. 15, by means of the pipette tip installed on the nozzle 222, the solution to be reacted is simultaneously dispensed into eight reaction chambers 52 of the reaction vessel 51' of the liquid processing area 251 at a time. By mounting the reaction vessel 51' on the reaction vessel supporting platform, the conductive films provided on the reaction chambers 52 conduct, and are in a heat generating state. Accordingly, incubation of the reaction liquids, which is a preprocess that is performed before the final PCR reaction, can be performed.

The reaction measuring area 252, in order to heat or cool the reaction chambers 85 of the reaction vessel 81 that is retained in a PCR unit 280 that retains the eight reaction vessels 81 (91, 111, 131) to which the target vessels have been introduced and sealed within the reaction chambers 85 (or 93, 101a, 115, 135) such that temperature controls and optical measurements are possible, there is a moving plate 278 provided along the thickness direction thereof of the reaction chamber 85, such that contact is possible with the conductive thin films 86 from the side on which the conductive films 86 have been provided as temperature raising and lowering bodies. This has terminals in which contact is possible with the electrode films 86a and 86b serving as the contact sections, and also has a pressing section that is movably provided with respect to the moving plate 278, for pressing the blocking section 83a and the blocking section 88a. The other side to the side to which the conductive thin films 86 are provided has the end sections 275 of optical fibers, which, within the reaction chamber 85, serve as irradiation end sections that irradiate the light from a trigger light source 123, which is an excitation irradiation light source, for obtaining the optical information from a labeling material in a case where a fluorescent material is used as the labeling material. In regard to the light receiving end section 276 that receives the light from the reaction chamber 85, in this example, a plurality of end sections 279 of optical fibers 277 are provided such that they are multiply arranged on a small area, which is the side face of the thin cylindrical reaction chamber 85, the optical axes of the end sections 279 are set such that they pass through the axis of the reaction chamber 85, and there is provided a photomultiplier 126 that receives the light at the optical fibers (279), and passes the light that is received through the optical fibers 277 through a predetermined filter, and, in regard to the respectively corresponding wavelengths, converts it into an electric signal.

In regard to the reaction vessels 81, they are respectively inserted into the eight slits 280b of the PCR unit 280 shown in FIG. 15, in a state where the opening parts 82a thereof are covered by the caps 87, and are further installed to the nozzles 222, and the reaction section 84 is plugged into the slit 280b of the PCR unit 280 in a state where it is supported by the nozzles 222 of the liquid introduction device 250. On the underside of the PCR unit 280, along the thickness direction (the normal direction of the circular shaped face of the reaction chamber 85) of the reaction section 84 thereof, one wall side thereof, that is to say, the wall side in which the film 84d has been provided, has two terminals provided in corresponding positions such that contact is possible with the electrode films 86a and 86b of the conductive thin film 86, and pressing sections that are advancable and retractable with respect to the blocking sections 83a and 88a, such that the blocking sections 83a and 88a are pressable, and it has a moving plate 278 that is movably provided with respect to the reaction section 84, and has a heat insulating effect. Furthermore, in regard to the other wall side, end sections 275 of optical fibers 274 which serve as the irradiation end sections, are movably provided with respect to the reaction section 84. The optical fibers 274 are optically connected to the trigger light source 123.

The moving plate 278, the pressing sections, which are further movably provided with respect to the moving plate 278, and the end sections 275 of the optical fibers, are simultaneously or individually movably provided with respect to the reaction section 84 by means of an opening and closing mechanism 281. The pressing sections provided for the moving plate 278, which are on the side face on which the film 84d of the reaction section 84 is provided, are provided such that they protrude in the normal direction of the plate face of the vertical plate form moving plate 278, and only the movement of the pressing sections is possible with respect to the moving plate. Furthermore, the PCR unit 280 has a fan 280c on the exterior thereof. The fan 280c is able to send air along the direction in which the eight consecutive reaction vessels 81 are arranged. For example, at the time the contact between the conductive thin film 86, which is the temperature control body, and the terminals provided for the moving plate 278 has been stopped, and the interval between the moving plate 278, which has a heat insulating effect, and the reaction section 84 has been separated, air is sent along the direction in which the eight consecutive reaction vessels 81 are arranged, and heat dissipation of the reaction chamber 85 is promoted. Consequently, temperature control can be efficiently performed.

The magnitude of the electrical current for the temperature control of the conductive thin film 86 of the temperature raising and lowering body, the movement of the moving plate 278 and the position thereof, the timing and strength of the ventilation by the fan 280c, and the timing, time, and the like, of the pressing by the pressing sections, are performed by input devices, such as a CPU, a keyboard, a switch, a mouse, or a communications device, a display device, or by providing the information processing device not shown in the drawing that has peripheral devices, and the like, including output devices including a CD, a DVD driver, or a printer, and by means of a signal input from the input device or a program control introduced to the information processing device.

Furthermore, as the PCR unit or the optical information measurement section provided for the reaction measurement area 252, even if a case where labeling with a variety of fluorescent materials for measuring the amount of a target material in the reaction chamber is assumed, as mentioned above, in addition to those that are suitable for the reaction vessel 81, a PCR unit or an optical information measurement section as explained in FIG. 12 to FIG. 14 can be exemplified.

For example, as shown in FIG. 12 (b), there is a case where the optical information measurement section comprises a lens 122, which serves as an irradiation end section, for irradiating the eight reaction sections 114, and a trigger light source 123 for irradiating excitation light. In this example, as shown in FIG. 12 (b), the light generated within the reaction chamber 115 is received by a half mirror 121 at a plurality of light receiving positions that are the same as a predetermined plurality of irradiation positions, input into a light receiving optical system, and finally passed through a predetermined filter and input into a PMT (photomultiplier). In this case, in regard to the PCR unit, both sides thereof are provided with a moving plates 118 and 119, and one of the moving plates 119 has a central portion 119*c* for measuring the optical information. Furthermore, the moving plate 118 comprises two terminals 118*a* and 118*b* and one pressing section 118*c*, and the moving plate 119 comprises two terminals 119*a* and 119*b*.

Alternatively, as shown in FIG. 13, the optical information measurement section comprises a lens 122, which serves as an irradiation end section, for irradiating the eight reaction vessels 111, and a trigger light source 123 for irradiating excitation light, the light generated within the reaction chamber 115 is received at the end sections 128*a* of a plurality of optical fibers 128 provided adjacent to the side face of a small area of the thin cylindrical reaction chamber 115, and in regard to the light reception section 125, light that has been passed through a predetermined filter 127 that has been provided for each of the fibers 128 is converted into an electrical signal by a PMT, and analyzed. At that time, the optical axes of the end sections 128*a* is set such that it passes through the axis of the cylinder. The moving plate 118 of this case comprises one pressing section 118*c* and two terminals 118*a* and 118*b*.

Furthermore, as shown in FIG. 14, the optical information measurement section comprises a lens 122, which serves as an irradiation end section, for irradiating the eight reaction vessels 131, and a trigger light source 123 for irradiating excitation light, and the light generated within the reaction chamber 135 is received at the end sections 128*a* of a plurality of optical fibers provided adjacent to the side face of a small area of the thin cylindrical reaction chamber 135. The moving plate 138 of this case comprises two pressing sections 118*c*, and two terminals 118*a* and 118*b*.

Figure 17:
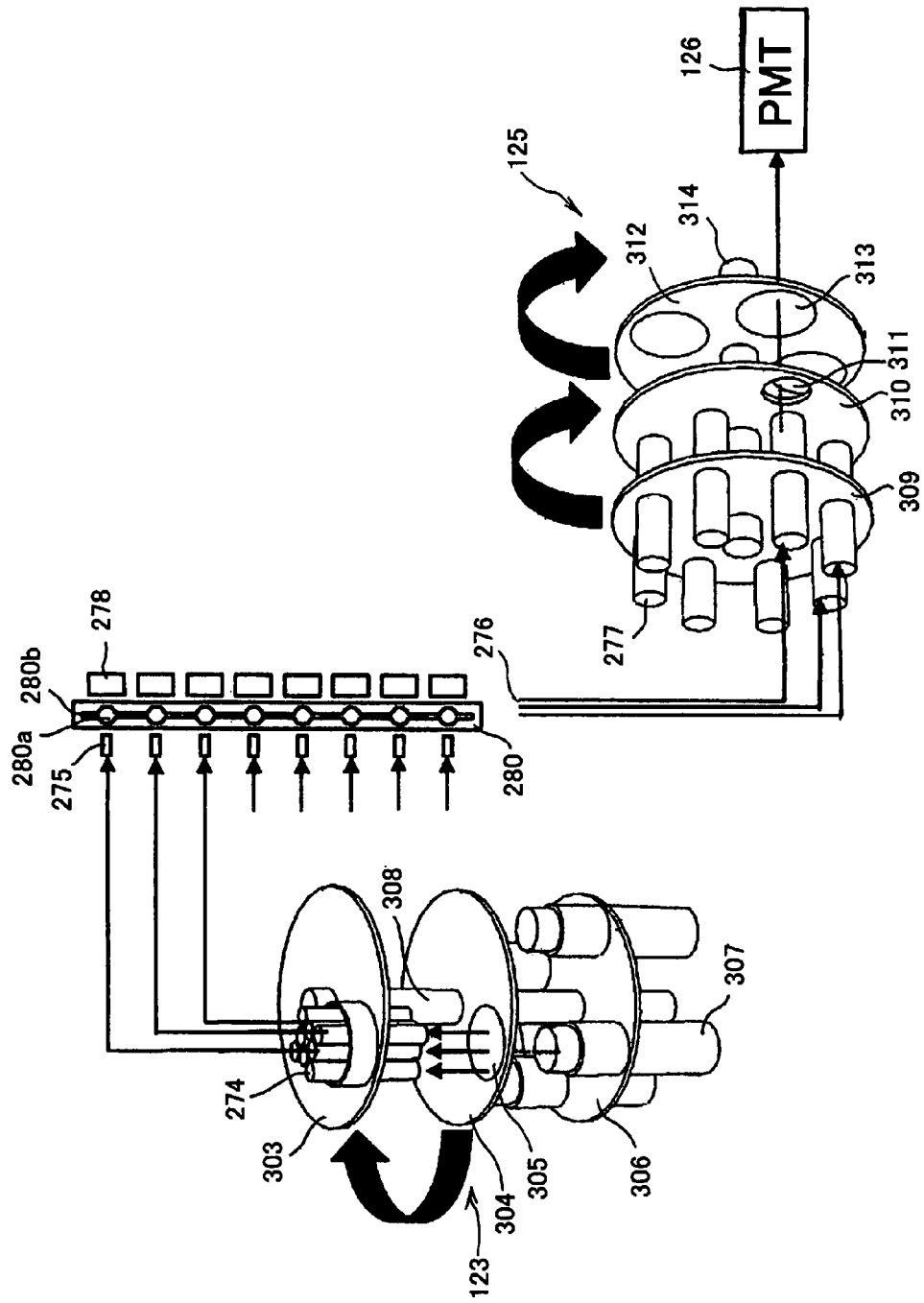
FIG. 17 is a drawing showing an optical information measuring device according to an embodiment of the present invention.

FIG. 17 shows a specific example of the trigger light source 123 and the light receiving section 125. The trigger light source 123 comprises; a rotating plate 303 which supports a bundle of optical fibers 274 that extend to the irradiation end sections of the eight reaction sections 84, a rotating plate 304 to which an optical lens 305 has been fitted into a hole that has been pierced in a location corresponding to the bundle of optical fibers 274, a supporting plate 306 onto which optical fibers 307 which introduce laser light from laser light sources (not shown in the drawing) that emit laser light having a plurality of wavelength types (four types in this example), are arranged at equal space intervals around the circumference along the traveling path of the optical lens 305, and a shaft 308 that rotatably supports the rotating plate 303 and the rotating plate 304 in a state where they are connected in correspondence, while supporting the supporting plate 306 such that it becomes unrotatable. According to the trigger light source 123, the lights from the four types of light sources which generate laser light having a plurality of wavelength types, are temporally switched, and light can be simultaneously irradiated in the eight reaction chambers 85 at the irradiation end sections. Hence the trigger light source 123 has a light source selection section.

The light receiving section 125 comprises; a supporting plate 309 that supports eight optical fibers 277 which extend to the light reception end sections of the eight reaction chambers 85, such that they are arranged at predetermined intervals, a rotating plate 310 in which a hole 311 with an area corresponding to the diameter of the optical fibers 277 has been pierced on the circumference corresponding to the arrangement positions of the optical fibers 277 of the supporting plate 309, a rotating plate 312 that is rotatably provided independently of the rotating plate 310 on which a plurality of types (four types in this example) of optical filters 313 have been arranged, and a shaft 314 that unrotatably supports the supporting plate 309, and independently rotatably supports the rotating plate 310 and the rotating plate 312. This light receiving section 125 corresponds to a light reception position selection section and an optical filter selection section.

According to the optical information measuring section of the present embodiment, by rotating the trigger light source 123 by a predetermined angle at a time in a state where the rotating plate 303 and the rotating plate 304 are connected, and by intermittently rotating the four types of light sources at a fixed time interval, they are simultaneously irradiated one type at a time into the eight consecutive reaction chambers 85 of the reaction vessels. Then, the fluorescence excited in the reaction chambers 85 of the reaction vessels 81 are introduced from the light reception end section 276 at the wall of the reaction chambers 85 with a narrow area, to the light receiving section 125 via the optical fiber 277. Then, the rotating plate 310, during the persistence time of fluorescence during the irradiation of the one type of excitation light, sequentially leads the light from the reaction chambers of the eight consecutive reaction vessels 81 to the rotating plate 312 by intermittently rotating the rotating plate 310 by one revolution, and furthermore, while the fluorescence from a single reaction vessel 81 is being received, by rotating the rotating plate 312 by one revolution, the light is introduced to the PMT 126 by sequentially passing it through the four types of optical filters 313. This operation is sequentially performed with regard to the four types of excitation light.

Figure 18:
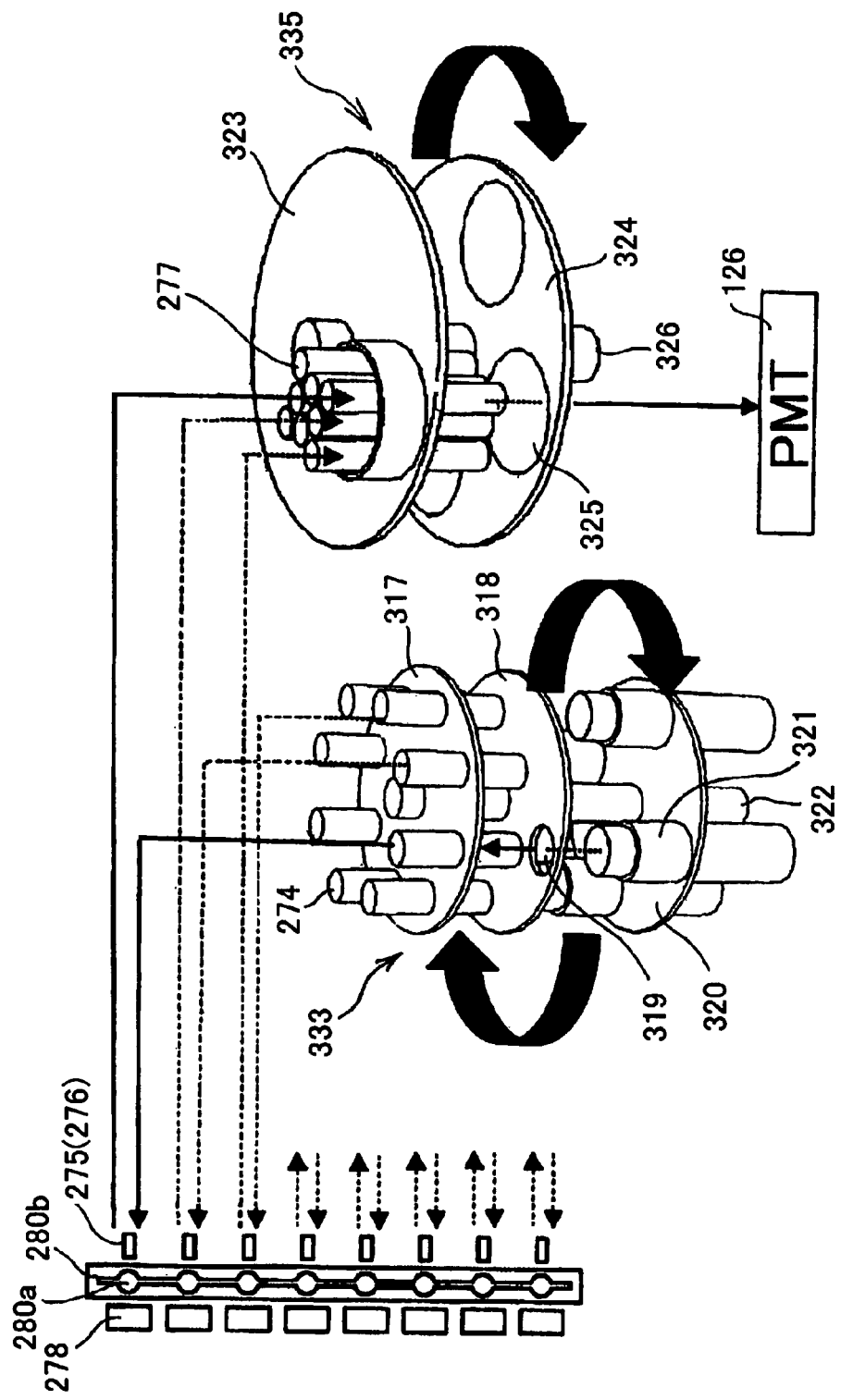
FIG. 18 is a drawing showing an optical information measuring device according to an embodiment of the present invention.

FIG. 18 shows a trigger light source 333 and a light receiving section 335 according to another embodiment.

The trigger light source 333 comprises; a supporting plate 317 that supports the eight optical fibers 274 which extend to the end sections 275 of the optical fiber that are the irradiation end sections of the eight reaction sections 84, such that they are arranged at predetermined intervals, a rotating plate 318 in which a hole 319 with an area corresponding to the diameter of the optical fibers 274 has been pierced on the circumference corresponding to the arrangement positions of the optical fibers 274 of the supporting plate 317, a supporting plate 320 that is rotatably provided independently of the rotating plate 318 and on which optical fibers 321 from a plurality of types (four types in this example) of light sources are arranged at predetermined intervals, and a shaft 322 that unrotatably supports the supporting plate 317 and rotatably supports the rotating plate 318. The trigger light source 333 has a light source irradiation position selection function.

Furthermore, the light receiving section 335 comprises; a supporting plate 323 that supports the eight optical fibers 277 that extend from the light reception end sections 276 of the eight reaction chambers 85 as a bundle, and a shaft 326 that rotatably supports the four types of optical filters 325 by piercing a plurality (four in this example) of holes having positions and sizes corresponding to the bundles of optical fibers 277 of the supporting plate 323. Accordingly, the light receiving section 335 has an optical filter function.

According to the optical information measuring section of the present embodiment, the excitation light for fluorescence generation from the four types of light sources, by intermittently rotating the rotating plate 318 by one revolution, passes through the hole 319 provided in the rotating plate 318, and the excitation light is introduced to the reaction chambers 85 of the eight consecutive reaction vessels 11 through the optical fibers 274. Then, the fluorescence that has been excited in the reaction chambers 85 that have been irradiated with the excitation light is introduced to the light receiving section 335 via the optical fiber 277. By sequentially rotating the rotating plate 324 during the time the fluorescence from a single reaction chamber 85 is sustained, it is sequentially passed through the four types of optical filters 325, and is introduced into a photomultiplier 126.

Returning again to FIG. 15, by further storing the reaction vessel 81 in the reaction measuring area 252, it has a liquid introducing rotating storing section 300 provided with eight consecutive vessel storing sections 344, which correspond to the rotating bodies which store and rotate the reaction vessels 81. The liquid introducing rotating storing section 300 comprises a chassis 301 in which the eight consecutive vessel storing sections 344 are stored, a hole section 302 for storing the reaction vessel 81 that is to be rotated in the vessel storing section, which is pierced through the upper portion of the chassis 301, and a slit section 343 for easily storing the protruding portions, such as the reaction sections 84 of the reaction vessels 81.

Figure 19:
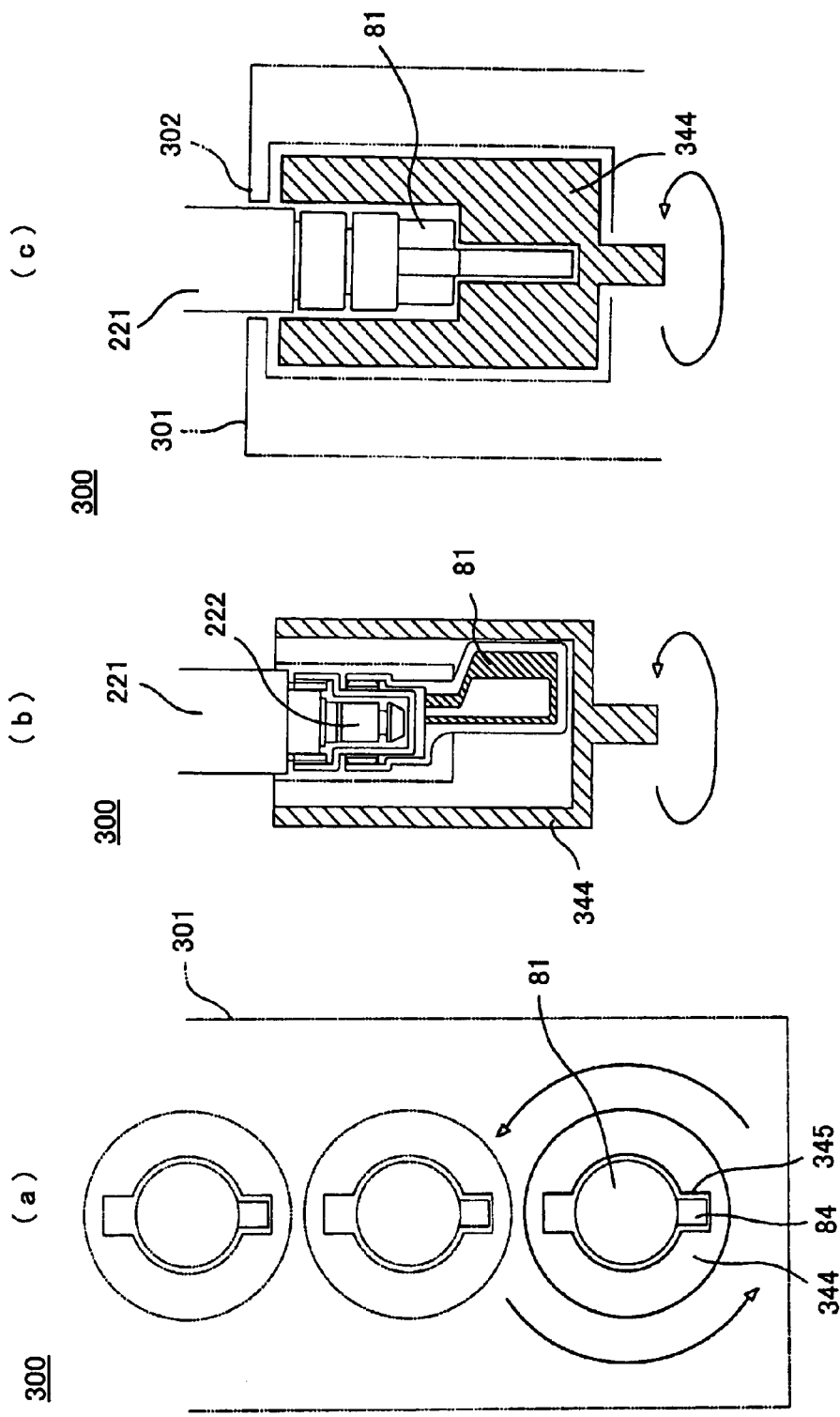
FIG. 19 is a drawing showing a rotation mechanism according to an embodiment of the present invention.

FIG. 19 (*a*) shows a plan view of the eight consecutive vessel storing sections 344 that are provided within the chassis 301. A concave section 305 is provided in the vessel storing section 344, which is the portion into which the reaction section 84 of the reaction vessel 81 that is to be stored is inserted.

FIG. 19 (*b*) shows a front cross-sectional view of the vessel storing section 344 in which the schematically shown reaction vessel 81 has been stored. FIG. 19 (*c*) shows a cross-sectional side view of the chassis 301 of the liquid introducing rotating storing section 300, and the vessel storing section 344 that has been provided therein.

The vessel storing section 344 is rotated in a state storing the reaction vessel 81. The rotation axis of the vessel storing section 344 is provided such that it passes through the stored vessel. According to the present embodiment, since the liquid introducing rotating storing section 300 is provided in addition to the liquid introducing device 250, processing can be performed with a good efficiency.

Figure 20:
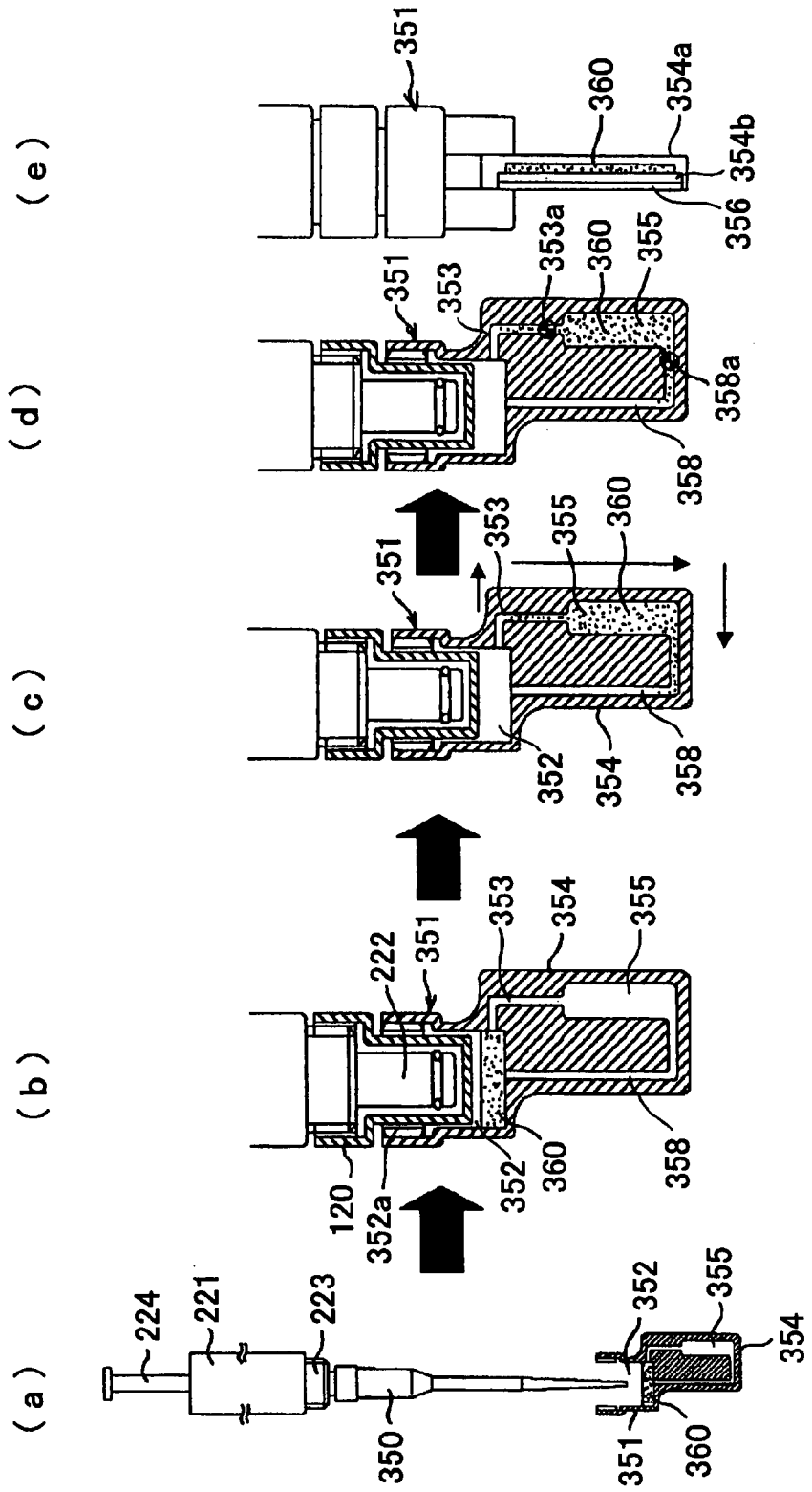
FIG. 20 is a process flow diagram according to an embodiment of the present invention.

Next, the process flow using the reaction measurement processing system 10 explained above is explained based on FIG. 15, and on FIG. 20 which shows the process flow conceptually.

Here, a case in which measurement is performed by using the real time PCR method to measure the quantity of DNA contained in a fixed specimen is explained. Real time PCR is a method for measuring the concentration of nucleic acids by using a nucleic acid probe. The method thereof utilizes, for example, a phenomenon wherein at the time the nucleic acid probe that has been labeled with a fluorescent dye hybridizes into the target nucleic acid, the light emission of the fluorescent dye decreases by a level that depends on the type and base sequence of the base to which the fluorescent dye has bonded, or a phenomenon wherein the light emission strength increases as a result of removing the nucleic acid probe from the target nucleic acid (light emission and light extinction phenomena), or utilizes a method in which a test reagent that emits fluorescent light as a result of the insertion of double-stranded DNA, is added to the reaction system, then a method of detecting the fluorescent light accompanying amplification is utilized, and the determination is performed by detecting the fluorescent light strength thereof (the intercalator method).

In the cartridge vessel 262 of the reaction measurement processing system 10, eight specimens comprising suspensions in which biological tissue, such as skin that has been obtained from patients or the like is suspended, are stored in advance. Furthermore, in the wells 69 and the cartridge vessels 70, for example, test reagents necessary for PCR, DNA polymerase, reaction buffer liquids, fluorescent test reagents, primers, other test reagents thereof, and the like, are stored in advance. The nozzles 222 of the liquid introducing device 250 are, by means of a raising and lowering mechanism not shown in the drawing, simultaneously installed by engagement to the eight dispensing tips that are retained by a tip rack not shown in the drawing as a result of being depressed with respect to the eight dispensing tips. Then by simultaneously repeating the suction and discharging in regard to the sample stored in the cartridge vessels 262, the biological tissue, which is a solid contained in the suspension, is crushed or homogenized to the cellular level thereof. Next, the liquid introducing device 250 is moved in a state where the suspension is suctioned into the dispensing tips, to the location at which the eight filter built-in vessels 361 are stored, that is to say, moved to the position of the third row from the left in the drawing of the matrix form vessel 265, and the suspensions stored in the dispensing tips are discharged into the storage chambers of the eight filter built-in vessels 361.

Installation is performed by inserting the lower end sections of the nozzles 222 into the opening parts of the storage chambers. In this state, the filter built-in vessels 361 are lifted to the upper side of the matrix form vessel 265, and the filter built-in vessels 361 are simultaneously rotated together with the nozzles 222 by simultaneously rotating the eight consecutive nozzles 222. Then, the homogenized suspensions stored in the storage chambers of the filter built-in vessels 361 move from the storage chambers, pass through the filters within the filter chambers, to the housing chambers, by means of centrifugal force resulting from rotation. As a result of the filters, the impurities are captured, and solutions without impurities that contain the target DNA can be obtained in the housing chambers. The housing chambers are detached from the filter chambers of the filter built-in vessels 361, the dispensing tips are installed, the solution is suctioned, and the solutions containing the target DNA are, for example, stored in one well 269 per column of the matrix form vessel 265. Next, the test reagents are suctioned from a predetermined well 270*a* of the cartridge vessel 270, in which the necessary test reagents according to the processing objective, for example, a probe that has been labeled with a specimen or fluorescent material, a reagent for a ligation reaction, and the like, have been stored, discharged in the well 269, and a solution that is mixed with the necessary test reagents is produced. At that time, if necessary, for example, in order to perform incubation for bonding the probe, which is for labeling with a fluorescent material, to the target DNA, the solution within the well 269 is suctioned by the installed dispensing tip and discharged and stored in a predetermined reaction chamber 512 of the reaction vessel 51', and maintained at a temperature set by a signal from an instruction section not shown in the drawing by generating heat as a result of flowing an electrical current through the conductive thin film coating the reaction chamber 52.

Next, the eight consecutive nozzles 222 are moved to the tip rack (not shown in the drawing) by moving the nozzle heads of the liquid introducing device 250, and by operating the raising and lowering mechanism of the nozzles 222, the nozzles 222 are installed by inserting into and engaging the eight unused dispensing tips 350 stored in the tip rack. Next, the dispensing tips 350 are moved to the eight wells 269, and the solutions 360 stored within the wells 269 are simultaneously suctioned into the unused eight consecutive dispensing tips 350. Then, as conceptually shown in FIG. 20 (*a*), they are transported to the eight reaction vessels 351 that are retained by the holding rack 271, and the solutions 360 are discharged into the storage chambers 352 thereof. Following discharging, the eight dispensing tips 350 are removed from the nozzles 222 of the liquid introducing device 250 by the tip removal plate 223a, and are discarded.

Next, the liquid introducing device 250 is moved to the position of the holding rack 271 in which the eight caps 120 are stored, the nozzles 222 are simultaneously inserted into the eight caps 120, and by rotating the nozzles 222, the eight caps 120 are installed to the threaded sections 223.

Next, as shown in FIG. 20 (b), the nozzle heads of the liquid introducing device 250 are moved to the position at which the reaction vessels 351 of the holding rack 271 are retained, the caps 120 installed on the nozzles 222 are inserted within the opening parts 352a and the storage chambers 352 of the reaction vessels 351, in which the solutions 360 have been stored, and as a result of simultaneously rotating the nozzles 222, they are installed by threading the reaction vessels 351 onto the caps 120. Next, following raising of the reaction vessel 351 to the upper side of the holding rack 271, the nozzle 222, and accordingly the reaction vessel 351 installed to the nozzle 222, are simultaneously rotated at a high speed in the same direction as the rotation for threading at the cap 120 and the opening part 352a. In regard to the reaction vessel 351, in a state where it is stored in the holding rack 271, since the reaction chambers 355 thereof are retained in a state where they are respectively inserted into a slit-shaped space provided in the holding rack 271, the reaction, vessel 351 does not rotate during the rotation of the nozzle 222.

Then, as shown in FIG. 20 (c), the solutions 360 stored within the storage chambers 352 move through the introduction flow passage 353 to the reaction chambers 355 by centrifugal force, and are introduced into the reaction chambers 355. At this time, the air that is in the reaction chambers 355 is discharged to the storage chambers 352 through a discharge flow passage 358.

The reaction vessels 351 in which the solutions have been introduced to the reaction chambers 355 are transported to the PCR unit 280 by the liquid introducing device 250 in a state with the caps 120 installed, and they are retained such that they are supported by the hole 280a and the slit 280b portions of the PCR unit 280.

As shown in FIGS. 20 (d) and (e), the movement plate is brought close to the reaction chambers 355 by the opening and closing mechanism 281, and the pressing portions provided so as to be movable with respect to the movement plate, are approached to the blocking sections 353a and 358a by means of the opening and closing mechanism 281, and pressed to deform the blocking sections, so that inside of the reaction chambers 355 are simultaneously made a sealed state. At that time, the face of the adjacent side of the movement plate is the side of the conductive thin film 356 serving as the temperature raising and lowering body which is adhered, pasted, welded, or deposited on the outside of the flexible film 354b provided on the side of the opening of the frame 354a that forms the reaction section 354.

Next, the terminals that are electrically connected to a power circuit, or the like, which is provided on the movement plate, are simultaneously moved and brought into contact with respect to an electrode film of the reaction section 354 by means of the opening and closing mechanism 281. Consequently, a predetermined electrical current, which is an electrical signal from an information processing device or a power circuit, which is the instruction section or an electromagnetic supply section, is flowed through the conductive thin film 356, and heat is generated. By adjusting the magnitude of the electrical current, temperature control is performed based on the PCR method.

At that time, in the present embodiment, since the conductive thin film 356, which is the temperature raising and lowering body, is directly provided to the reaction chambers 355, it becomes possible to provide a vessel for PCR with faithful responsiveness with respect to temperature changes.

In this PCR amplification process, for example, as shown in FIG. 17, in regard to the trigger light source 123 serving as the light for excitation that excites the fluorescent material which is the labeled material used in the reaction chambers 355, light from the light source of the wavelength selected by the rotating plate 304 is simultaneously irradiated into the reaction chamber 355 through the optical fibers 274 at the lenses 122, which are irradiation end sections. At that time, at the light receiving sections 125, in regard to the eight reaction chambers 355, the emitted lights received at the light reception end sections 276 at the light reception positions are sequentially selected by the rotating plate 310, and in regard to the intermittent rotation of the rotating plate 310, within the time the received light from a single light reception end section 276 is selected, the rotating plates 312 are sequentially intermittently rotated one rotation, and in a case where the corresponding optical filter 313 is selected, data regarding the light input into the PMT 126 is obtained. The operations above, in regard to all four types of light wavelengths, measure by converting the light received from all the reaction chambers 355 into an electrical signal. As a result, the state of the light emission strength of the fluorescent material is measured in real time, and the quantity of DNA that is the subject thereof, can be measured.

Furthermore, in a case where the reaction chamber 355 is cooled by separating the movement plate from the reaction chamber 355, then by simultaneously subjecting the reaction vessels 351 to cold air by means of the fan 280c, heat can be efficiently released from the reaction chamber 355.

According to the present embodiment, it is possible to homogenize the suspension containing the specimen, extract a solution containing the target DNA from the homogenized suspension, thin the solution to which all test reagent types have been mixed with the DNA, and efficiently and consistently automatically perform the operations until the optical information is obtained, while performing accurate and highly responsive temperature controls of the thinned solution, in a compact device.

In the above explanation, as the conductive thin film, one where an aluminum oxide foil is coated on an aluminum thin film as shown in FIG. 1 (f) is used, however it is in no way restricted to this case, and for example various kinds of conductive thin films such as tin oxide or the like may be used. As the liquid introducing mechanism, in regard to the liquid introducing device 250, although the liquid stored in the storage chamber was introduced to the reaction chamber by installing the reaction vessel to the nozzle 222 serving as a rotating body, it is in no way restricted to this, and as the liquid introducing mechanism, it is acceptable if the reaction vessel 351 is installed to the nozzle 222 of the liquid introducing device 250 within the vessel storage section 344 of the liquid introducing rotating storing section 300, the reaction vessel 351 is stored within the vessel storage sections 344 of the liquid introducing rotating storing section 300, and the introduction is performed by rotation. In particular, in regard to the production of the liquid that is stored within the reaction vessel 351, the movement of the liquid introducing device 250 is simplified by using the liquid introducing rotating storing section 300.

As the reaction vessel, it is acceptable that by installing the tip-shaped reaction vessel 101 to the nozzle 222 of the liquid introducing device 250 via the cap 102, the liquid is introduced into the gap section 101a serving as the reaction chamber, not as a rotating body, but by using the suction and discharging function of the nozzle 222.

In this case, in regard to the liquid introduced into the gap section 101*a*, following sealing of the gap section 101*a* and following reaction, as a result of opening the hole section 102*f* by moving the cap engaging sections 247*a* and 247*b* in the somewhat upper direction with respect to the tip removal plate 223*a*, the nozzle 222 and the gap section 101*a* is communicated, the sealed state is released, and by discharging with respect to the nozzle 222 through the thin diameter section 106, the product can be collected.

The embodiments above have been specifically explained in order to better understand the present invention, and do not restrict other embodiments in any way. Accordingly, they are changeable within a scope that does not depart from the gist of the invention. For example, in regard to the optical information measuring device, it is acceptable for optical systems such as a half mirror, a mirror, or an optical filter, to be used to distribute the light, rather than selecting the light by temporal switching as mentioned above.

Furthermore, the various mechanisms are not restricted in any way to those mentioned above, and, for example, as a rotation mechanism of the nozzles, it is possible to use a gear mechanism instead of a belt mechanism. Furthermore, for example, it is possible to use the rotation mechanism achieved by the present inventor that has been disclosed in PCT International Publication No. WO 2002/063300.

The shape of the reaction vessels is not restricted to that explained above, and it is acceptable if they are not cylindrical, but are a prismatic shape or a spherical shape. Furthermore, although an example is described where they are installed to the nozzles via the cap, it is acceptable if they are directly installed to the nozzles without including the cap. In regard to the rotation mechanism and the suction and discharge mechanism of the nozzles of the liquid introducing device 250, the number of nozzles, and the number of the various vessels, they are not restricted by the above explanation in any way. Cases where the number of nozzles and vessels is one, or a number other than eight, are acceptable. Furthermore, although the filter was used to remove the impurities within the suspension, it may be used to capture the target material.

In regard to the rotation supporting axle, not only a case where it is provided along the axis of the opening part 82*a* of the storage chamber 82 as shown in FIG. 8 is possible, but it acceptable for it to be provided such that it is parallel to the axis of the opening part 82*a*. Since this rotation supporting axle is a portion of the vessel, the rotation of the vessel of this case about the rotation supporting axle also corresponds to rotation of the vessel about its own axis.

Furthermore, although the explanation above used the optical information measuring section of FIG. 17, it is acceptable to use the optical information measuring section of FIG. 18. Moreover, although the conductive thin film was provided on one side of the reaction chamber, it is acceptable to provide it on both sides. Furthermore for the cooling section, instead of a fan, it is acceptable to use one where a cooling medium is flowed through a flow passage. Moreover, in the explanation above, although embodiments regarding the thinning of a liquid were mainly given, capillaration of a liquid can also be performed.

Moreover, the abovementioned various reaction vessels, the temperature raising and lowering body, the storage chambers, the reaction chambers, the flow passages, the reaction sections, the rotation supporting axles, the conductive thin films, the films, the frame, the electrode films, the contact sections, the walls, the dispensing tips, the light measuring sections, the caps, the various kinds of vessels, the test reagents, the nozzles, the parts such as the heating and cooling sections, the liquid introducing mechanism, and the various kinds of mechanisms, can be arbitrarily combined while appropriately modifying them.

INDUSTRIAL APPLICABILITY

This relates to the reaction vessel, and the reaction controller according to the present invention. The present invention is, for example, related to fields in which processing, testing, and analysis related to biological material particularly genetic material, principally in regard to, for example, DNA, RNA, mRNA, rRNA, tRNA, and plasmids, is required, and is related to all fields, for example, industrial fields, agricultural fields such as food products, agricultural products, and seafood processing, health care fields such as drug fields, sanitation, health, disease, and genetics, and scientific fields such as biochemistry or biology. The present invention can particularly be used in various DNA-handling analysis and tests, such as PCR, and real time PCR.

BRIEF DESCRIPTION OF THE REFERENCE SYMBOLS

10 Reaction measurement processing system
11, 21, 31, 41, 51, 61, 71, 81, 91, 101, 111, 131, 351 Reaction vessel
12, 22, 32, 42, 52, 62, 72, 85, 93, 101*a*, 115, 135, 335 Storage chamber
16, 26, 36, 46, 56, 66, 76, 86, 100, 105*b*, 116, 136, 356 Conductive thin film (temperature raising and lowering body)
15, 25, 35, 45, 55, 65, 75, 105*c* Wall
16*a*, 16*b*, 26*a*, 26*b*, 36*a*, 36*b*, 56*a*, 56*b*, 66*a*, 66*b*, 76*a*, 761, 762, 763, 86*a*, 86*b*, 100*a*, 100*b*, 105*b*, 116*a*, 116*b*, 117*a*, 117*b*, 136*a*, 136*b* Electrode films (contact section)
18*a*, 18*b*, 28*a*, 28*b*, 37*a*, 37*b*, 48*a*, 48*b*, 58*a*, 68*a*, 68*b*, 771, 772, 773, 774, 118*a*, 118*b*, 119*a*, 119*b*, 137*a*, 137*b* Terminals
27*c*, 58*b*, 79, 109, 110, 249*a*, 249*b* Terminal blocks (terminals)
37*a*, 37*b* Plate form terminals (terminals)
48*a*, 48*b* Film form terminal (terminals)
18, 57, 84*d*, 97, 114*b*, 134*b* Film (film form member)
87, 102, 120 Cap
123 Trigger light source
125 Light receiving section
126 PMT (photomultiplier)
Nozzle (rotating body)
Liquid introducing device (liquid introducing mechanism)
251 Liquid treatment area
252 Reaction measuring area
Liquid introducing rotating storing section (liquid introducing mechanism)

The invention claimed is:
1. A reaction vessel comprising:
one or a plurality of reaction chambers in which liquid is storable,
a wall that surrounds said reaction chambers,
a storage chamber in which a liquid is storable, said reaction chamber is formed thinner or narrower than said storage chamber,
a connection section that is detachably connectable to a liquid introducing mechanism provided on the exterior, liquid is introducible into said reaction chamber by connecting said connection section to said liquid introducing mechanism, and a flow passage that communicates said reaction chamber and the exterior, wherein an entirety or a part of the wall of said reaction chambers is formed by a temperature raising and lowering body that can raise or lower the temperature thereof according to a signal from the exterior, wherein said liquid introducing mechanism comprises a nozzle and a suction and discharge section that performs suction and discharging of gas via said nozzle, said connection section is an opening part of said storage chamber, which is communicated with said reaction chamber, and said opening part is connectable by said nozzle, wherein the storage chamber is in fluid communication with the reaction chamber via a first opening located at an upper section of the reaction chamber, and the flow passage is in fluid communication with the reaction chamber via a second opening located at a lower section of the reaction chamber, and wherein the first opening, the reaction chamber, the second opening, and the flow passage are axially aligned along a longitudinal axis.

2. The reaction vessel according to claim 1, wherein said wall is formed such that an inner wall face thereof faces into the reaction chamber, an outer wall face thereof is on the outside of the reaction chamber, and an interval between the inner and outer wall faces are integrally formed.

3. The reaction vessel according to claim 1, wherein said temperature raising and lowering body comprises a conductive member that has a predetermined electrical resistance, and said signal is an electromagnetic signal.

4. The reaction vessel according to claim 3, wherein said conductive member forms a wall of said reaction chamber, or covers said wall, is built into said wall, or is attached to said wall.

5. The reaction vessel according to claim 1, wherein said reaction vessel is provided with a plurality of said reaction chambers arranged in a plane at a predetermined interval.

6. The reaction vessel according to claim 1, wherein said reaction vessel is provided with a contact section that receives an electrical signal by making contact with a terminal of an electromagnetic supply section provided to the exterior.

7. The reaction vessel according to claim 1, wherein said wall and/or a portion or the entirety of said temperature raising and lowering body has translucency or semi-translucency.

8. The reaction vessel according to claim 1, wherein a wall that surrounds said reaction chamber has a plurality of wall faces, and amongst the wall faces, at least one is formed by a soft material film form member.

9. The reaction vessel according to claim 8, wherein a conductive member with a predetermined electrical resistance is coated, built in, or attached on said film form member, as said temperature raising and lowering body.

10. The reaction vessel according to claim 1, wherein said wall of said reaction chamber comprises a planar frame that comprises grooves or holes, and a film form member or a thin plate is provided such that it covers one face side or both face sides of said frame.

11. The reaction vessel according to claim 1, wherein an opening part of said reaction vessel comprises a connectable cap that is freely detachable.

12. The reaction vessel according to claim 1, wherein a deformable soft member is provided for at least a portion of said reaction vessel, and said reaction chamber is sealable by deforming said soft member.

13. The reaction vessel according to claim 12, wherein said reaction chamber is sealable by sealing an interval between said storage chamber and said reaction chamber, and an interval between said reaction chamber and the exterior.

14. A reaction controlling device comprising:

one or two or more reaction vessels, and an instruction section that generates a signal that instructs the raising or the lowering of the temperature with respect to said reaction vessel from the exterior, wherein said reaction vessel comprises one or a plurality of reaction chambers in which a liquid is storable, and a wall that surrounds said reaction chamber, wherein the entirety or a part of said wall is formed by a temperature raising and lowering body in which raising or lowering of the temperature is possible by means of a signal from said instruction section, wherein said reaction vessel further comprises a storage chamber in which a liquid is storable, that has an opening part and is communicated with said reaction chamber, and said reaction chamber is formed thinner or narrower than said storage chamber, the reaction chamber has a flow passage that communicates said reaction chamber and the exterior, wherein the storage chamber is in fluid communication with the reaction chamber via a first opening located at an upper section of the reaction chamber, and the flow passage is in fluid communication with the reaction chamber via a second opening located at a lower section of the reaction chamber, wherein the first opening, the reaction chamber, the second opening, and the flow passage are axially aligned along a longitudinal axis, wherein said reaction controlling device further comprises a liquid introducing mechanism whereby liquid is introducible into said reaction chamber by connecting to said reaction vessel, and said reaction vessel comprises a connection section that connects to said liquid introducing mechanism, wherein said liquid introducing mechanism comprises a nozzle and a suction and discharge section that performs suction and discharging of gas via said nozzle, said connection section is the opening part of the storage chamber, which is communicated with said reaction chamber, and said opening part is connectable by said nozzle, and wherein the nozzle is provided so as to be capable of horizontal movement and vertical movement thereof.

15. The reaction controlling device according to claim 14, wherein said temperature raising and lowering body comprises a conductive member that has a predetermined electrical resistance, and said instruction section comprises an electromagnetic supply section that applies an electromagnetic signal to said temperature raising and lowering body.

16. The reaction controlling device according to claim 15, wherein said electromagnetic supply section makes contact with or is adjacent to a wall of said reaction chamber, or comprises one or a plurality of terminals that are provided such that they can approach and separate with respect to a wall of said reaction chamber.

17. The reaction controlling device according to claim 15, wherein said conductive member forms a wall of said reaction chamber, or covers a wall face of said wall, is built into said wall, or is attached to said wall.

18. The reaction controlling device according to claim 14, wherein there is further provided, in order to cool said reaction chamber, a fan that blows air towards said reaction chamber according to a signal from said instruction section, or a refrigerant circuit that follows along a route that makes contact with or is adjacent to said reaction chamber, and circulates a refrigerant according to a signal.

19. The reaction controlling device according to claim 14, wherein said wall and/or the entirety or a part of a temperature raising and lowering body has translucency or semi-translucency.

20. The reaction controlling device according to claim 14, wherein a wall that surrounds said reaction chamber has a plurality of wall faces, and amongst the wall faces, at least one is formed by a soft material film form member.

21. The reaction controlling device according to claim 20, wherein a conductive thin film with electrical resistance is coated, or built in, on said film form member, as said temperature raising and lowering body.

22. The reaction controlling device according to claim 14, wherein an opening part of said reaction vessel comprises a connectable cap that is freely detachable.

23. The reaction controlling device according to claim 14, wherein a deformable soft member is provided for at least a portion of a wall of said reaction chamber, and a pressing section that seals said reaction chamber by pressing a predetermined portion of said soft member is provided on the exterior of the reaction vessel.

24. The reaction controlling device according to claim 14, comprising a sealing device that fluidically seals an interval between said nozzle or said storage chamber and said reaction chamber, and an interval between said reaction chamber and the exterior.

25. The reaction controlling device according to claim 14, comprising an optical information measurement section that obtains optical information within the one or two or more reaction chambers.

26. The reaction controlling device according to claim 25, wherein said optical information measurement section comprises:
- one or two or more irradiation end sections that irradiate light into said reaction chamber, and
- one or two or more light reception end sections that receive light from said reaction chamber,
- wherein said irradiation end section is provided such it makes contact with or is adjacent to a large wall face that has at least one largest area amongst a plurality of wall faces that surround said reaction chamber,
- and wherein said light reception end section is provided such that it makes contact with, is adjacent to, or is able to approach and separate from, at least one wall face excluding a largest wall face.

27. The reaction controlling device according to claim 25, wherein said optical information measurement section comprises:
- one or two or more irradiation end sections that irradiate light into said reaction chamber, and
- one or two or more light reception end sections that receive light from said reaction chamber,
- and wherein said irradiation end section and said light reception end section are provided such that they make contact with, are adjacent to, or are able to approach and separate from one wall face of a plurality of wall faces that surround said reaction chamber.

28. The reaction controlling device according to claim 25, wherein said optical information measurement section comprises:
- one or two or more irradiation end sections that irradiate light into said reaction chamber, and
- one or two or more light reception end sections that receive light from said reaction chamber,
- and wherein said irradiation end section of said optical information measurement section is one wall face amongst a plurality of wall faces that surround said reaction chamber, and is provided such that it makes contact with, is adjacent to, or is able to approach and separate from a portion that is coated or is built in with a conductive film serving as said temperature raising and lowering body.

* * * * *